(12) United States Patent
Olmstead et al.

(10) Patent No.: US 11,104,679 B2
(45) Date of Patent: Aug. 31, 2021

(54) PKC INHIBITOR SOLID STATE FORMS

(71) Applicant: MingSight Pharmaceuticals, Inc., San Diego, CA (US)

(72) Inventors: Kay Olmstead, Escondido, CA (US); Julian Northen, Sunderland Tyne and Wear (GB)

(73) Assignee: MINGSIGHT PHARMACEUTICALS, INC., San Diego, CA (US)

( * ) Notice: Subject to any disclaimer, the term of this patent is extended or adjusted under 35 U.S.C. 154(b) by 0 days.

(21) Appl. No.: 16/615,784

(22) PCT Filed: May 25, 2018

(86) PCT No.: PCT/US2018/034740
§ 371 (c)(1),
(2) Date: Nov. 21, 2019

(87) PCT Pub. No.: WO2018/218205
PCT Pub. Date: Nov. 29, 2018

(65) Prior Publication Data
US 2020/0223850 A1  Jul. 16, 2020

Related U.S. Application Data

(60) Provisional application No. 62/511,210, filed on May 25, 2017.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01); *C07B 2200/13* (2013.01)

(58) Field of Classification Search
CPC .................................................. C07D 487/04
See application file for complete search history.

(56) References Cited

U.S. PATENT DOCUMENTS

| | | | |
|---|---|---|---|
| 8,183,255 B2 | 5/2012 | Li et al. | |
| 8,877,761 B2 | 11/2014 | Li et al. | |
| 9,518,060 B2 | 12/2016 | Li et al. | |
| 10,316,045 B2 | 6/2019 | Li et al. | |
| 2015/0099743 A1 | 4/2015 | Li et al. | |
| 2016/0032249 A1 | 2/2016 | Melton et al. | |

FOREIGN PATENT DOCUMENTS

| | | | |
|---|---|---|---|
| WO | 2004071486 | * | 8/2004 |
| WO | WO-2008096260 A1 | | 8/2008 |
| WO | WO-2015179847 A1 | | 11/2015 |
| WO | WO-2018218205 A1 | | 11/2018 |

OTHER PUBLICATIONS

Hancock et al. Pharmaceutical Research. vol. 17. No. 4. 2000, p. 1-8.*
Grant et al. Discovery of a novel class of targeted kinase inhibitors that blocks protein kinase C signaling and ameliorates retinal vascular leakage in a diabetic rat model. Eur J Pharmacol 627(1-3):16-25 (2010).
PCT/US2018/034740 International Search Report and Written Opinion dated Aug. 24, 2018.
Pubmed compound summary for CID 25155745, 'PKC-IN-1', U.S. National Library of Medicine, dated Feb. 23, 2009.
Lee et al. A practical guide to pharmaceutical polymorph screening & selection. Asian Journal of Pharmaceutical Sciences 9(4):163-175 (2014).

* cited by examiner

*Primary Examiner* — Emily A Bernhardt
(74) *Attorney, Agent, or Firm* — Wilson Sonsini Goodrich & Rosati

(57) ABSTRACT

The present disclosure relates to various solid state forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and methods of making the same. Such forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine are useful in preparation of pharmaceutical compositions and dosage forms for the treatment of cancer, immune disorders and inflammation.

13 Claims, 50 Drawing Sheets

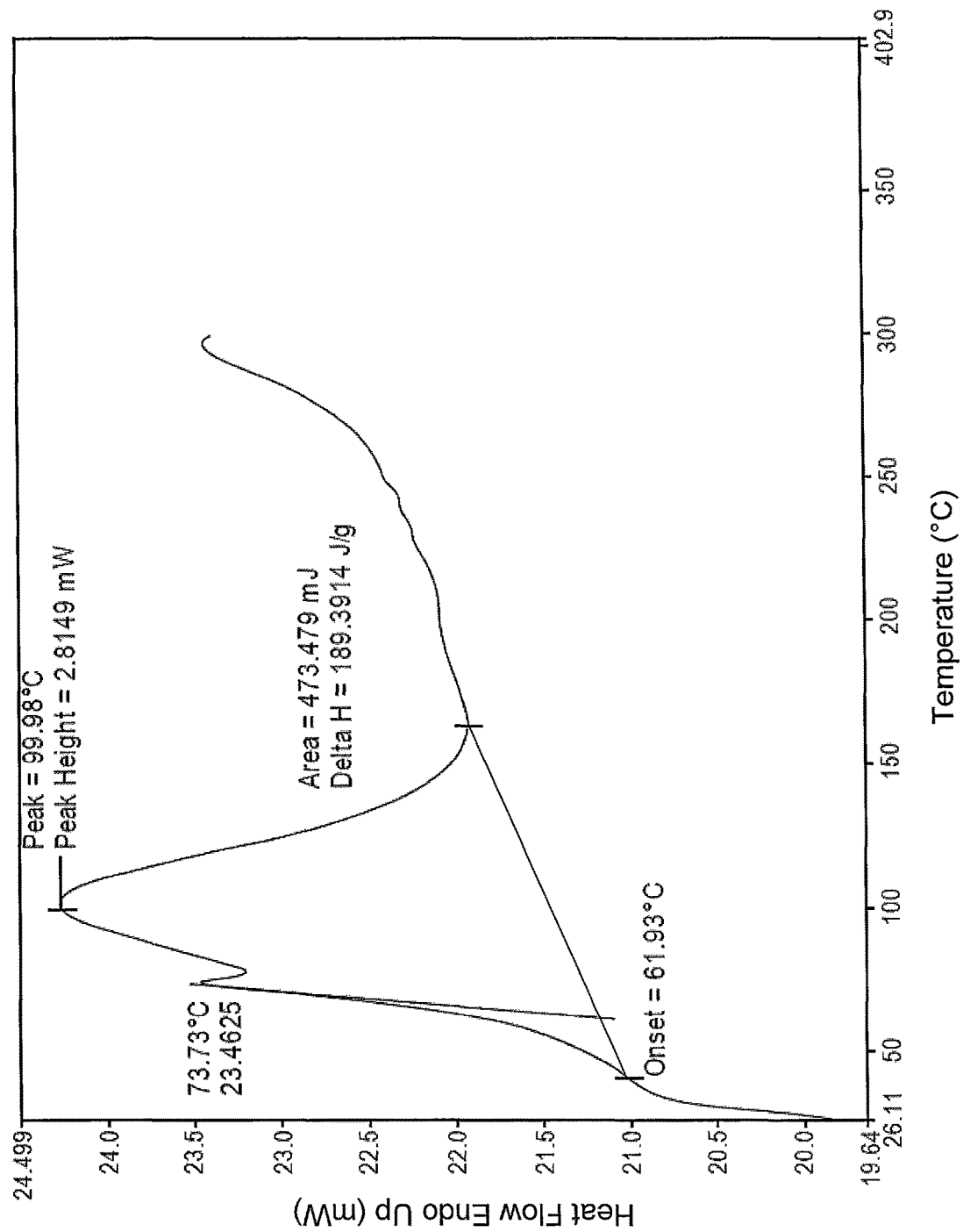

PKC INHIBITOR SOLID STATE FORMS

CROSS-REFERENCE TO RELATED APPLICATION

This application claims benefit of U.S. Patent Application No. 62/511,210, filed on May 25, 2017, which is hereby incorporated by reference in its entirety.

BACKGROUND OF THE INVENTION

The present disclosure relates to a protein kinase inhibitor compound and pharmaceutical compositions of said compound as well as the use of said compound in pharmaceutical compositions and medicine.

SUMMARY OF THE INVENTION

The present disclosure relates to various solid state forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and methods of making the same. Such forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine are useful in the treatment of cancer, immune disorders and inflammation.

Provided herein is a composition comprising amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is a composition comprising crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is a composition comprising crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is characterized by an X-ray diffraction pattern reflection at a 2 theta value of 18.1.

Provided herein is a composition comprising crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is a composition comprising crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine characterized by an X-ray diffraction pattern reflection at a 2 theta value of 16.3.

Provided herein is a composition comprising crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is a composition comprising crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine characterized by an X-ray diffraction pattern reflection at a 2 theta value of 17.9.

Provided herein is a composition comprising crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is a composition comprising crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine characterized by an X-ray diffraction pattern reflection at a 2 theta value of 17.3.

Provided herein is a composition comprising crystalline Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is a composition comprising crystalline hydrate Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine characterized by an X-ray diffraction pattern reflection at a 2 theta value of 4.4.

Provided herein is a composition comprising crystalline Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is a composition comprising crystalline hydrate Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine characterized by an X-ray diffraction pattern reflection at a 2 theta value of 4.4.

Provided herein is a composition comprising crystalline Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is a composition comprising crystalline hydrate Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine characterized by an X-ray diffraction pattern reflection at a 2 theta value of 15.7.

Provided herein is the compound 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine or a pharmaceutically acceptable salt, solution or hydrate thereof, free of bis(3-((5-fluoro-2-methylpyrimidin-4-yl)amino)-6,6-dimethyl-4,6-dihydropyrrolo[3,4-c]pyrazol-5(1H)-yl)methanone.

Provided herein is the compound 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine or a pharmaceutically acceptable salt, solution or hydrate thereof, substantially free of bis(3-((5-fluoro-2-methylpyrimidin-4-yl)amino)-6,6-dimethyl-4,6-dihydropyrrolo[3,4-c]pyrazol-5(1H)-yl)methanone.

Provided herein is the compound 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine or a pharmaceutically acceptable salt, solution or hydrate thereof, free of ethyl 5-((2S,5R)-2,5-dimethyl-4-((tetrahydro-2H-pyran-4-yl)methyl)piperazine-1-carbonyl)-3-((5- fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl) methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate.

Provided herein is the compound 5-{[(2S,5R)-2,5-dimethyl-4-(tetrahydro-2H-pyran-4-ylmethyl)piperazin-1-yl] carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt, solution or hydrate thereof, substantially free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate.

Provided herein is a pharmaceutical composition comprising amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and at least one pharmaceutically acceptable excipient.

Provided herein is a pharmaceutical composition comprising crystalline hydrate Form B of 5-{[(2S,5R)-2,5-dimethyl-4-(tetrahydro-2H-pyran-4-ylmethyl)piperazin-1-yl] carbonyl}-N-(5-fluoro-2-methylpyrimidin-4-yl)-6,6-dimethyl-1,4,5,6-tetrahydropyrrolo[3,4-c]pyrazol-3-amine and at least one pharmaceutically acceptable excipient.

Provided herein is a pharmaceutical composition comprising crystalline hydrate Form D of 5-{[(2S,5R)-2,5-dimethyl-4-(tetrahydro-2H-pyran-4-ylmethyl)piperazin-1-yl] carbonyl}-N-(5-fluoro-2-methylpyrimidin-4-yl)-6,6-dimethyl-1,4,5,6-tetrahydropyrrolo[3,4-c]pyrazol-3-amine and at least one pharmaceutically acceptable excipient.

Provided herein is a pharmaceutical composition comprising crystalline hydrate Form L of 5-{[(2S,5R)-2,5-dimethyl-4-(tetrahydro-2H-pyran-4-ylmethyl)piperazin-1-yl] carbonyl}-N-(5-fluoro-2-methylpyrimidin-4-yl)-6,6-dimethyl-1,4,5,6-tetrahydropyrrolo[3,4-c]pyrazol-3-amine and at least one pharmaceutically acceptable excipient.

Provided herein is a pharmaceutical composition comprising crystalline Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and at least one pharmaceutically acceptable excipient.

Provided herein is a pharmaceutical composition comprising crystalline Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and at least one pharmaceutically acceptable excipient.

Provided herein is a pharmaceutical composition comprising crystalline Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and at least one pharmaceutically acceptable excipient.

Provided herein is a pharmaceutical composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and at least one pharmaceutically acceptable excipient.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The features of the invention are set forth with particularity in the appended claims. A better understanding of the features of the present invention will be obtained by reference to the following detailed description that sets forth illustrative embodiments, in which the principles of the invention are utilized, and the accompanying drawings of which:

FIG. 2a shows the differential scanning calorimetry pattern of amorphous solid 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

DETAILED DESCRIPTION OF THE INVENTION

Figure 1:
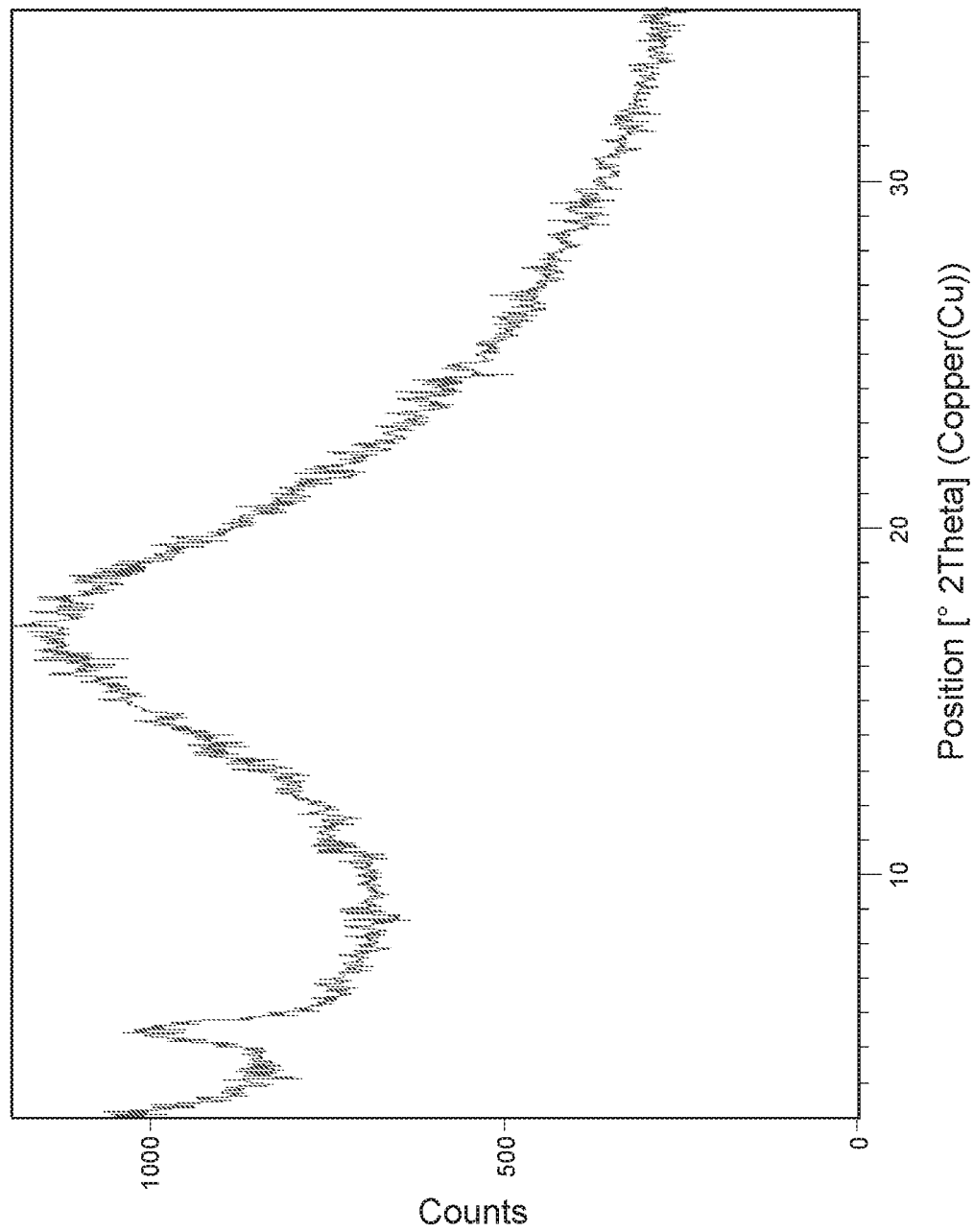
FIG. 1 shows the X-ray powder diffractogram of amorphous solid 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Compounds that are kinase inhibitors have the potential to provide therapeutically effective pharmaceutical compositions that would be expected to have beneficial and improved pharmaceutical properties for the treatment of kinase related conditions or disorders such as cancer and other proliferative disorders.

Discussed herein is 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and referred to herein as Compound 1. Compound 1 has been previously described in WO 2008/096260 and related patents and patent applications, e.g. U.S. Pat. Nos. 8,183,255, 8,877,761, 9,518,060 and U.S. patent application Ser. No. 15/376,279, each of which is incorporated by reference in their entirety.

Compound 1

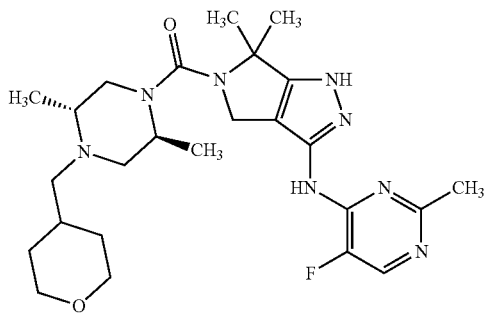

5-{[2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine A summary of the Protein Kinase C (PKC) inhibition by Compound 1 is provided in Table 1. The methods for these determinations have been described (Grant, et al. 2010, Eur. J. Pharmacol. 627:16-25). Compound 1 is a potent, ATP-competitive and reversible inhibitor of conventional PKC enzymes with a Ki=5.3 nM for recombinant PKC beta and a Ki=10.4 nM for recombinant PKC alpha. It also is a potent inhibitor of the novel isoform PKC theta with an $IC_{50}$=25.6 nM. Furthermore, it demonstrated some potency for conventional isoform PKC gamma with an $IC_{50}$=57.5 nM. Otherwise, it demonstrated a high degree of selectivity for the other members of the conventional, novel and atypical isoforms of PKC as shown by lower potency against these isoforms (Table 1). Compound 1 does not significantly inhibit PKC delta.

TABLE 1

| In Vitro Assays | $IC_{50}$(nM) | Ki (nM) |
|---|---|---|
| Human PKC alpha | | 10.4 |
| Human PKC betaII | | 5.3 |
| Human PKC alpha | 2.3 | |
| Human PKC betaI | 8.1 | |
| Human PKC betaII | 7.6 | |
| Human PKC theta | 25.6 | |
| Human PKC gamma | 57.5 | |
| Human PKC mu | 314 | |
| Human PKC epsilon | 808 | |
| Human PKC delta | >1000 | |
| Human PKC eta | >1000 | |
| Human PKC iota | >1000 | |
| Human PKC zeta | >1000 | |
| Human PRKCN (PKD3) | 131 | |
| pSHP2 (PKCβ cell assay) | 9.8 | |
| Interleukin-8 release | 39 | |

As a selective inhibitor of PKC, Compound 1 is useful in the treatment of conditions in which PKC has demonstrated a role in the pathology, such as cancer, immune disorders and inflammation. Two critical aspects in the development of Compound 1 as a useful therapy for such diseases and disorders are the discovery of practical methods for the preparation of Compound 1, and the discovery of pharmaceutically acceptable forms of Compound 1 and pharmaceutical compositions comprising said forms.

As used herein, the term "amorphous" or "amorphous solid form" refers to a solid form which is substantially free of any crystalline solid state form. One embodiment provides a composition wherein substantially free means less than about 10% (w/w), less than about 9% (w/w), less than about 8% (w/w), less than about 7% (w/w), less than about 6% (w/w), less than about 5% (w/w), less than about 4.75% (w/w), less than about 4.5% (w/w), less than about 4.25% (w/w), less than about 4% (w/w), less than about 3.75% (w/w), less than about 3.5% (w/w), less than about 3.25% (w/w), less than about 3% (w/w), less than about 2.75% (w/w), less than about 2.5% (w/w), less than about 2.25% (w/w), less than about 2% (w/w), less than about 1.75% (w/w), less than about 1.5% (w/w), less than about 1.25% (w/w), less than about 1% (w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.25% (w/w), less than about 0.20% (w/w), less than about 0.15% (w/w), less than about 0.1% (w/w), less than about 0.08% (w/w), or less than about 0.05% (w/w). One embodiment provides a composition wherein substantially free means an undetectable amount. One embodiment provides a composition wherein substantially free means less than about 5% (w/w), less than about 3% (w/w), less than about 1% (w/w), less than about 0.5% (w/w), or less than about 0.2% (w/w).

As used herein, the term "crystalline," "highly crystalline," "crystalline solid form," or "highly crystalline solid form" refers to a solid form which is substantially free of any amorphous solid state form. In some embodiments, the crystalline solid form is a single solid state form, e.g. crystalline Form A. One embodiment provides a composition wherein substantially free means less than about 10% (w/w), less than about 9% (w/w), less than about 8% (w/w), less than about 7% (w/w), less than about 6% (w/w), less than about 5% (w/w), less than about 4.75% (w/w), less than about 4.5% (w/w), less than about 4.25% (w/w), less than about 4% (w/w), less than about 3.75% (w/w), less than about 3.5% (w/w), less than about 3.25% (w/w), less than about 3% (w/w), less than about 2.75% (w/w), less than about 2.5% (w/w), less than about 2.25% (w/w), less than about 2% (w/w), less than about 1.75% (w/w), less than about 1.5% (w/w), less than about 1.25% (w/w), less than about 1% (w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.25% (w/w), less than about 0.20% (w/w), less than about 0.15% (w/w), less than about 0.1% (w/w), less than about 0.08% (w/w), or less than about 0.05% (w/w). One embodiment provides a composition wherein substantially free means an undetectable amount. One embodiment provides a composition wherein substantially free means less than about 5% (w/w), less than about 3% (w/w), less than about 1% (w/w), less than about 0.5% (w/w), or less than about 0.2% (w/w).

As used herein, the term "partially crystalline" or "partially crystalline material" refers to an ad-mixture of two or more solid state forms. In some embodiments, partially crystalline refers to an ad-mixture of an amorphous solid form and at least one crystalline solid form. Partially crystalline material is not amorphous.

In some embodiments, crystallinity of a solid form is determined by X-Ray Powder Diffraction (XRPD). In some embodiments, crystallinity of a solid form is determined by solid state NMR.

Provided herein is the amorphous solid form of 5-{[(2S, 5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the X-ray powder diffraction pattern as shown in FIG. 1.

One embodiment provides a composition wherein the amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits a differential scanning calorimetry pattern shown in FIG. 2a.

Figure 2B:
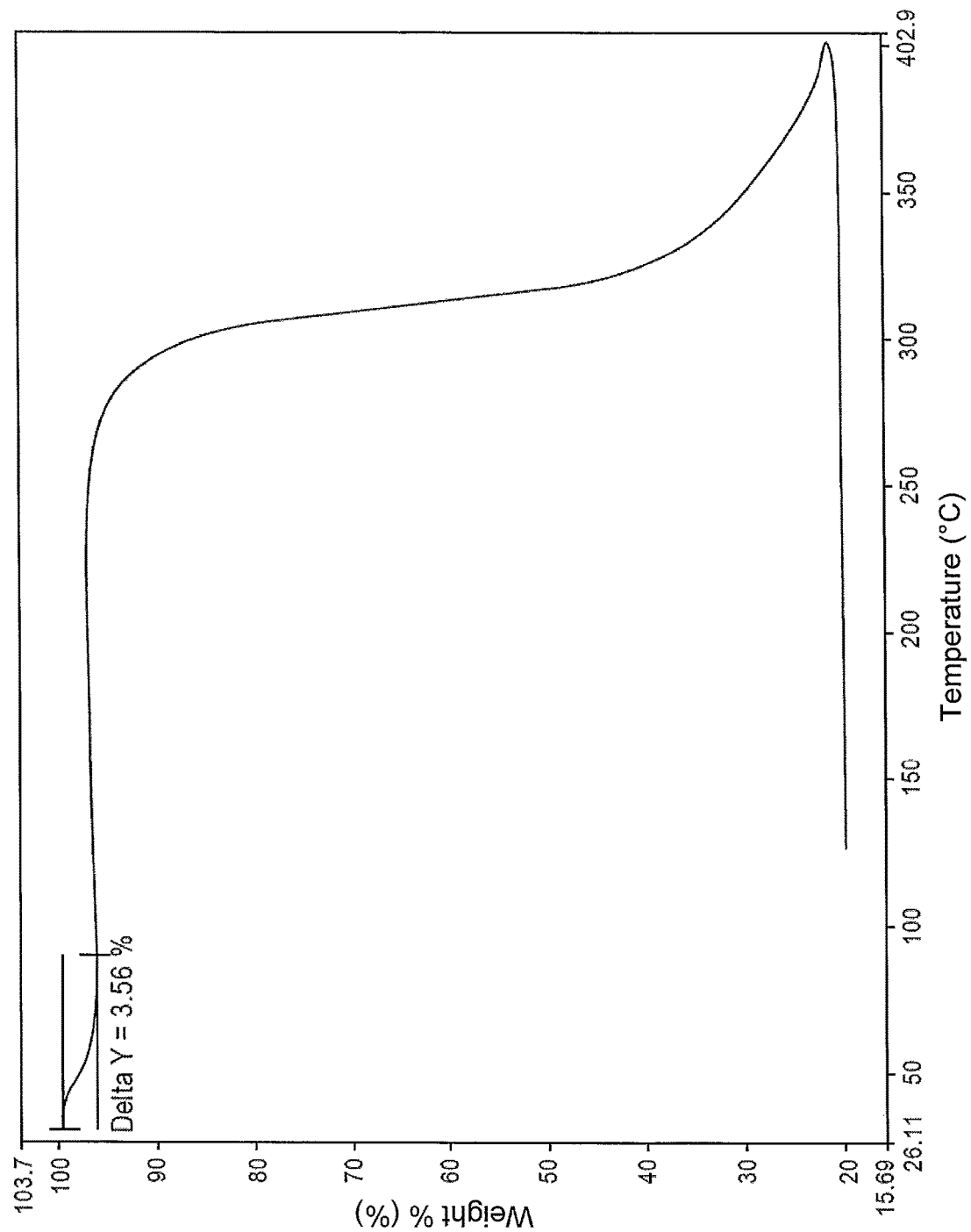
FIG. 2b shows the thermal gravimetric analysis pattern of amorphous solid 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits a thermogravimetric analysis pattern shown in FIG. 2b.

One embodiment provides a composition wherein the amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is stable over 36 months at ambient temperature. One embodiment provides a composition wherein the amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is stable over 60 months at ambient temperature.

One embodiment provides a composition wherein the amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine remains amorphous over 36 months at ambient temperature. One embodiment provides a composition wherein the amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine remains amorphous over 60 months at ambient temperature.

One embodiment provides a composition wherein the stability of amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is determined by the X-ray powder diffraction pattern.

Provided herein is the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Figure 3:
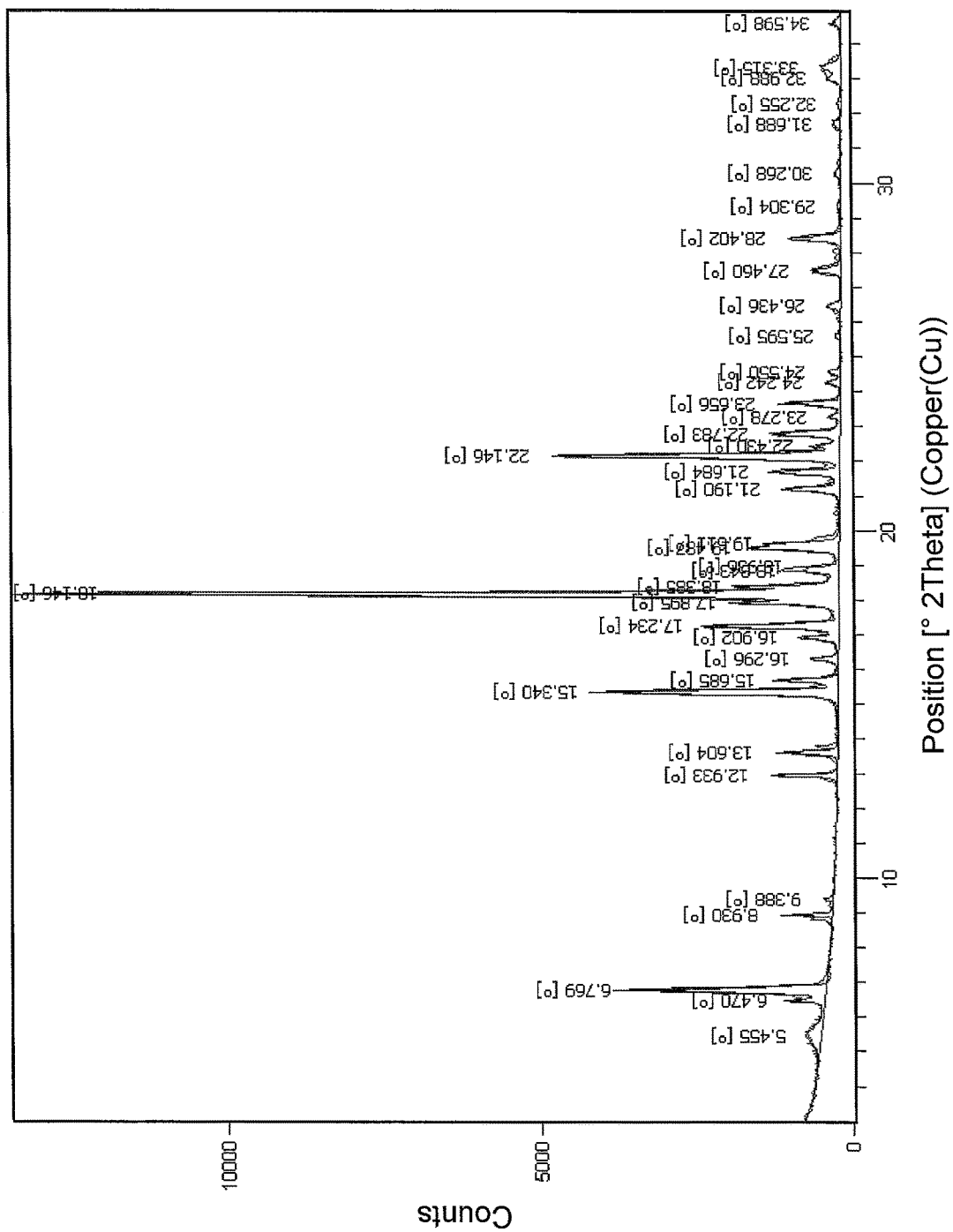
FIG. 3 shows the X-ray powder diffractogram of crystalline 2-propanol solvate Form A of 5-{[(2S,5R)-2,5-dimethyl-4-(tetrahydro-2H-pyran-4-ylmethyl)piperazin-1-yl] carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the X-ray powder diffraction pattern as shown in FIG. 3.

Provided herein is a composition comprising crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is characterized by an X-ray diffraction pattern reflection at a 2 theta value of 18.1.

One embodiment provides a composition wherein the crystalline Form A is further characterized by X-ray diffraction pattern reflections at 2 theta values of 6.8, 15.3 and 22.1.

One embodiment provides a composition wherein the crystalline Form A is further characterized by X-ray diffraction pattern reflections at 2 theta values of 12.9, 13.6, 15.7, 17.2, 21.2, 21.7, 22.8 and 28.4.

One embodiment provides a composition wherein the crystalline Form A is further characterized by at least one X-ray diffraction pattern reflection selected from a 2 theta value of 6.8, 12.9, 13.6, 15.3, 15.7, 17.2, 18.1, 21.2, 21.7, 22.1, 22.8 and 28.4.

One embodiment provides a composition wherein the crystalline Form A is further characterized by at least two X-ray diffraction pattern reflections selected from a 2 theta value of 6.8, 12.9, 13.6, 15.3, 15.7, 17.2, 18.1, 21.2, 21.7, 22.1, 22.8 and 28.4.

One embodiment provides a composition wherein the crystalline Form A is further characterized by at least three X-ray diffraction pattern reflections selected from a 2 theta value of 6.8, 12.9, 13.6, 15.3, 15.7, 17.2, 18.1, 21.2, 21.7, 22.1, 22.8 and 28.4.

One embodiment provides a composition wherein the crystalline Form A is further characterized by at least four X-ray diffraction pattern reflections selected from a 2 theta value of 6.8, 12.9, 13.6, 15.3, 15.7, 17.2, 18.1, 21.2, 21.7, 22.1, 22.8 and 28.4.

One embodiment provides a composition wherein the crystalline Form A is further characterized by at least five X-ray diffraction pattern reflections selected from a 2 theta value of 6.8, 12.9, 13.6, 15.3, 15.7, 17.2, 18.1, 21.2, 21.7, 22.1, 22.8 and 28.4.

One embodiment provides a composition wherein the crystalline Form A is further characterized by at least six X-ray diffraction pattern reflections selected from a 2 theta value of 6.8, 12.9, 13.6, 15.3, 15.7, 17.2, 18.1, 21.2, 21.7, 22.1, 22.8 and 28.4.

Figure 5:
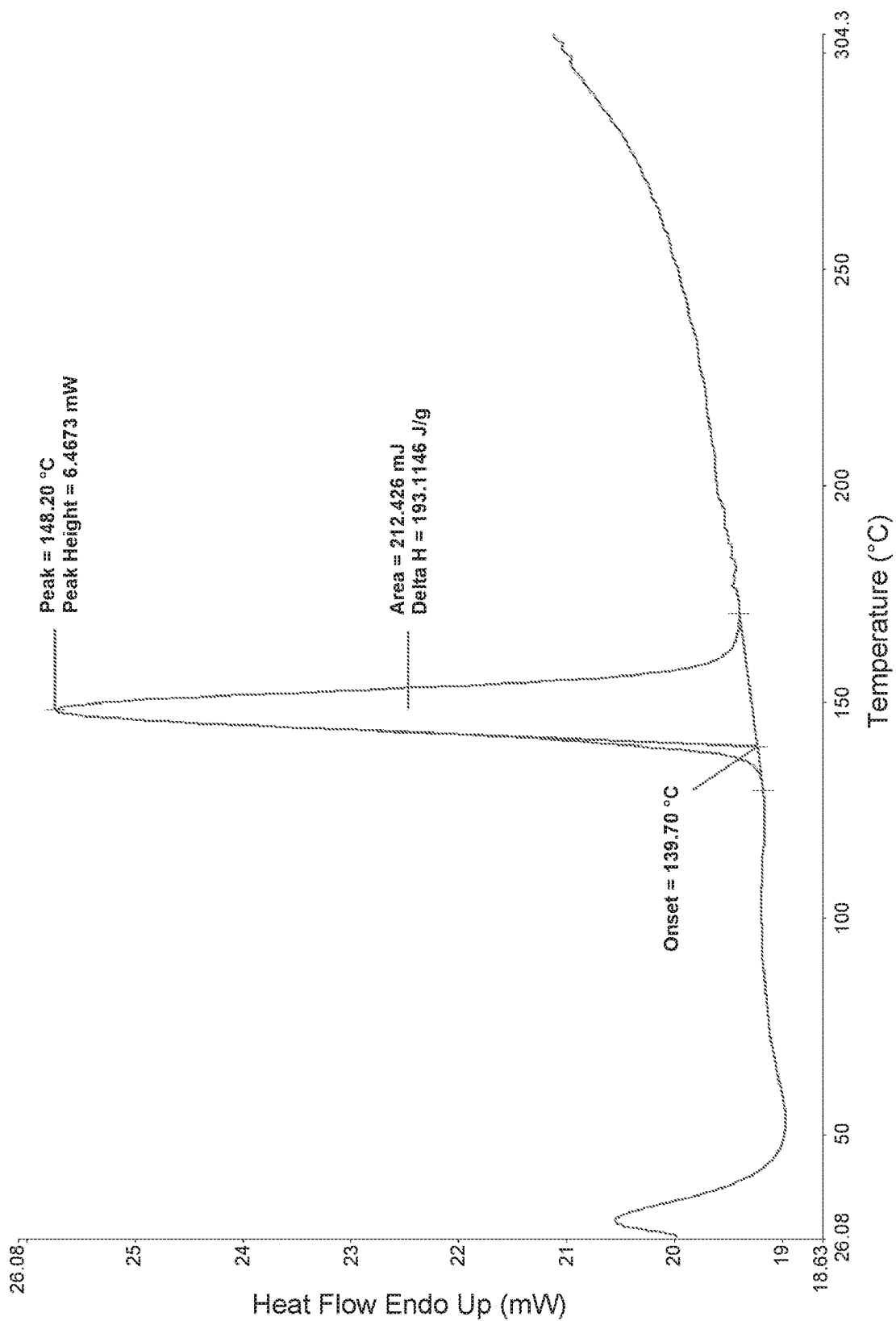
FIG. 5 shows the differential scanning calorimetry thermogram of crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c] pyrazol-3-amine.

One embodiment provides a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the differential scanning calorimetry pattern as shown in FIG. 5.

Figure 6:
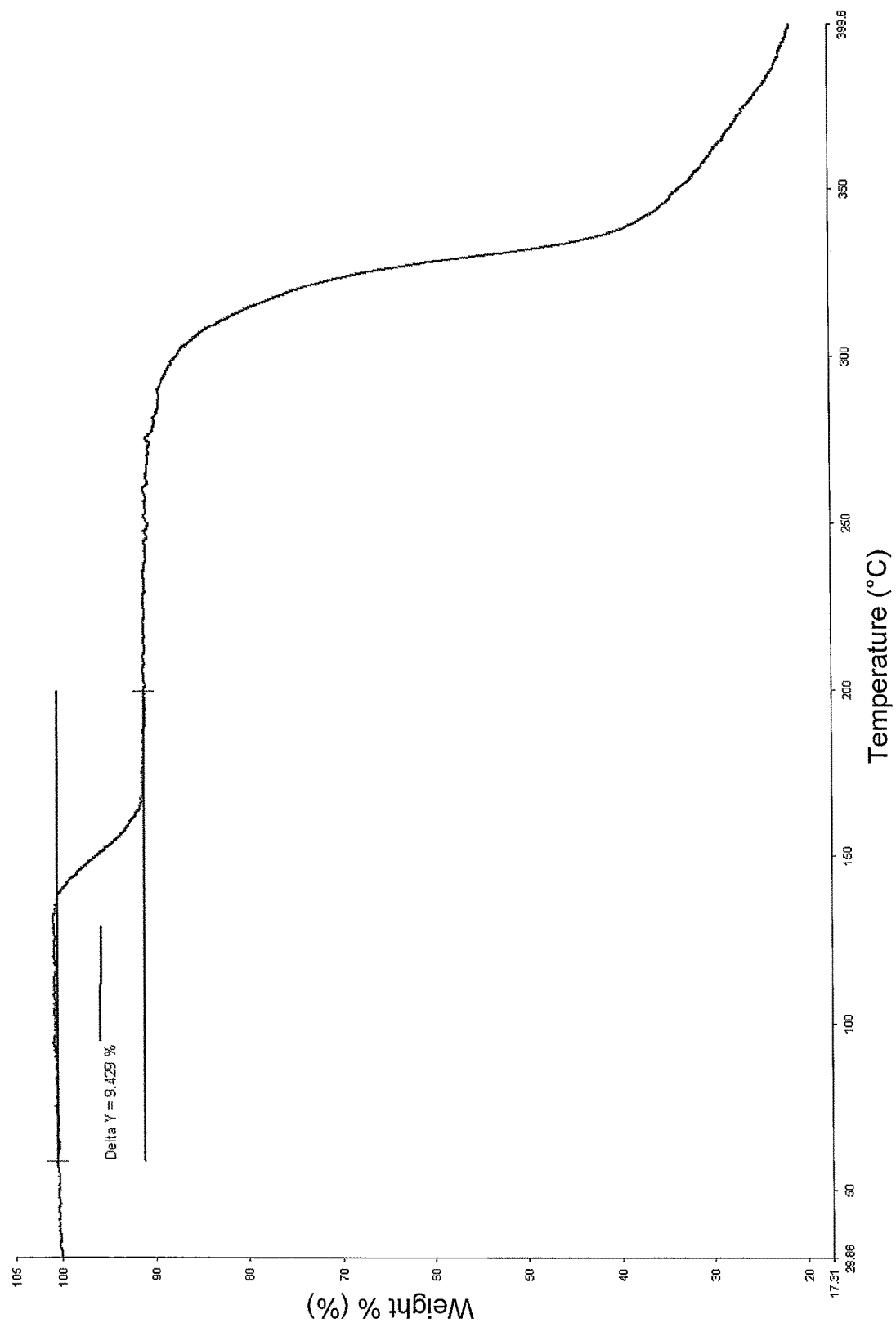
FIG. 6 shows the thermal gravimetric analysis thermogram of crystalline 2-propanol solvate Form A of 5-{[(2S, 5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the thermogravimetric analysis pattern as shown in FIG. 6.

Figure 7:
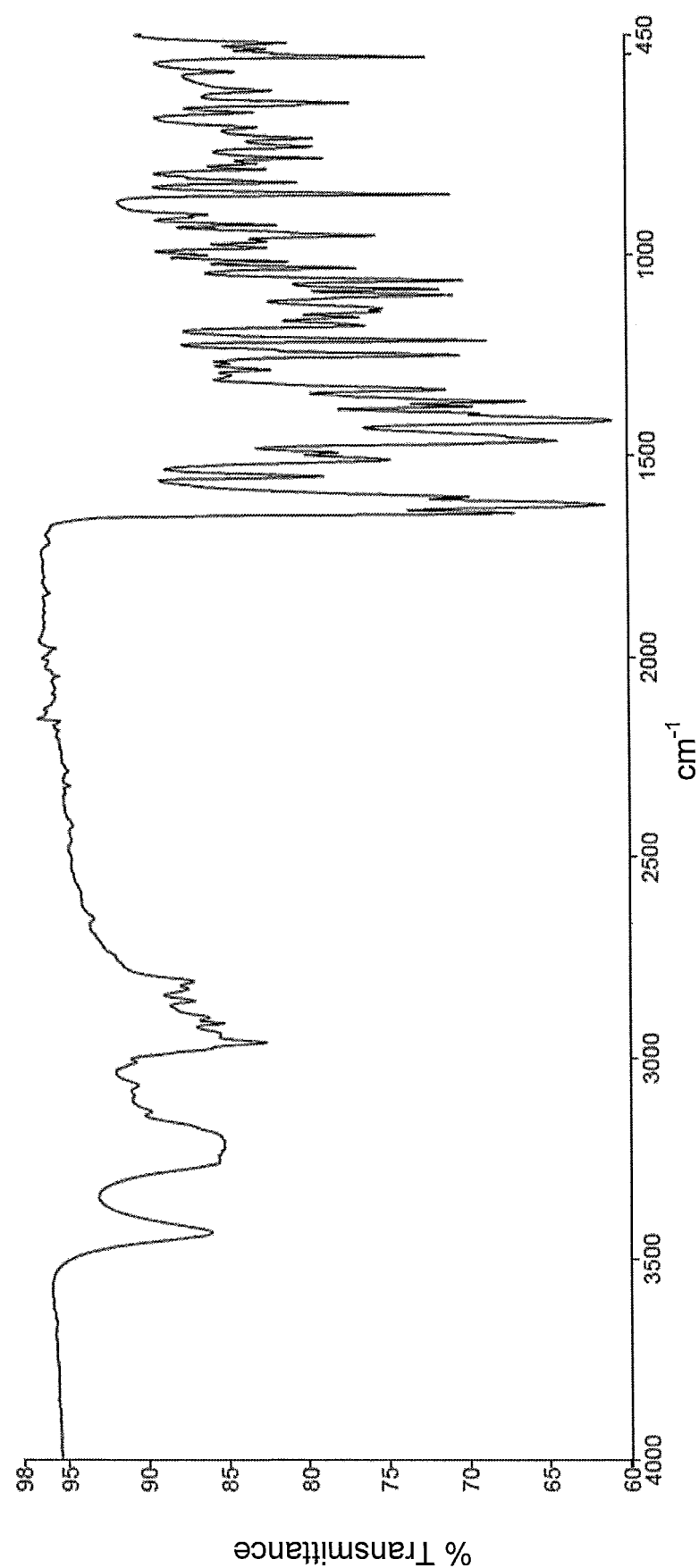
FIG. 7 shows the infrared spectrum of crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine without annotation.
Figure 8:
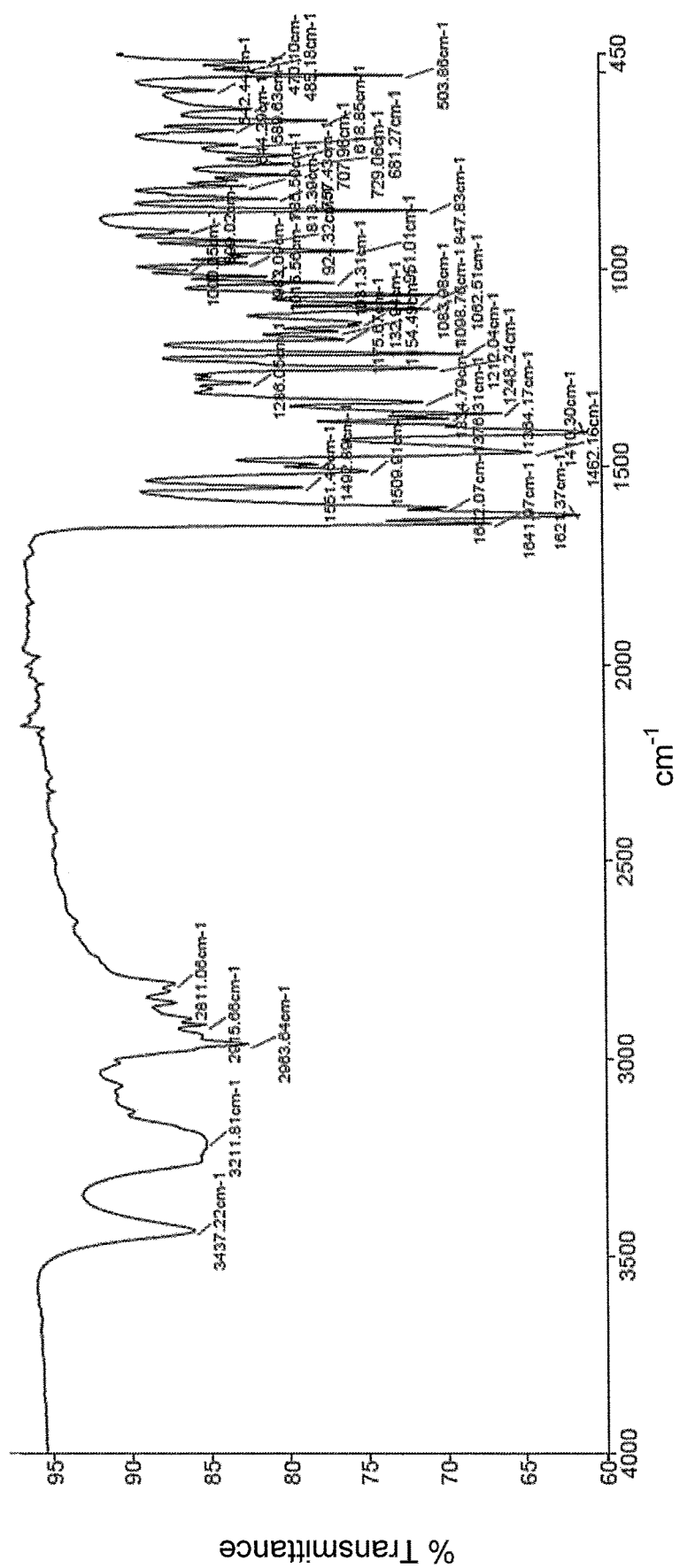
FIG. 8 shows the infrared spectrum of crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine] with peaks numerically identified at all wavenumbers.
Figure 9:
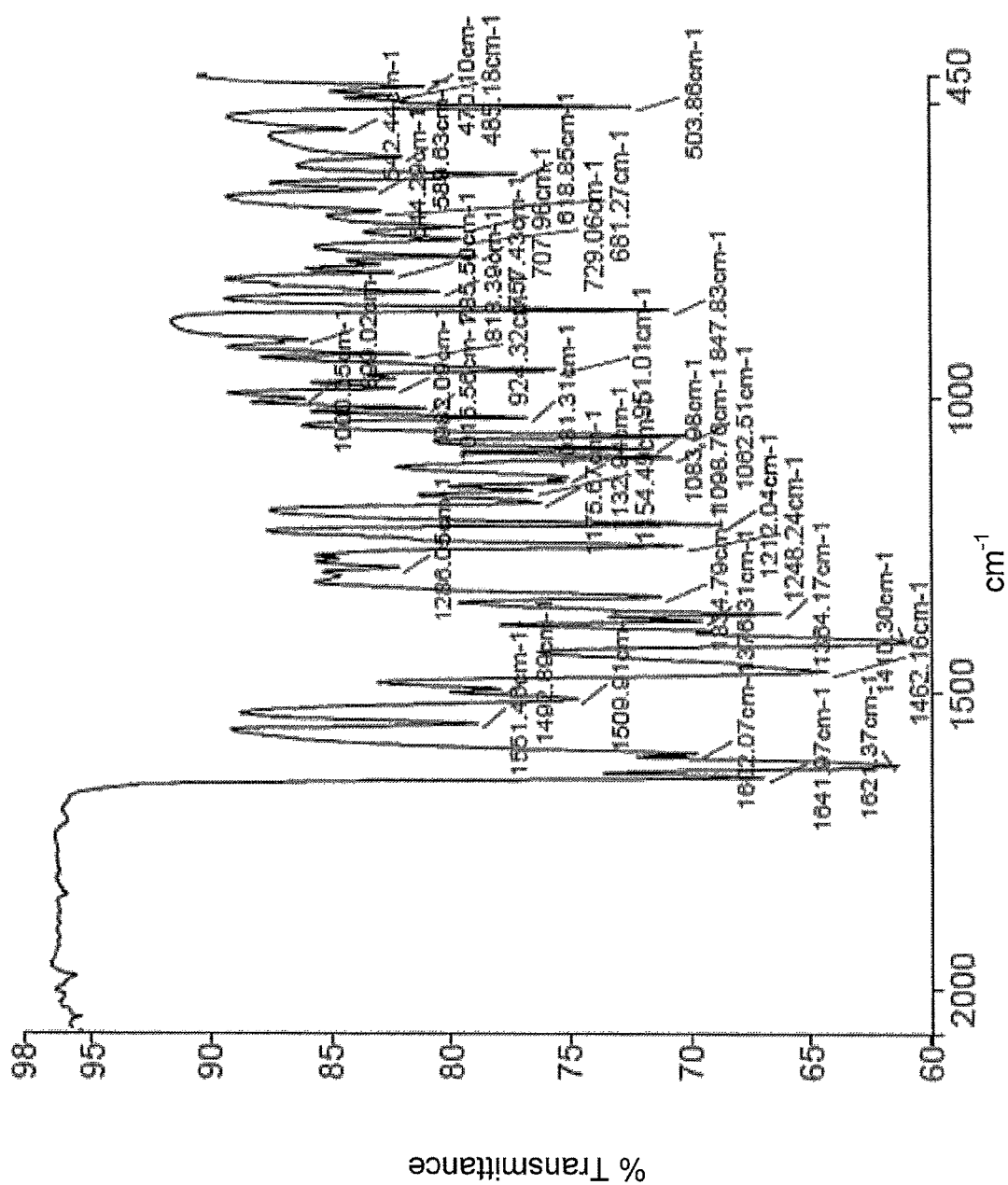
FIG. 9 shows the infrared spectrum of crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine with peaks numerically identified at low wavenumbers.

One embodiment provides a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the infrared spectrum as shown in FIG. 7, 8, or 9.

Provided herein is the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline hydrate Form B of 5-{[(2S,5R)-2,5-dimethyl-4-

Figure 10:
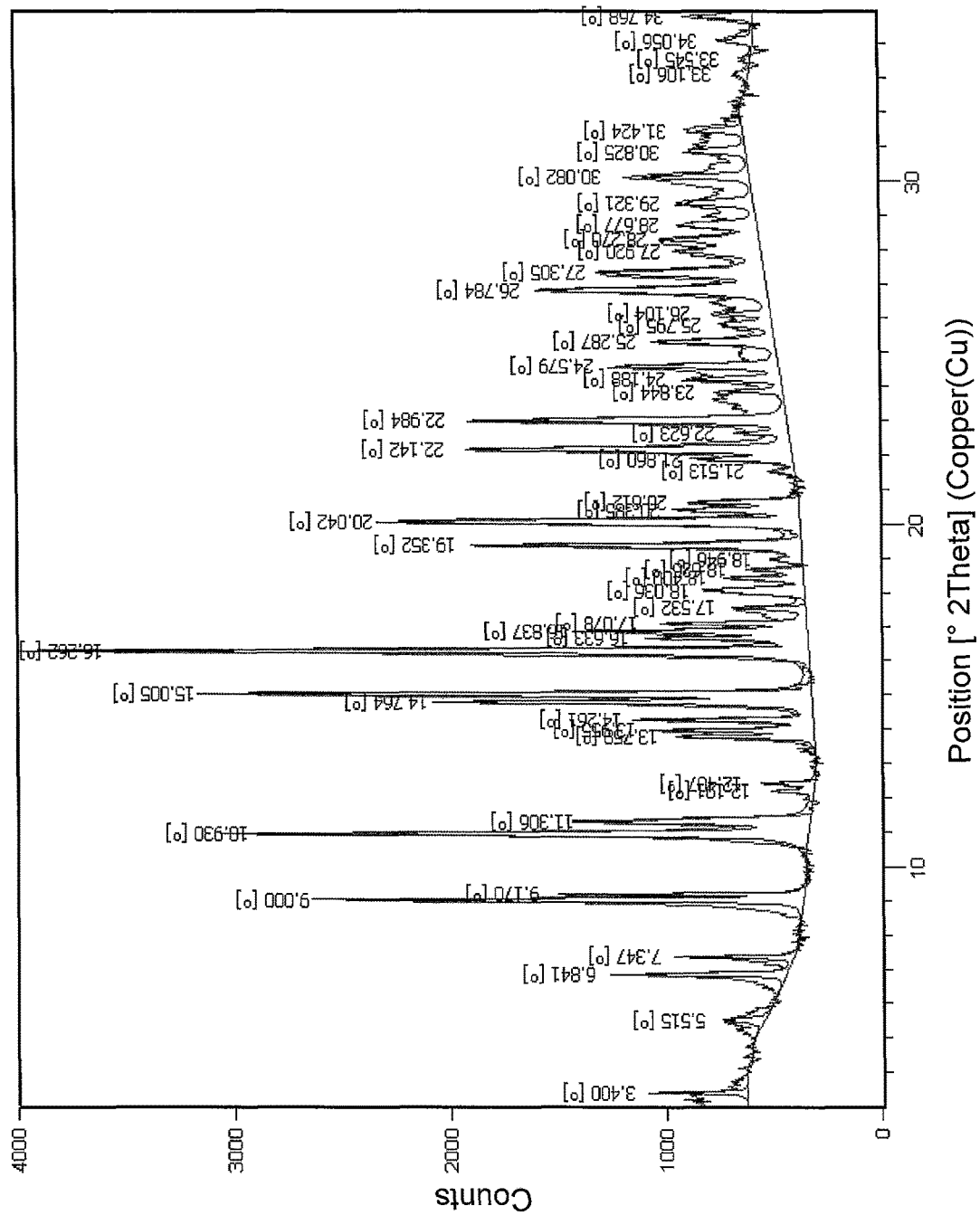
FIG. 10 shows the X-ray powder diffractogram of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine with peaks numerically identified.

(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the X-ray powder diffraction pattern as shown in FIG. 10.

Provided herein is a composition comprising crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine characterized by an X-ray diffraction pattern reflection at a 2 theta value of 16.3.

One embodiment provides a composition wherein the crystalline Form B is further characterized by X-ray diffraction pattern reflections at 2 theta values of 9.0, 10.9 and 15.0.

One embodiment provides a composition wherein the crystalline Form B is further characterized by X-ray diffraction pattern reflections at 2 theta values of 6.8, 9.2, 11.3, 14.8, 19.4, 20.0, 22.1, 23.0 and 26.8.

One embodiment provides a composition wherein the crystalline Form B is further characterized by at least one X-ray diffraction pattern reflection selected from a 2 theta value of 6.8, 9.0, 9.2, 10.9, 11.3, 14.8, 15.0, 16.3, 19.4, 20.0, 22.1, 23.0 and 26.8.

One embodiment provides a composition wherein the crystalline Form B is further characterized by at least two X-ray diffraction pattern reflections selected from a 2 theta value of 6.8, 9.0, 9.2, 10.9, 11.3, 14.8, 15.0, 16.3, 19.4, 20.0, 22.1, 23.0 and 26.8.

One embodiment provides a composition wherein the crystalline Form B is further characterized by at least three X-ray diffraction pattern reflections selected from a 2 theta value of 6.8, 9.0, 9.2, 10.9, 11.3, 14.8, 15.0, 16.3, 19.4, 20.0, 22.1, 23.0 and 26.8.

One embodiment provides a composition wherein the crystalline Form B is further characterized by at least four X-ray diffraction pattern reflections selected from a 2 theta value of 6.8, 9.0, 9.2, 10.9, 11.3, 14.8, 15.0, 16.3, 19.4, 20.0, 22.1, 23.0 and 26.8.

One embodiment provides a composition wherein the crystalline Form B is further characterized by at least five X-ray diffraction pattern reflections selected from a 2 theta value of 6.8, 9.0, 9.2, 10.9, 11.3, 14.8, 15.0, 16.3, 19.4, 20.0, 22.1, 23.0 and 26.8.

One embodiment provides a composition wherein the crystalline Form B is further characterized by at least six X-ray diffraction pattern reflections selected from a 2 theta value of 6.8, 9.0, 9.2, 10.9, 11.3, 14.8, 15.0, 16.3, 19.4, 20.0, 22.1, 23.0 and 26.8.

Figure 12:
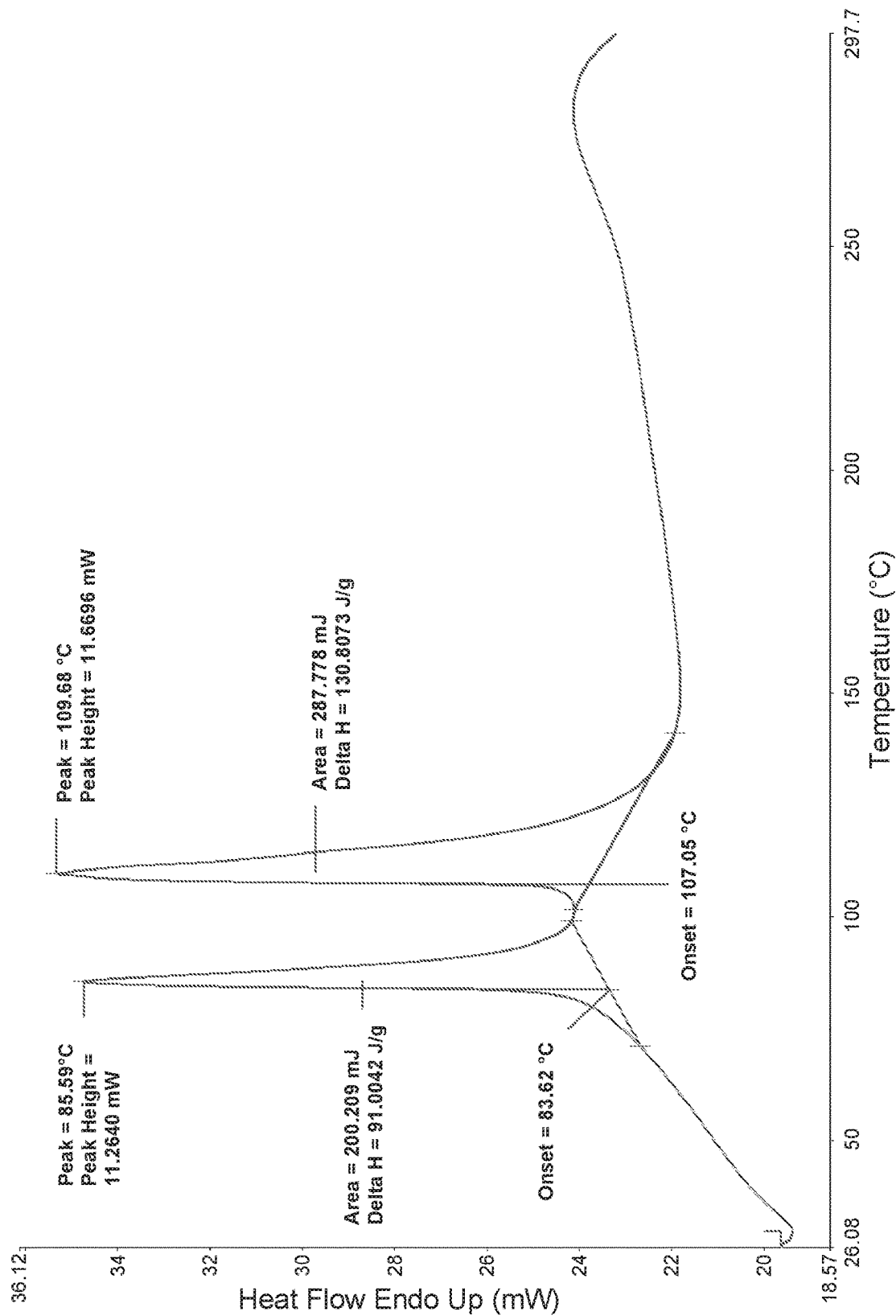
FIG. 12 shows the differential scanning calorimetry thermogram of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the differential scanning calorimetry pattern as shown in FIG. 12.

Figure 13:
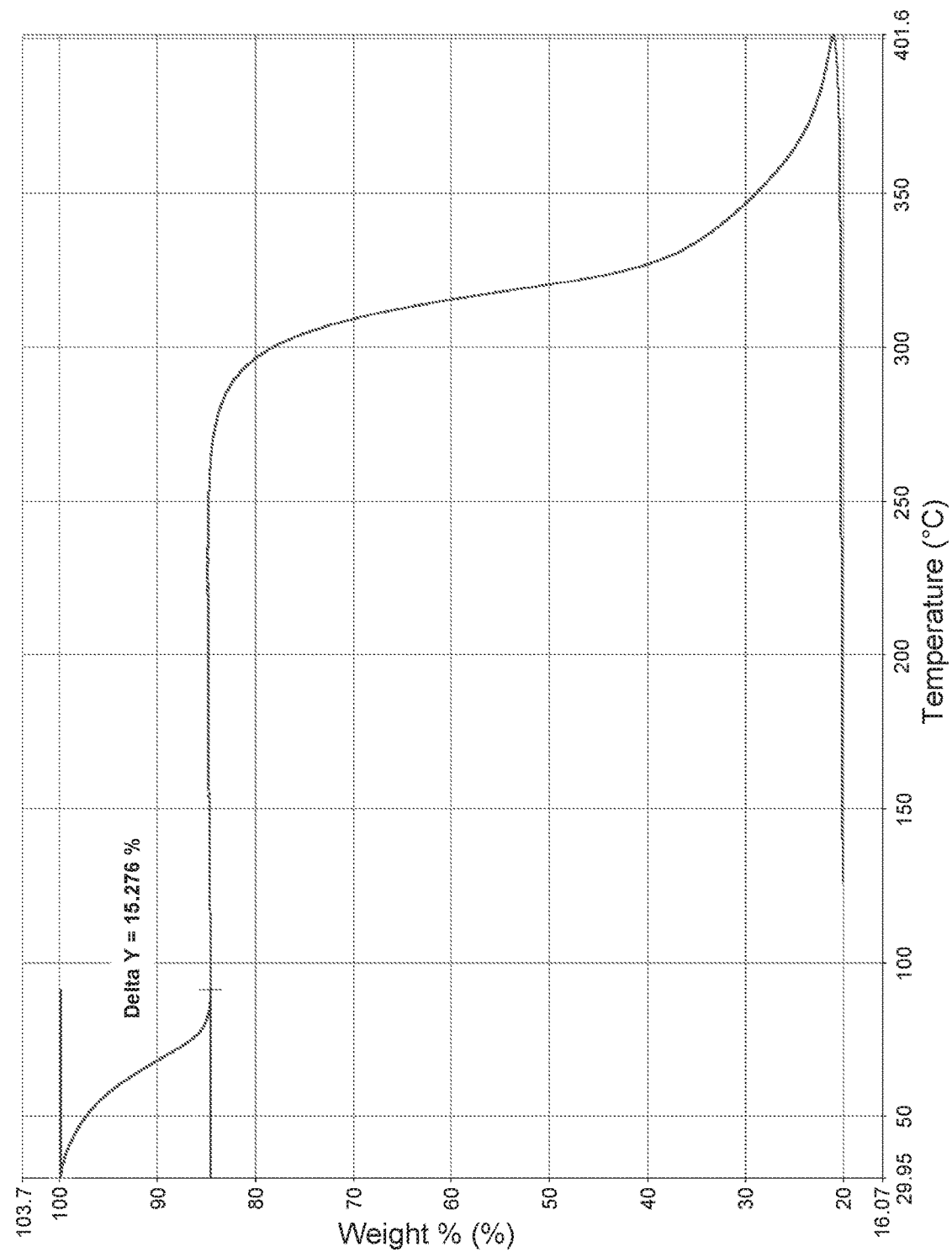
FIG. 13 shows the thermal gravimetric analysis thermogram of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the thermogravimetric analysis pattern as shown in FIG. 13.

Figure 14:
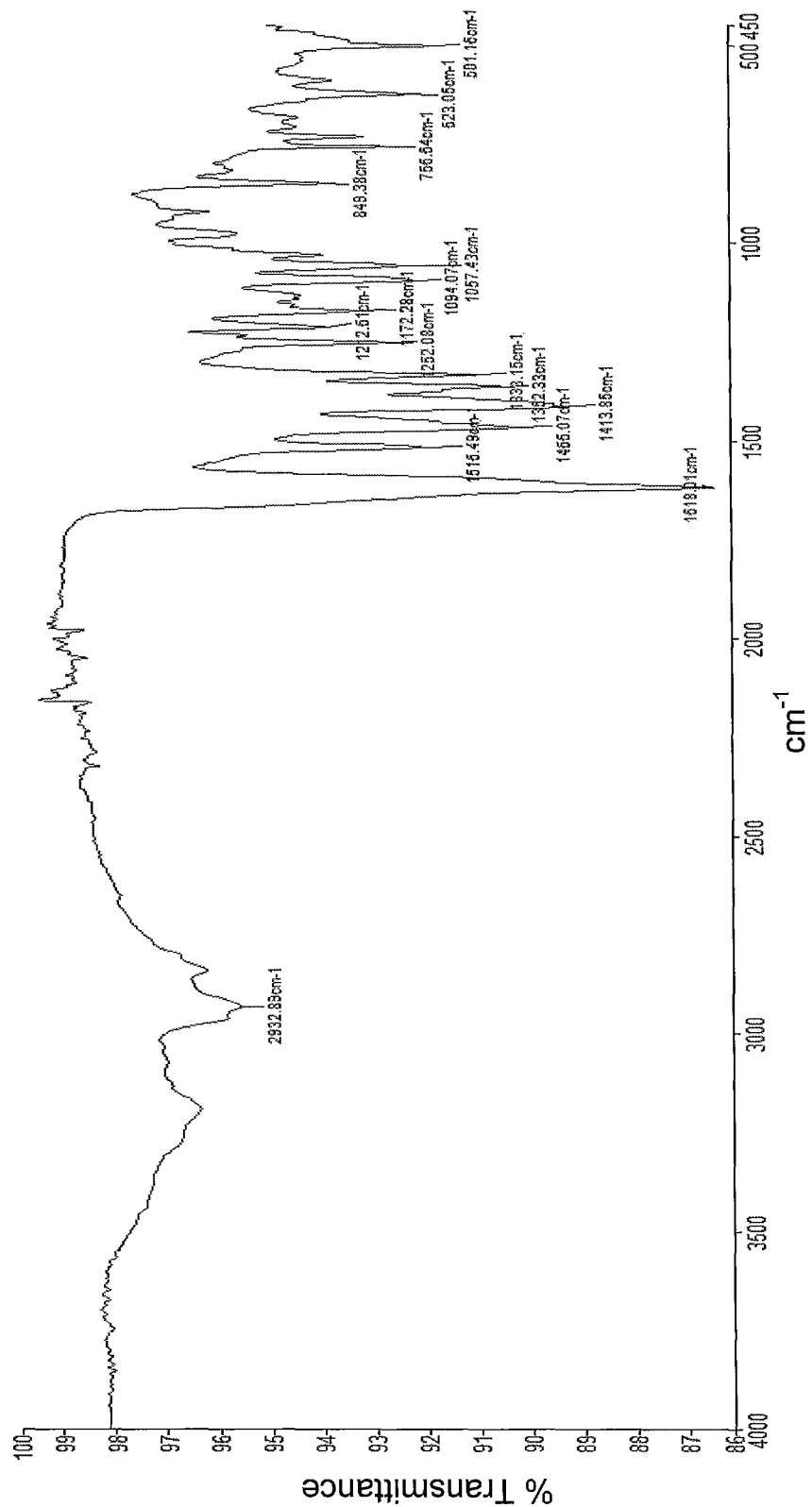
FIG. 14 shows the infrared spectrum of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the infrared spectrum as shown in FIG. 14.

Provided herein is the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Figure 17:
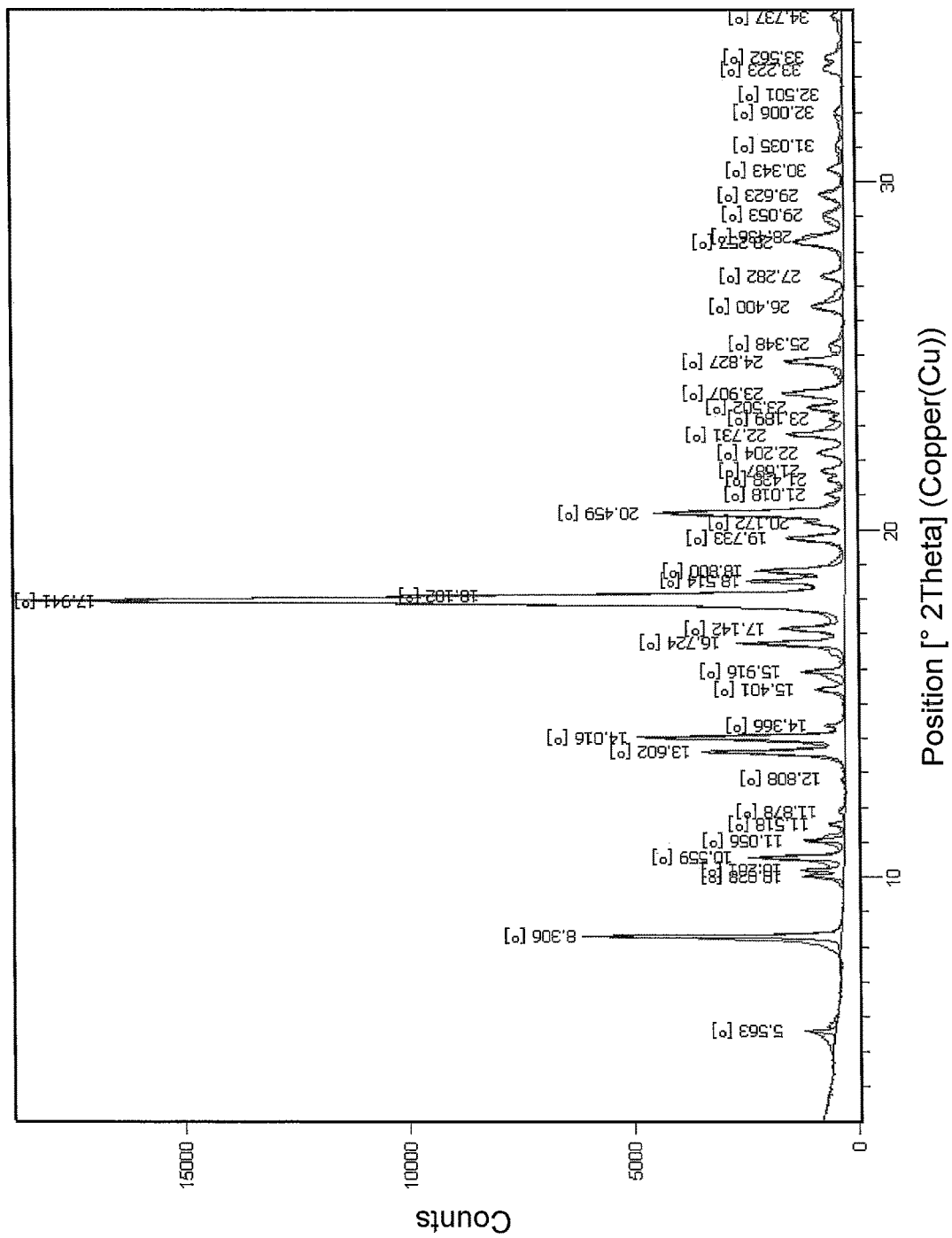
FIG. 17 shows the X-ray powder diffractogram of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine with peaks numerically identified.

One embodiment provides a composition wherein the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the X-ray powder diffraction pattern as shown in FIG. 17.

Provided herein is a composition comprising crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine characterized by an X-ray diffraction pattern reflection at a 2 theta value of 17.9.

One embodiment provides a composition wherein the crystalline Form D is further characterized by X-ray diffraction pattern reflections at 2 theta values of 8.3, 14.0 and 20.4.

One embodiment provides a composition wherein the crystalline Form D is further characterized by X-ray diffraction pattern reflections at 2 theta values of 5.5, 8.3, 10.5, 13.6, 16.7, 18.1, 18.7, 23.9, 24.8 and 28.2.

One embodiment provides a composition wherein the crystalline Form D is further characterized by at least one X-ray diffraction pattern reflection selected from a 2 theta value of 5.5, 8.3, 10.5, 13.6, 14.0, 16.7, 17.9, 18.1, 18.7, 20.4, 23.9, 24.8 and 28.2.

One embodiment provides a composition wherein the crystalline Form D is further characterized by at least two X-ray diffraction pattern reflections selected from a 2 theta value of 5.5, 8.3, 10.5, 13.6, 14.0, 16.7, 17.9, 18.1, 18.7, 20.4, 23.9, 24.8 and 28.2.

One embodiment provides a composition wherein the crystalline Form D is further characterized by at least three X-ray diffraction pattern reflections selected from a 2 theta value of 5.5, 8.3, 10.5, 13.6, 14.0, 16.7, 17.9, 18.1, 18.7, 20.4, 23.9, 24.8 and 28.2.

One embodiment provides a composition wherein the crystalline Form D is further characterized by at least four X-ray diffraction pattern reflections selected from a 2 theta value of 5.5, 8.3, 10.5, 13.6, 14.0, 16.7, 17.9, 18.1, 18.7, 20.4, 23.9, 24.8 and 28.2.

One embodiment provides a composition wherein the crystalline Form D is further characterized by at least five X-ray diffraction pattern reflections selected from a 2 theta value of 5.5, 8.3, 10.5, 13.6, 14.0, 16.7, 17.9, 18.1, 18.7, 20.4, 23.9, 24.8 and 28.2.

One embodiment provides a composition wherein the crystalline Form D is further characterized by at least six X-ray diffraction pattern reflections selected from a 2 theta value of 5.5, 8.3, 10.5, 13.6, 14.0, 16.7, 17.9, 18.1, 18.7, 20.4, 23.9, 24.8 and 28.2.

Figure 19:
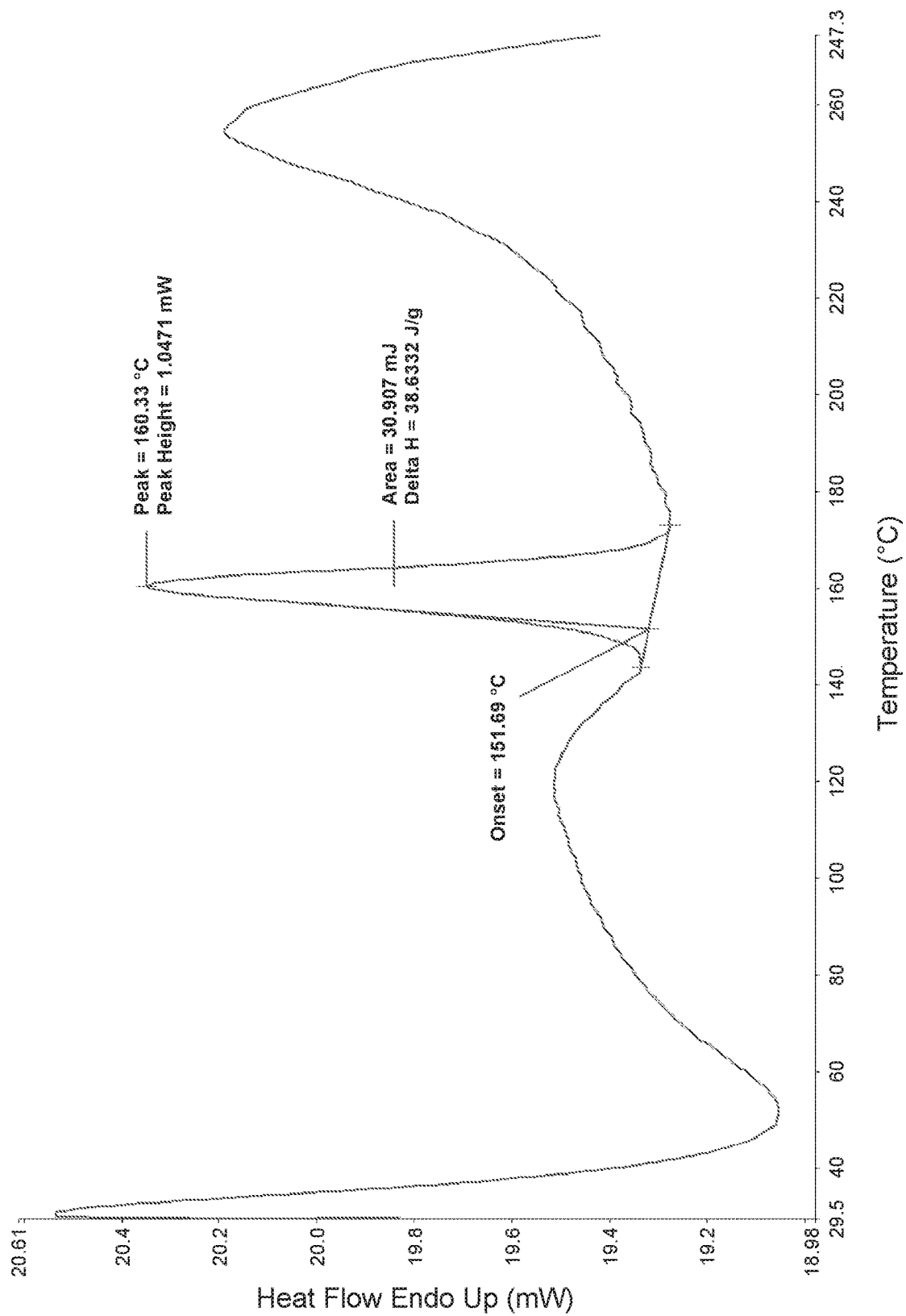
FIG. 19 shows the differential scanning calorimetry thermogram of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the differential scanning calorimetry pattern as shown in FIG. 19.

Figure 20:
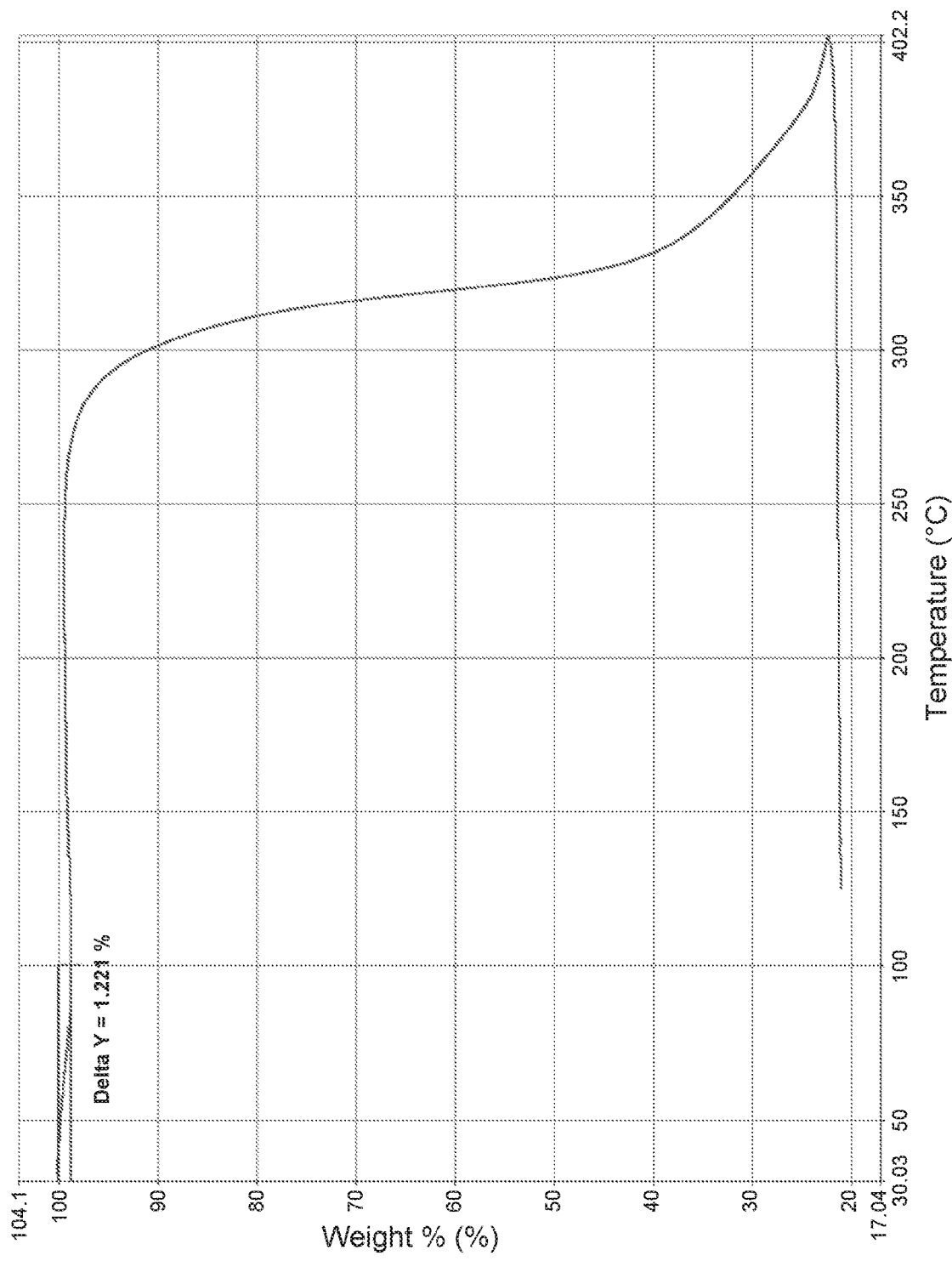
FIG. 20 shows the thermal gravimetric analysis thermogram of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the thermogravimetric analysis pattern as shown in FIG. 20.

Figure 21:
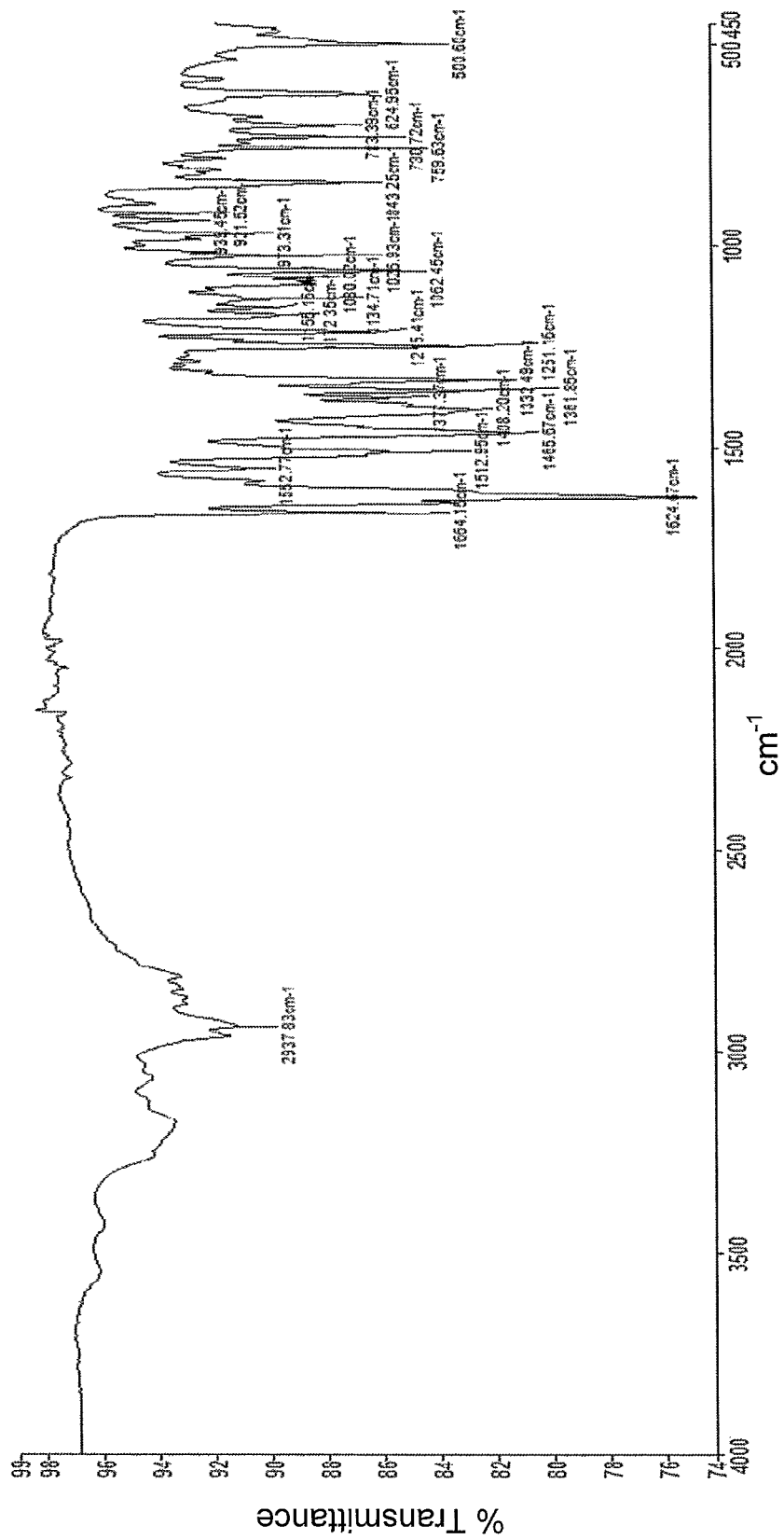
FIG. 21 shows the infrared spectrum of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine]

One embodiment provides a composition wherein the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the infrared spectrum as shown in FIG. 21.

Provided herein is the crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Figure 24:
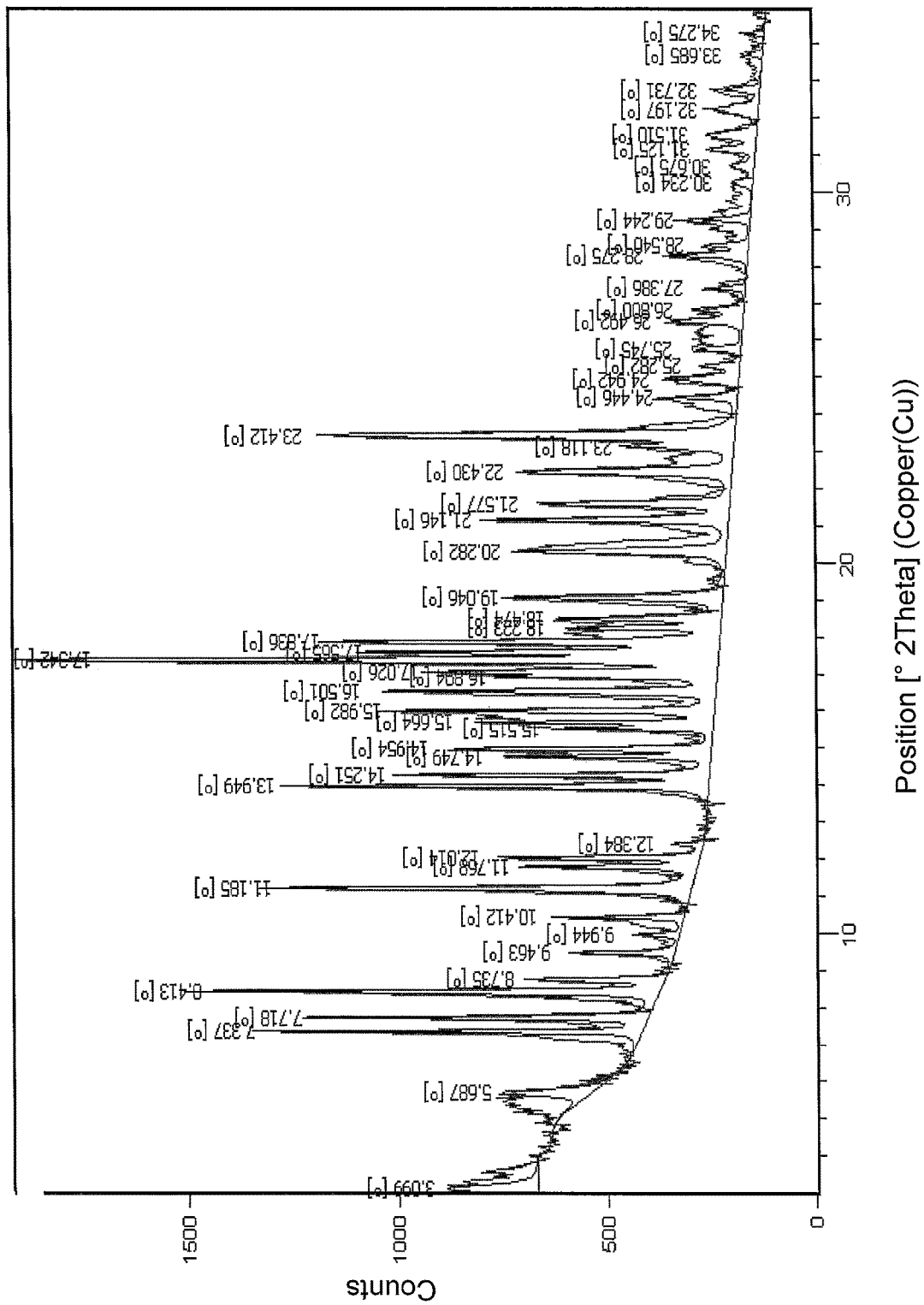
FIG. 24 shows the X-ray powder diffractogram of crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine with peaks numerically identified.

One embodiment provides a composition wherein the crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the X-ray powder diffraction pattern as shown in FIG. 24.

Provided herein is a composition comprising crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine characterized by an X-ray diffraction pattern reflection at a 2 theta value of 17.3.

One embodiment provides a composition wherein the crystalline Form L is further characterized by X-ray diffraction pattern reflections at 2 theta values of 7.3, 7.7, 8.4, 11.2, 13.9, 17.8 and 23.4.

One embodiment provides a composition wherein the crystalline Form L is further characterized by X-ray diffraction pattern reflections at 2 theta values of 5.7, 8.7, 12.0, 14.3, 16.0, 16.5, 17.6, 17.8, 19.0, 20.3, 21.1 and 22.4.

One embodiment provides a composition wherein the crystalline Form L is further characterized by at least one X-ray diffraction pattern reflection selected from a 2 theta value of 5.7, 7.3, 7.7, 8.4, 8.7, 11.2, 12.0, 13.9, 14.3, 16.0, 16.5, 17.3, 17.6, 17.8, 19.0, 20.3, 21.1, 23.4 and 22.4.

One embodiment provides a composition wherein the crystalline Form L is further characterized by at least two X-ray diffraction pattern reflections selected from a 2 theta value of 5.7, 7.3, 7.7, 8.4, 8.7, 11.2, 12.0, 13.9, 14.3, 16.0, 16.5, 17.3, 17.6, 17.8, 19.0, 20.3, 21.1, 23.4 and 22.4.

One embodiment provides a composition wherein the crystalline Form L is further characterized by at least three X-ray diffraction pattern reflections selected from a 2 theta value of 5.7, 7.3, 7.7, 8.4, 8.7, 11.2, 12.0, 13.9, 14.3, 16.0, 16.5, 17.3, 17.6, 17.8, 19.0, 20.3, 21.1, 23.4 and 22.4.

One embodiment provides a composition wherein the crystalline Form L is further characterized by at least four X-ray diffraction pattern reflections selected from a 2 theta value of 5.7, 7.3, 7.7, 8.4, 8.7, 11.2, 12.0, 13.9, 14.3, 16.0, 16.5, 17.3, 17.6, 17.8, 19.0, 20.3, 21.1, 23.4 and 22.4.

One embodiment provides a composition wherein the crystalline Form L is further characterized by at least five X-ray diffraction pattern reflections selected from a 2 theta value of 5.7, 7.3, 7.7, 8.4, 8.7, 11.2, 12.0, 13.9, 14.3, 16.0, 16.5, 17.3, 17.6, 17.8, 19.0, 20.3, 21.1, 23.4 and 22.4.

One embodiment provides a composition wherein the crystalline Form L is further characterized by at least six X-ray diffraction pattern reflections selected from a 2 theta value of 5.7, 7.3, 7.7, 8.4, 8.7, 11.2, 12.0, 13.9, 14.3, 16.0, 16.5, 17.3, 17.6, 17.8, 19.0, 20.3, 21.1, 23.4 and 22.4.

Figure 26:
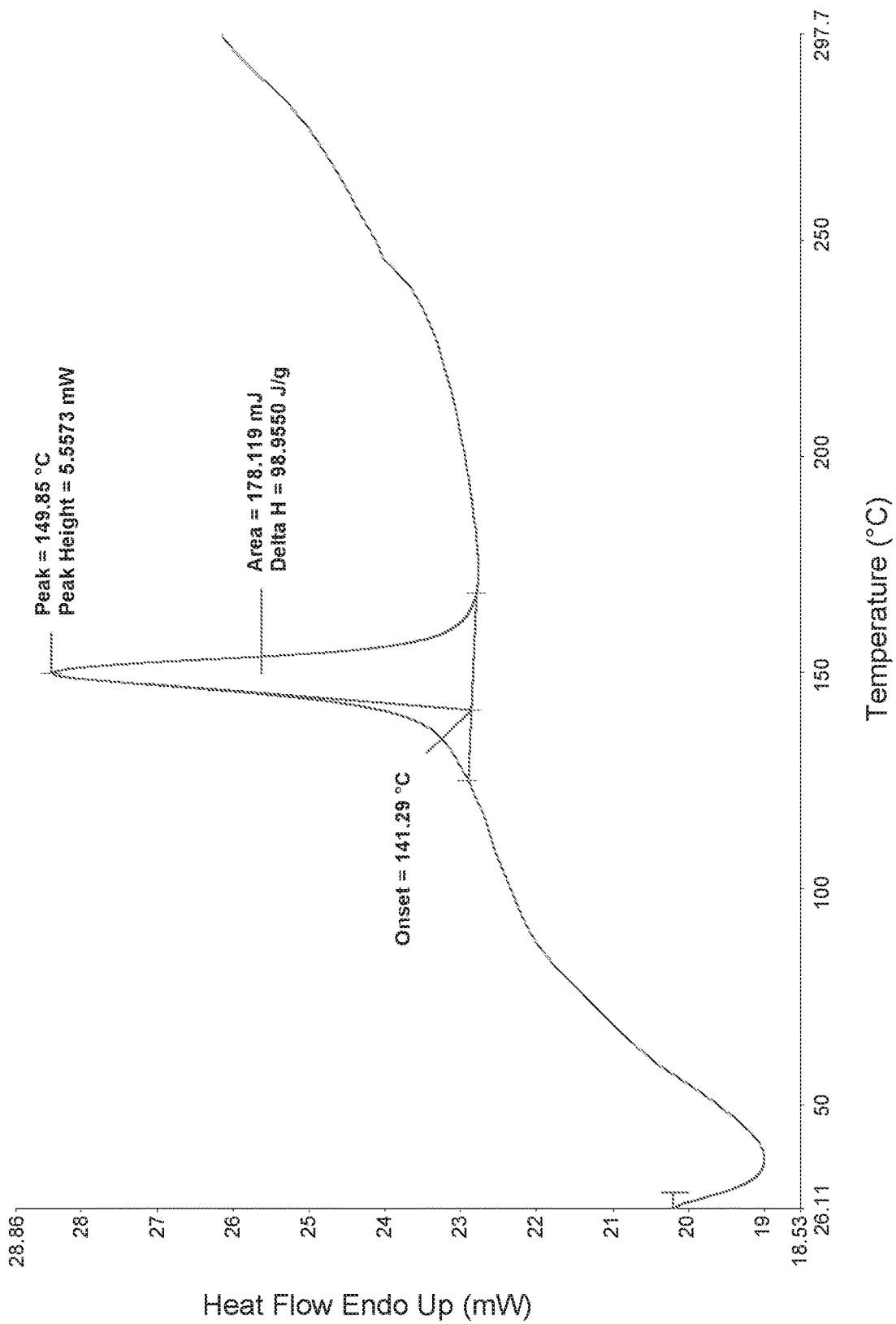
FIG. 26 shows the differential scanning calorimetry thermogram of crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the differential scanning calorimetry pattern as shown in FIG. 26.

Figure 27:
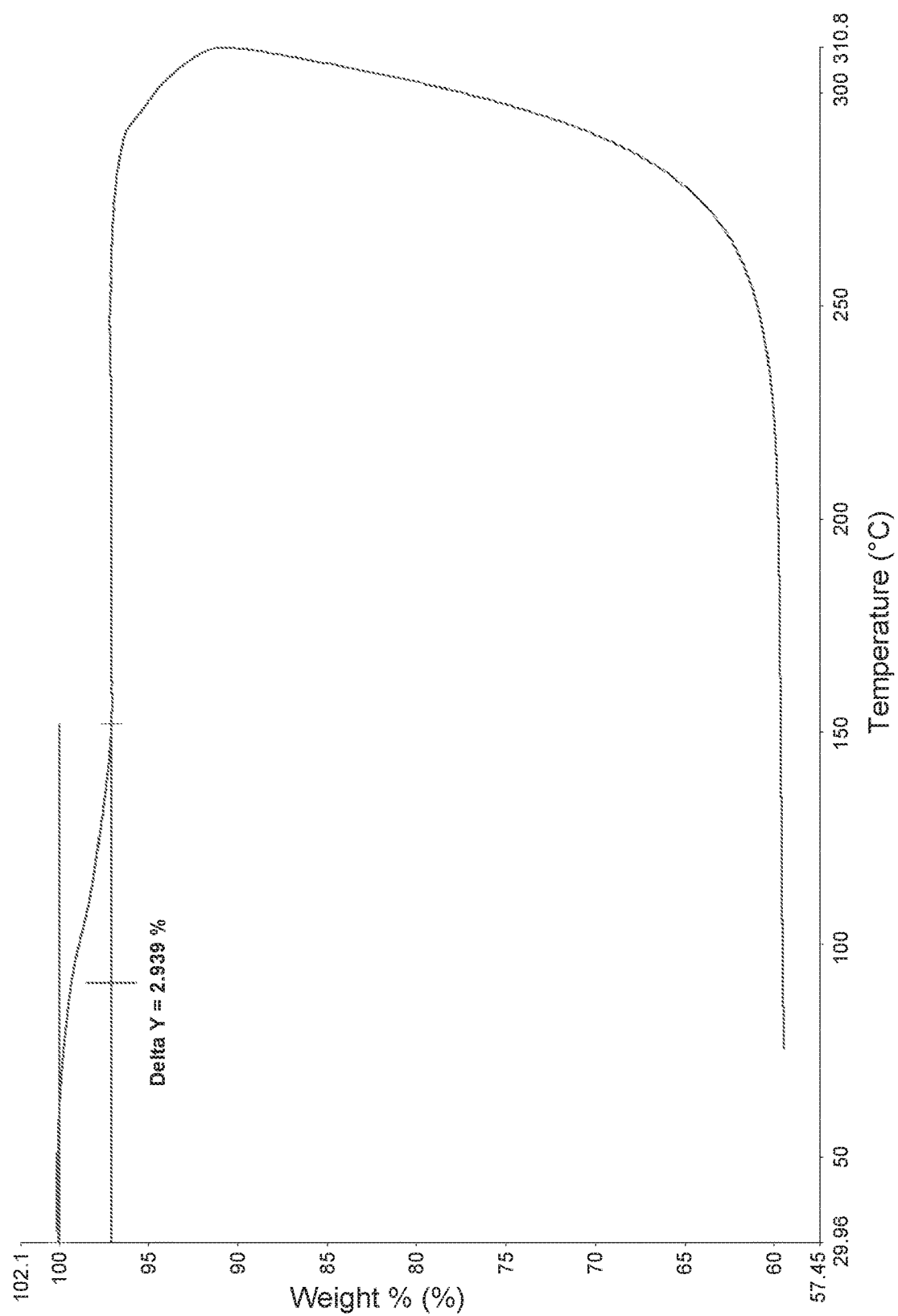
FIG. 27 shows the thermal gravimetric analysis thermogram of crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the thermogravimetric analysis pattern as shown in FIG. 27.

Figure 28:
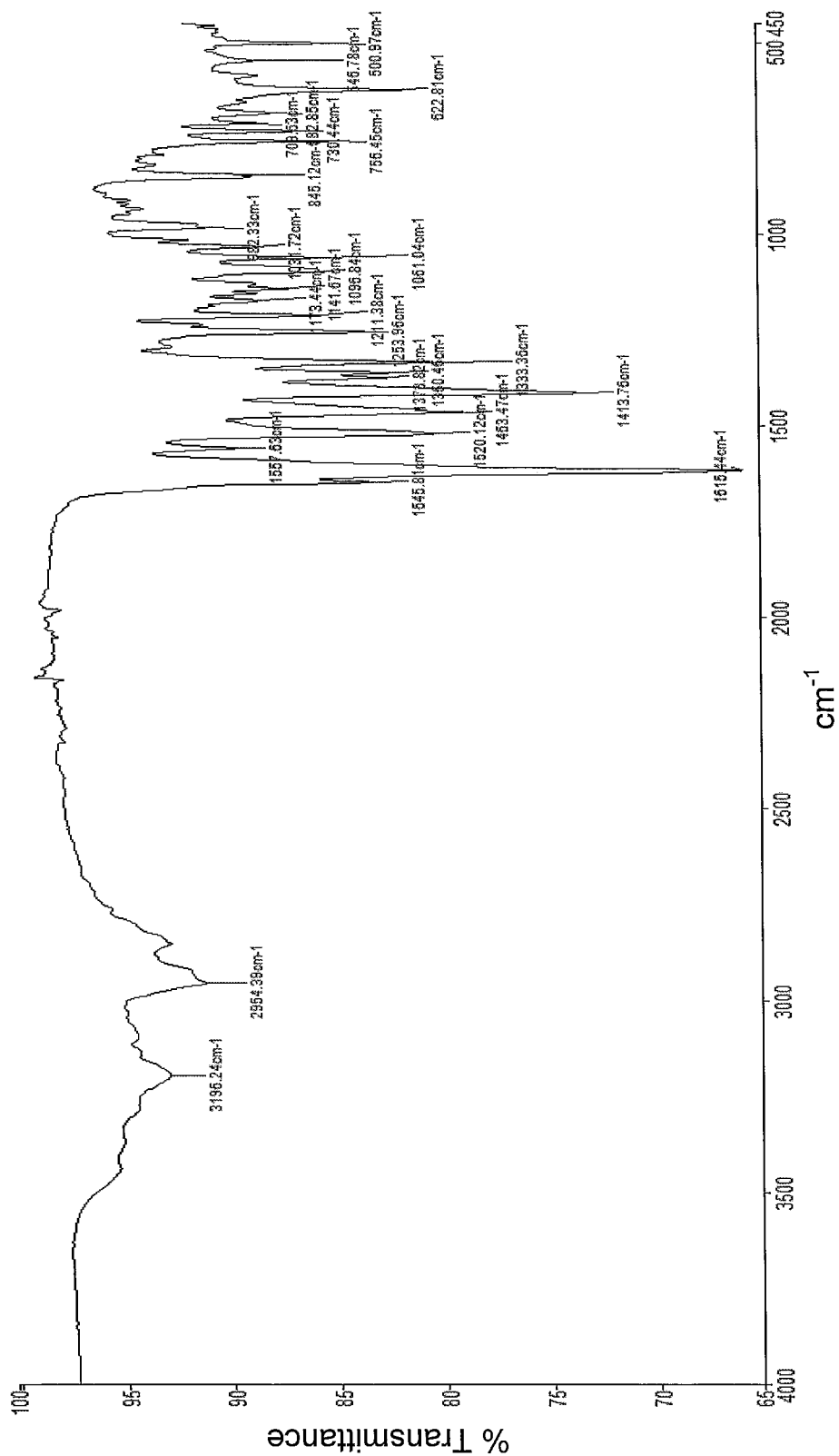
FIG. 28 shows the infrared spectrum of crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the infrared spectrum as shown in FIG. 28.

Provided herein is the crystalline solid Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Figure 31:
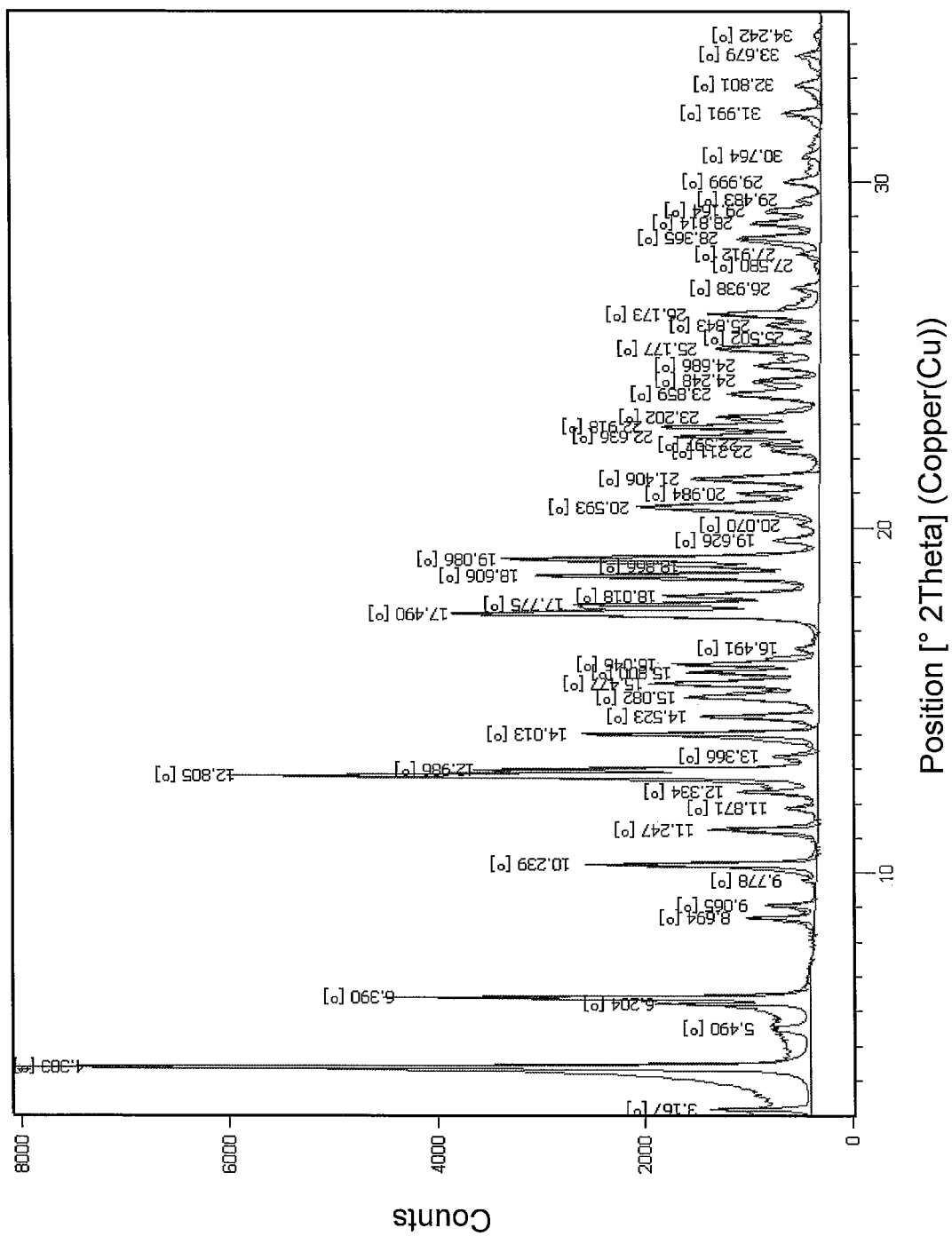
FIG. 31 shows the X-ray powder diffractogram of crystalline Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine with peaks numerically identified.

One embodiment provides a composition wherein the crystalline Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the X-ray powder diffraction pattern as shown in FIG. 31.

Provided herein is a composition comprising crystalline hydrate Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine characterized by an X-ray diffraction pattern reflection at a 2 theta value of 4.4.

One embodiment provides a composition wherein the crystalline Form G is further characterized by X-ray diffraction pattern reflections at 2 theta values of 6.4, 10.2, 12.8, 13.0, 14.0, 17.5, 17.8, 18.6, and 19.1.

One embodiment provides a composition wherein the crystalline Form G is further characterized by X-ray diffraction pattern reflections at 2 theta values of 6.2, 11.2, 14.5, 15.5, 16.0, 18.0, 20.6, 22.6, 22.9, and 28.4.

One embodiment provides a composition wherein the crystalline Form G is further characterized by at least one X-ray diffraction pattern reflection selected from a 2 theta value of 4.4, 6.2, 6.4, 10.2, 11.2, 12.8, 13.0, 14.0, 14.5, 15.5, 16.0, 17.5, 17.8, 18.0, 18.6, 19.1, 20.6, 22.6, 22.9, and 28.4.

One embodiment provides a composition wherein the crystalline Form G is further characterized by at least two X-ray diffraction pattern reflection selected from a 2 theta value of 4.4, 6.2, 6.4, 10.2, 11.2, 12.8, 13.0, 14.0, 14.5, 15.5, 16.0, 17.5, 17.8, 18.0, 18.6, 19.1, 20.6, 22.6, 22.9, and 28.4.

One embodiment provides a composition wherein the crystalline Form G is further characterized by at least three X-ray diffraction pattern reflection selected from a 2 theta value of 4.4, 6.2, 6.4, 10.2, 11.2, 12.8, 13.0, 14.0, 14.5, 15.5, 16.0, 17.5, 17.8, 18.0, 18.6, 19.1, 20.6, 22.6, 22.9, and 28.4.

One embodiment provides a composition wherein the crystalline Form G is further characterized by at least four X-ray diffraction pattern reflection selected from a 2 theta value of 4.4, 6.2, 6.4, 10.2, 11.2, 12.8, 13.0, 14.0, 14.5, 15.5, 16.0, 17.5, 17.8, 18.0, 18.6, 19.1, 20.6, 22.6, 22.9, and 28.4.

One embodiment provides a composition wherein the crystalline Form G is further characterized by at least five X-ray diffraction pattern reflection selected from a 2 theta value of 4.4, 6.2, 6.4, 10.2, 11.2, 12.8, 13.0, 14.0, 14.5, 15.5, 16.0, 17.5, 17.8, 18.0, 18.6, 19.1, 20.6, 22.6, 22.9, and 28.4.

One embodiment provides a composition wherein the crystalline Form G is further characterized by at least six X-ray diffraction pattern reflection selected from a 2 theta value of 4.4, 6.2, 6.4, 10.2, 11.2, 12.8, 13.0, 14.0, 14.5, 15.5, 16.0, 17.5, 17.8, 18.0, 18.6, 19.1, 20.6, 22.6, 22.9, and 28.4.

Figure 33:
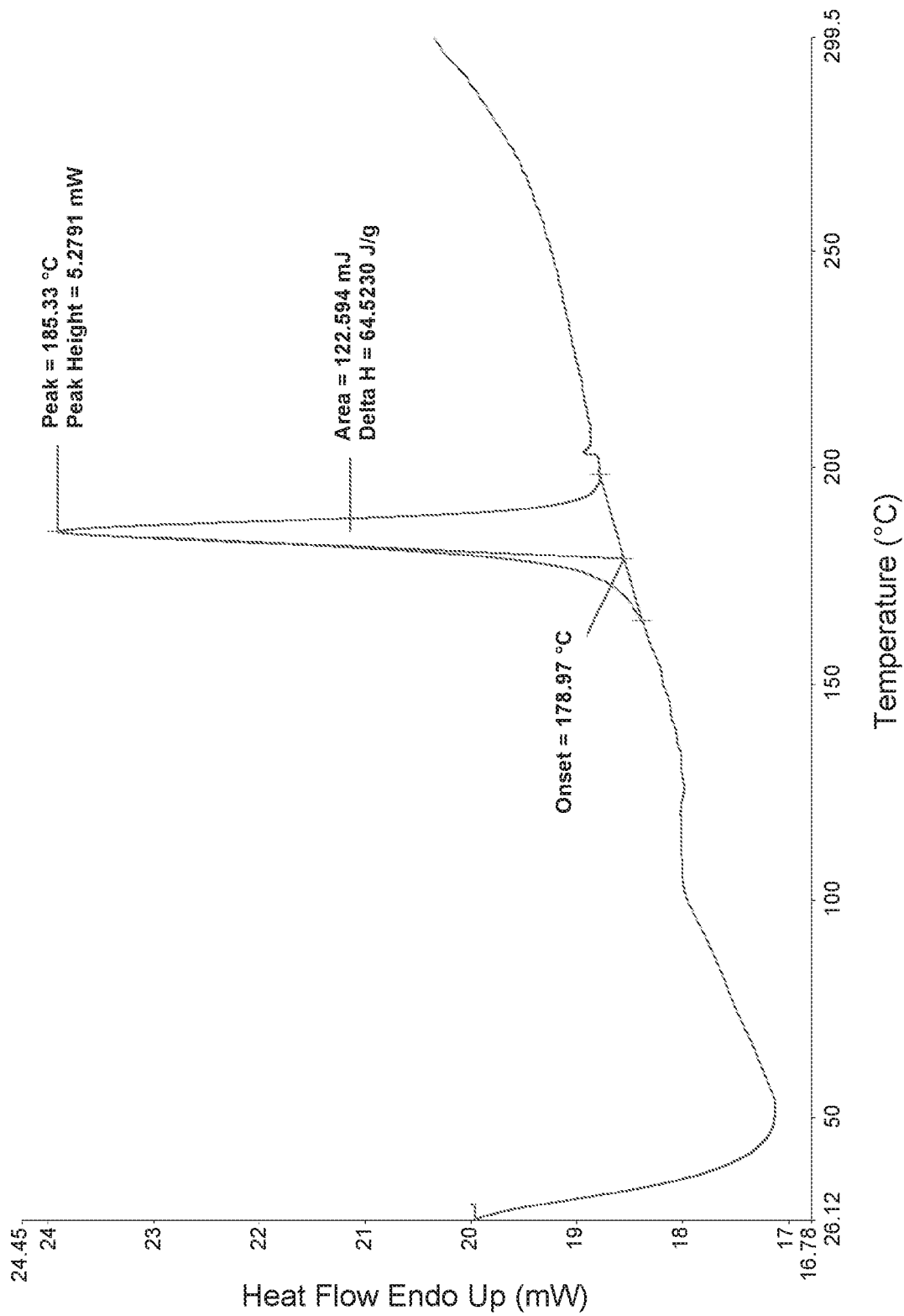
FIG. 33 shows the differential scanning calorimetry thermogram of crystalline Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the differential scanning calorimetry pattern as shown in FIG. 33.

Figure 34:
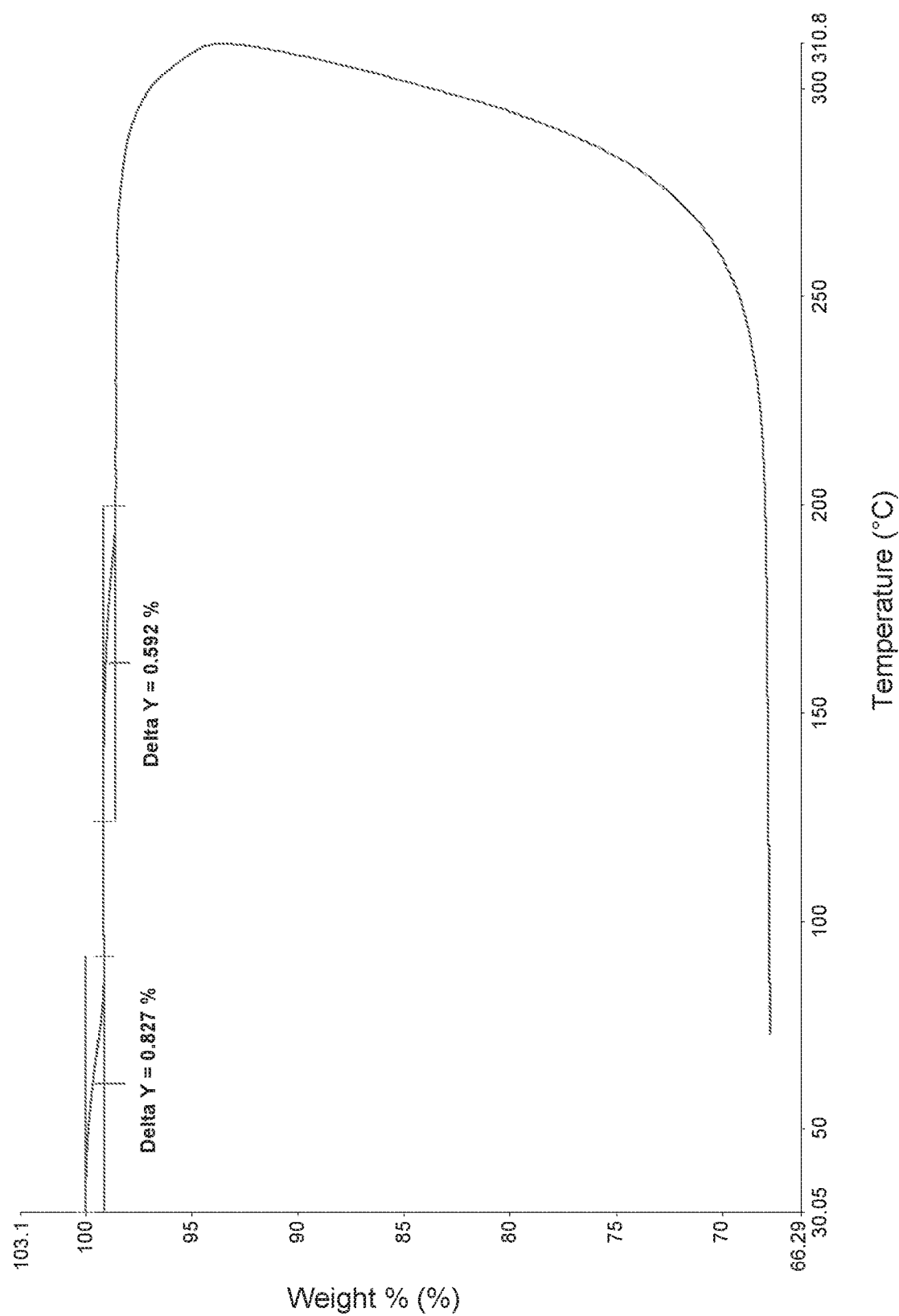
FIG. 34 shows the thermal gravimetric analysis thermogram of crystalline Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the thermogravimetric analysis pattern as shown in FIG. 34.

Provided herein is the crystalline solid Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Figure 35:
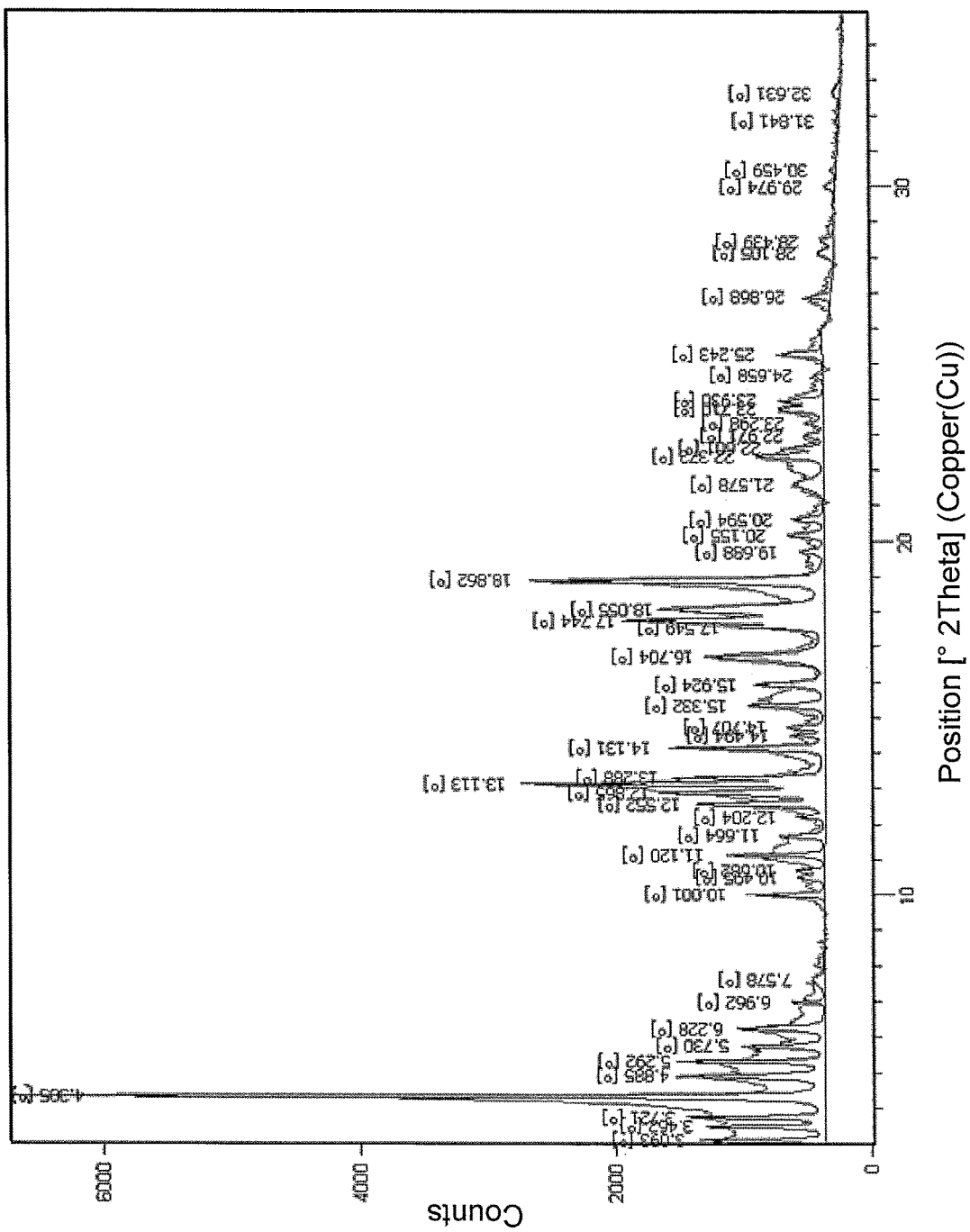
FIG. 35 shows the X-ray powder diffractogram of crystalline Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine with peaks numerically identified.

One embodiment provides a composition wherein the crystalline Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the X-ray powder diffraction pattern as shown in FIG. 35.

Provided herein is a composition comprising crystalline Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine characterized by an X-ray diffraction pattern reflection at a 2 theta value of 4.4.

One embodiment provides a composition wherein the crystalline Form H is further characterized by X-ray diffraction pattern reflections at 2 theta values of 12.6, 12.9, 13.1, 14.1, 16.7, 17.7, 18.1, and 18.9.

One embodiment provides a composition wherein the crystalline Form H is further characterized by X-ray diffraction pattern reflections at 2 theta values of 3.1, 3.7, 4.9, 5.3, 10.0, 11.1, 13.3, 15.3, 17.5, 22.3, and 25.2.

One embodiment provides a composition wherein the crystalline Form H is further characterized by at least one X-ray diffraction pattern reflection selected from a 2 theta value of 3.1, 3.7, 4.4, 4.9, 5.3, 10.0, 11.1, 12.6, 12.9, 13.1, 13.3, 14.1, 15.3, 16.7, 17.5, 17.7, 18.1, 18.9, 22.3, and 25.2.

One embodiment provides a composition wherein the crystalline Form H is further characterized by at least two X-ray diffraction pattern reflection selected from a 2 theta value of 3.1, 3.7, 4.4, 4.9, 5.3, 10.0, 11.1, 12.6, 12.9, 13.1, 13.3, 14.1, 15.3, 16.7, 17.5, 17.7, 18.1, 18.9, 22.3, and 25.2.

One embodiment provides a composition wherein the crystalline Form H is further characterized by at least three X-ray diffraction pattern reflection selected from a 2 theta value of 3.1, 3.7, 4.4, 4.9, 5.3, 10.0, 11.1, 12.6, 12.9, 13.1, 13.3, 14.1, 15.3, 16.7, 17.5, 17.7, 18.1, 18.9, 22.3, and 25.2.

One embodiment provides a composition wherein the crystalline Form H is further characterized by at least four X-ray diffraction pattern reflection selected from a 2 theta value of 3.1, 3.7, 4.4, 4.9, 5.3, 10.0, 11.1, 12.6, 12.9, 13.1, 13.3, 14.1, 15.3, 16.7, 17.5, 17.7, 18.1, 18.9, 22.3, and 25.2.

One embodiment provides a composition wherein the crystalline Form H is further characterized by at least five X-ray diffraction pattern reflection selected from a 2 theta value of 3.1, 3.7, 4.4, 4.9, 5.3, 10.0, 11.1, 12.6, 12.9, 13.1, 13.3, 14.1, 15.3, 16.7, 17.5, 17.7, 18.1, 18.9, 22.3, and 25.2.

One embodiment provides a composition wherein the crystalline Form H is further characterized by at least six X-ray diffraction pattern reflection selected from a 2 theta value of 3.1, 3.7, 4.4, 4.9, 5.3, 10.0, 11.1, 12.6, 12.9, 13.1, 13.3, 14.1, 15.3, 16.7, 17.5, 17.7, 18.1, 18.9, 22.3, and 25.2.

Figure 37:
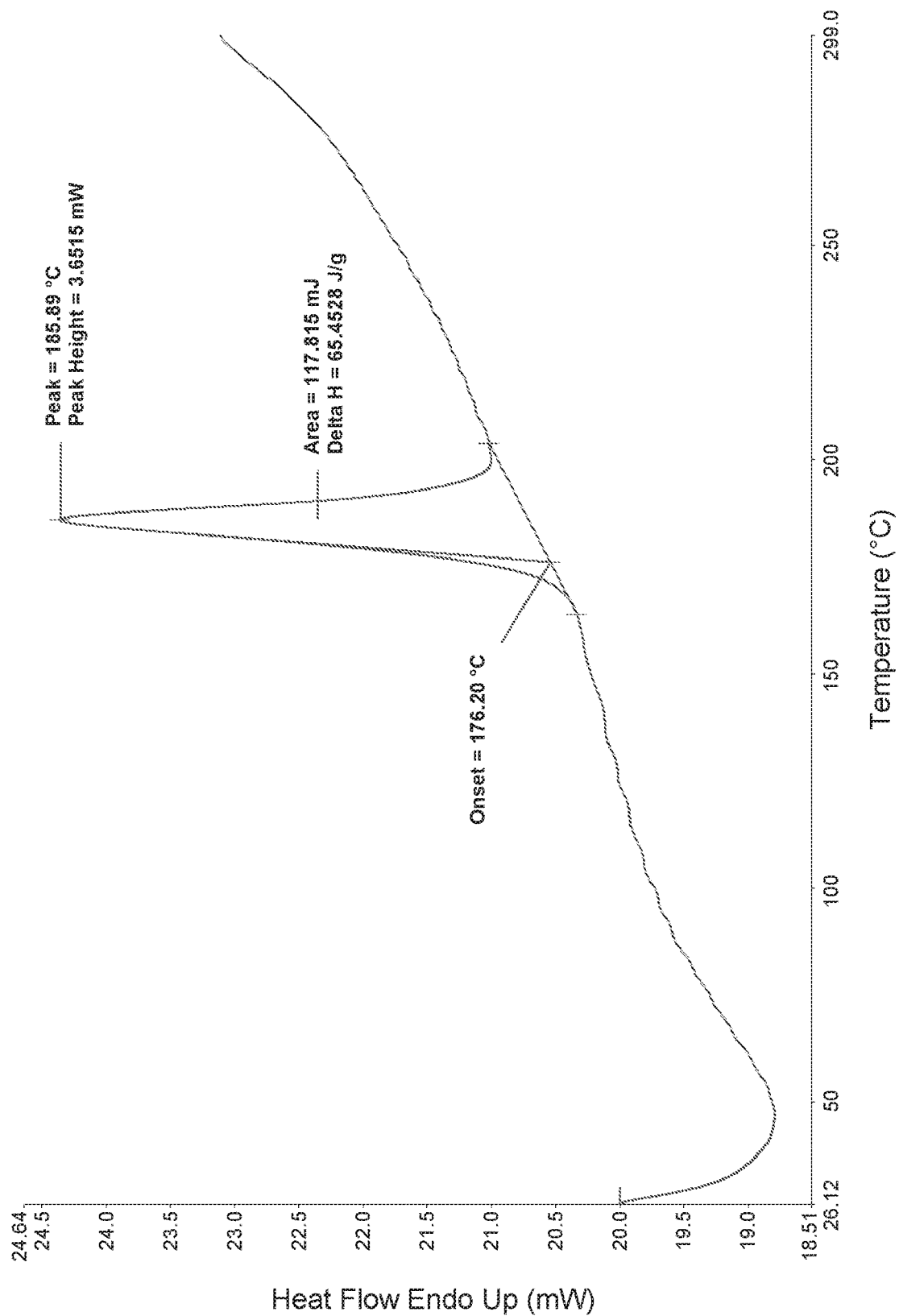
FIG. 37 shows the differential scanning calorimetry thermogram of crystalline Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the differential scanning calorimetry pattern as shown in FIG. 37.

Figure 38:
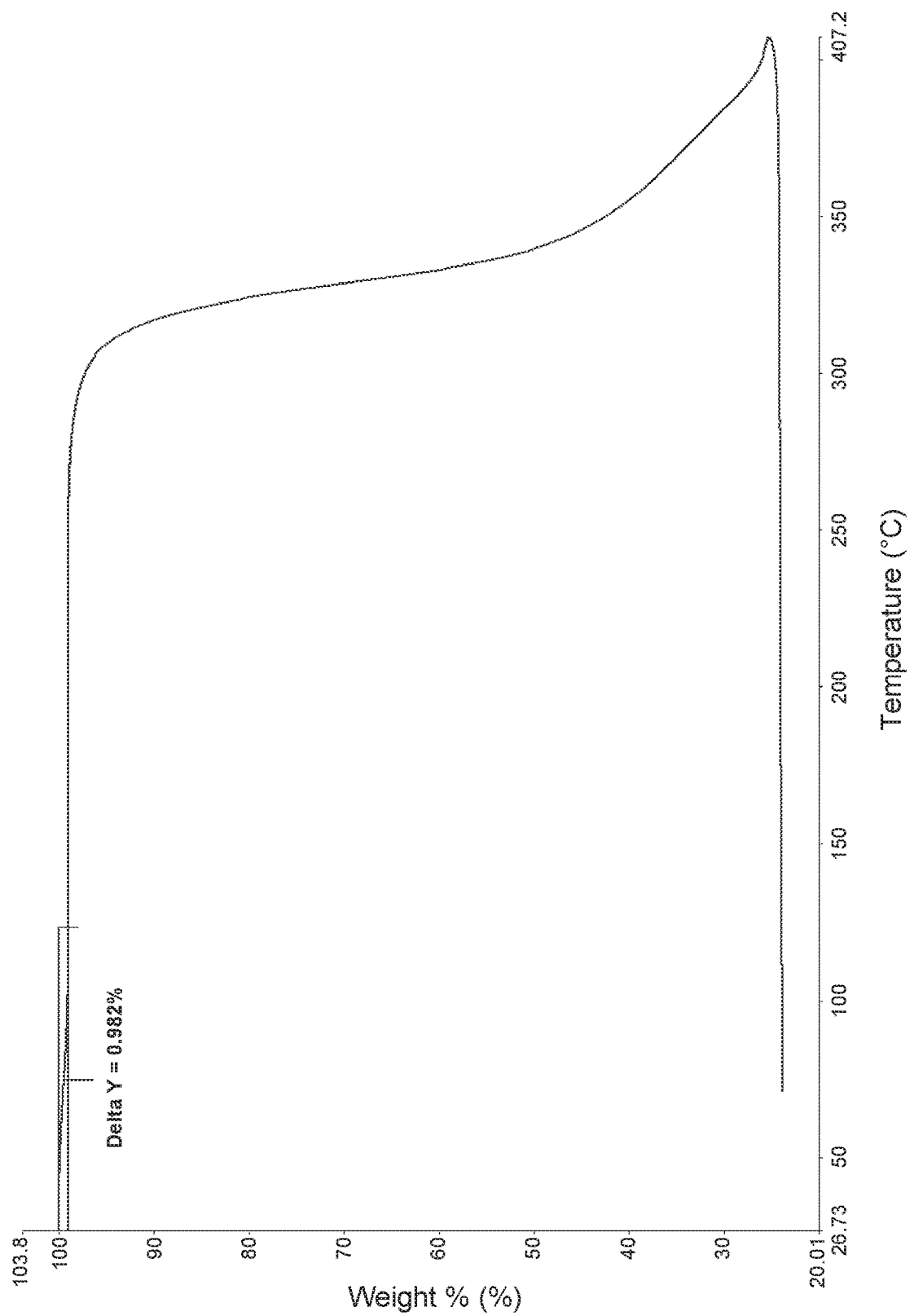
FIG. 38 shows the thermal gravimetric analysis thermogram of crystalline Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the thermogravimetric analysis pattern as shown in FIG. 38.

Provided herein is the crystalline solid Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Figure 39:
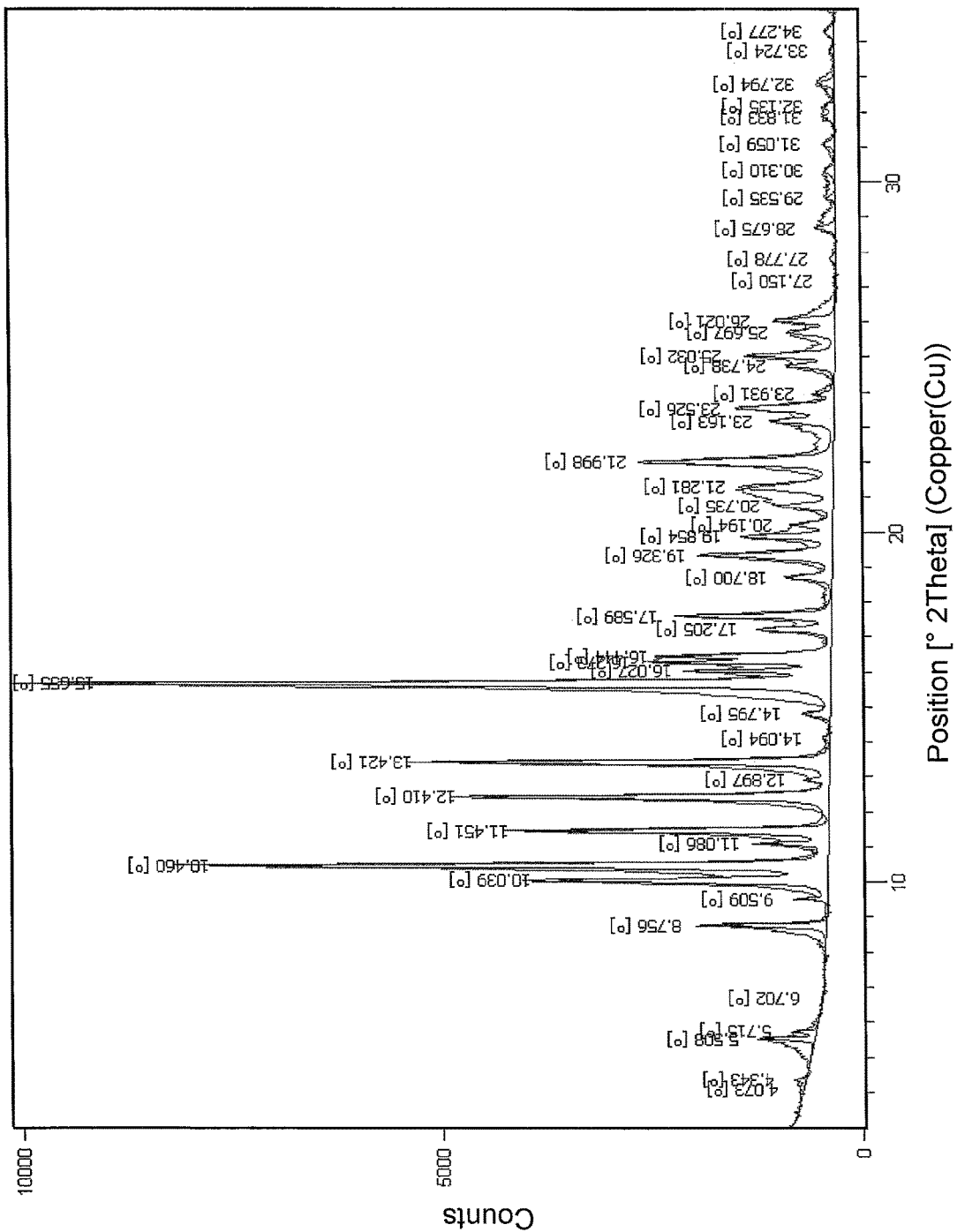
FIG. 39 shows the X-ray powder diffractogram of crystalline Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine with peaks numerically identified.

One embodiment provides a composition wherein the crystalline Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the X-ray powder diffraction pattern as shown in FIG. 39.

Provided herein is a composition comprising crystalline Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine characterized by an X-ray diffraction pattern reflection at a 2 theta value of 15.7.

One embodiment provides a composition wherein the crystalline Form I is further characterized by X-ray diffraction pattern reflections at 2 theta values of 8.8, 10.0, 10.5, 11.5, 12.4, 13.4, 16.3, 16.4, 17.6, and 22.0.

One embodiment provides a composition wherein the crystalline Form I is further characterized by X-ray diffraction pattern reflections at 2 theta values of 5.5, 11.0, 17.2, 19.3, 19.9, 21.3, 23.1, 23.5, and 25.0.

One embodiment provides a composition wherein the crystalline Form I is further characterized by at least one X-ray diffraction pattern reflection selected from a 2 theta value of 5.5, 8.8, 10.0, 10.5, 11.0, 11.5, 12.4, 13.4, 15.7, 16.3, 16.4, 17.2, 17.6, 19.3, 19.9, 21.3, 22.0, 23.1, 23.5, and 25.0.

One embodiment provides a composition wherein the crystalline Form I is further characterized by at least two X-ray diffraction pattern reflection selected from a 2 theta value of 5.5, 8.8, 10.0, 10.5, 11.0, 11.5, 12.4, 13.4, 15.7, 16.3, 16.4, 17.2, 17.6, 19.3, 19.9, 21.3, 22.0, 23.1, 23.5, and 25.0.

One embodiment provides a composition wherein the crystalline Form I is further characterized by at least three X-ray diffraction pattern reflection selected from a 2 theta value of 5.5, 8.8, 10.0, 10.5, 11.0, 11.5, 12.4, 13.4, 15.7, 16.3, 16.4, 17.2, 17.6, 19.3, 19.9, 21.3, 22.0, 23.1, 23.5, and 25.0.

One embodiment provides a composition wherein the crystalline Form I is further characterized by at least four X-ray diffraction pattern reflection selected from a 2 theta value of 5.5, 8.8, 10.0, 10.5, 11.0, 11.5, 12.4, 13.4, 15.7, 16.3, 16.4, 17.2, 17.6, 19.3, 19.9, 21.3, 22.0, 23.1, 23.5, and 25.0.

One embodiment provides a composition wherein the crystalline Form I is further characterized by at least five X-ray diffraction pattern reflection selected from a 2 theta value of 5.5, 8.8, 10.0, 10.5, 11.0, 11.5, 12.4, 13.4, 15.7, 16.3, 16.4, 17.2, 17.6, 19.3, 19.9, 21.3, 22.0, 23.1, 23.5, and 25.0.

One embodiment provides a composition wherein the crystalline Form I is further characterized by at least six X-ray diffraction pattern reflection selected from a 2 theta value of 5.5, 8.8, 10.0, 10.5, 11.0, 11.5, 12.4, 13.4, 15.7, 16.3, 16.4, 17.2, 17.6, 19.3, 19.9, 21.3, 22.0, 23.1, 23.5, and 25.0.

Figure 41:
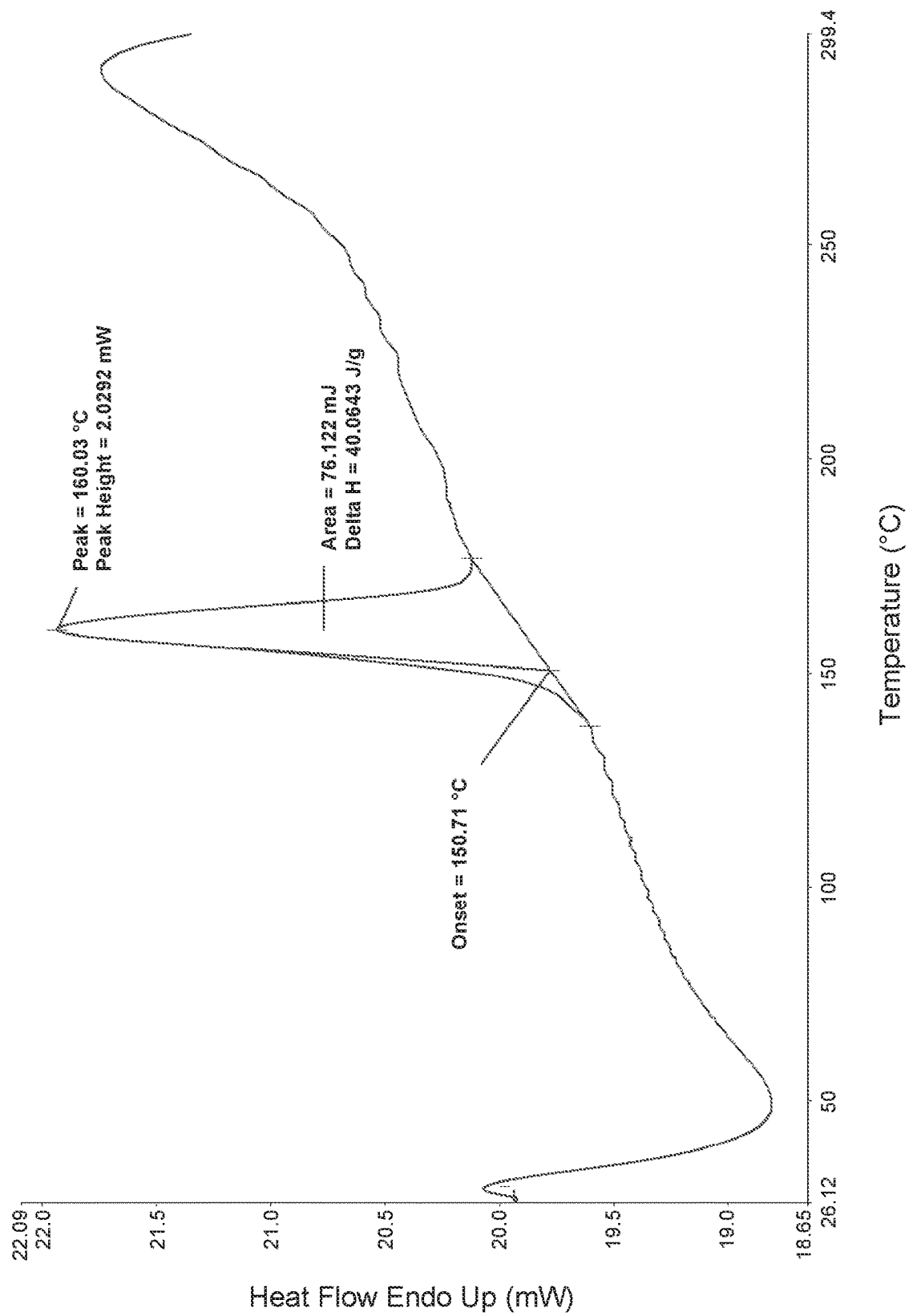
FIG. 41 shows the differential scanning calorimetry thermogram of crystalline Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the differential scanning calorimetry pattern as shown in FIG. 41.

Figure 42:
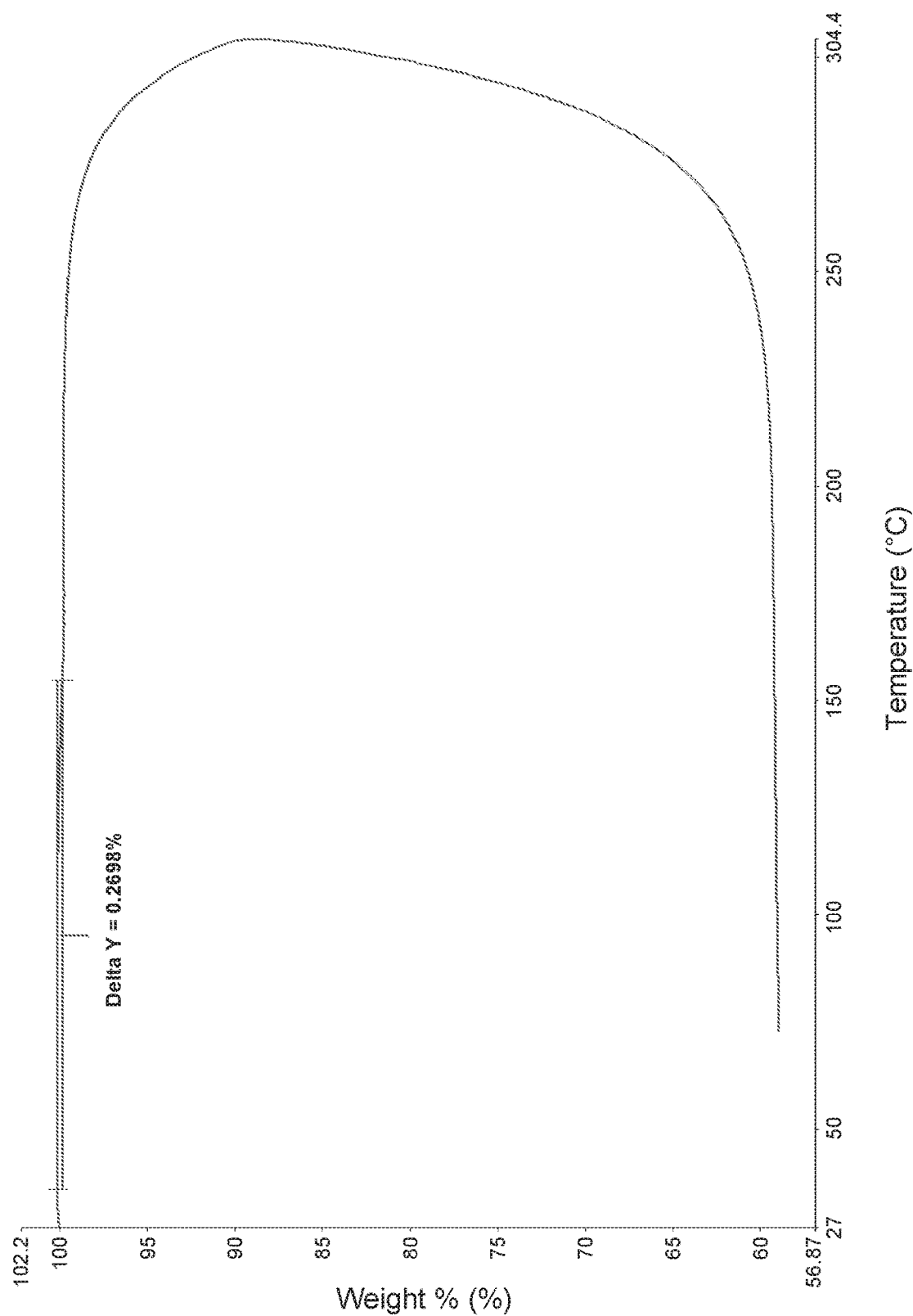
FIG. 42 shows the thermal gravimetric analysis thermogram of crystalline Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

One embodiment provides a composition wherein the crystalline Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the thermogravimetric analysis pattern as shown in FIG. 42.

Provided herein is the maleate salt of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is the fumarate salt of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is the compound 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine or a pharmaceutically acceptable salt, solution or hydrate thereof, free of bis(3-((5-fluoro-2-methylpyrimidin-4-yl)amino)-6,6-dimethyl-4,6-dihydropyrrolo[3,4-c]pyrazol-5(1H)-yl)methanone. Provided herein is the compound 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine or a pharmaceutically acceptable salt, solution or hydrate thereof, essentially free of bis(3-((5-fluoro-2-methylpyrimidin-4-yl)amino)-6,6-dimethyl-4,6-dihydropyrrolo[3,4-c]pyrazol-5(1H)-yl)methanone.

Provided herein is the compound 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine or a pharmaceutically acceptable salt, solution or hydrate thereof, substantially free of bis(3-((5-fluoro-2-methylpyrimidin-4-yl)amino)-6,6-dimethyl-4,6-dihydropyrrolo[3,4-c]pyrazol-5(1H)-yl)methanone. One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 1% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.5% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.4% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.3% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.25% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.20% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.15% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.10% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.08% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.05% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 1% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.5% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.4% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.3% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.25% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.20% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.15% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.10% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.08% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.05% (w/w).

Provided herein is the compound 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine or a pharmaceutically acceptable salt, solution or hydrate thereof, free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate. Provided herein is the compound 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine or a pharmaceutically acceptable salt, solution or hydrate thereof, essentially free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate.

Provided herein is the compound 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine or a pharmaceutically acceptable salt, solution or hydrate thereof, substantially free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate. One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 1% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.5% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.4% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.3% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.25% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.20% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.15% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.10% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.08% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.05% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 1% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine- 1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.5% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.4% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.3% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.25% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.20% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.15% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.10% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.08% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.05% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are not detectable.

Provided herein is the compound 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine or a pharmaceutically acceptable salt, solution or hydrate thereof, free of impurities. In some embodiments, the compound is free of structurally related impurities. Provided herein is the compound 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine or a pharmaceutically acceptable salt, solution or hydrate thereof, essentially free of impurities. In some embodiments, the compound is essentially free of structurally related impurities.

Provided herein is the compound 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine or a pharmaceutically acceptable salt, solution or hydrate thereof, substantially free of impurities. In some embodiments, the compound is substantially free of structurally related impurities. One embodiment provides a composition wherein the amount of impurities is less than 1% (w/w). One embodiment provides a composition wherein the amount of impurities is less than 0.5% (w/w). One embodiment provides a composition wherein the amount of impurities is less than 0.4% (w/w). One embodiment provides a composition wherein the amount of impurities is less than 0.3% (w/w). One embodiment provides a composition wherein the amount of impurities is less than 0.25% (w/w). One embodiment provides a composition wherein the amount of impurities is less than 0.20% (w/w). One embodiment provides a composition wherein the amount of impurities is less than 0.15% (w/w). One embodiment provides a composition wherein the amount of impurities is less than 0.10% (w/w). One embodiment provides a composition wherein the amount of impurities is less than 0.08% (w/w). One embodiment provides a composition wherein the amount of impurities is less than 0.05% (w/w). One embodiment provides a composition wherein the amount of impurities is not more than 1% (w/w). One embodiment provides a composition wherein the amount of impurities is not more than 0.5% (w/w). One embodiment provides a composition wherein the amount of impurities is not more than 0.4% (w/w). One embodiment provides a composition wherein the amount of impurities is not more than 0.3% (w/w). One embodiment provides a composition wherein the amount of impurities is not more than 0.25% (w/w). One embodiment provides a composition wherein the amount of impurities is not more than 0.20% (w/w). One embodiment provides a composition wherein the amount of impurities is not more than 0.15% (w/w). One embodiment provides a composition wherein the amount of impurities is not more than 0.10% (w/w). One embodiment provides a composition wherein the amount of impurities is not more than 0.08% (w/w). One embodiment provides a composition wherein the amount of impurities is not more than 0.05% (w/w). One embodiment provides a composition wherein the amount of impurities is not detectable.

One embodiment provides a composition wherein substantially free means less than about 10% (w/w), less than about 9% (w/w), less than about 8% (w/w), less than about 7% (w/w), less than about 6% (w/w), less than about 5% (w/w), less than about 4.75% (w/w), less than about 4.5% (w/w), less than about 4.25% (w/w), less than about 4% (w/w), less than about 3.75% (w/w), less than about 3.5% (w/w), less than about 3.25% (w/w), less than about 3% (w/w), less than about 2.75% (w/w), less than about 2.5% (w/w), less than about 2.25% (w/w), less than about 2% (w/w), less than about 1.75% (w/w), less than about 1.5% (w/w), less than about 1.25% (w/w), less than about 1% (w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.25% (w/w), less than about 0.20% (w/w), less than about 0.15% (w/w), less than about 0.1% (w/w), less than about 0.08% (w/w), or less than about 0.05% (w/w). One embodiment provides a composition wherein substantially free means an undetectable amount. One embodiment provides a composition wherein substantially free means less than about 5% (w/w), less than about 3% (w/w), less than about 1% (w/w), less than about 0.5% (w/w), or less than about 0.2% (w/w).

Amorphous Solid Form

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of bis(3-((5-fluoro-2-methylpyrimidin-4-yl)amino)-6,6-dimethyl-4,6-dihydropyrrolo[3,4-c]pyrazol-5(1H)-yl)methanone.

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of bis(3-((5-fluoro-2-methylpyrimidin-4-yl)amino)-6,6-dimethyl-4,6-dihydropyrrolo[3,4-c]pyrazol-5(1H)-yl)methanone.

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of bis(3-((5-fluoro-2-methylpyrimidin-4-yl)amino)-6,6-dimethyl-4,6-dihydropyrrolo[3,4-c]pyrazol-5(1H)-yl)methanone. One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 1% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.5% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.4% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.3% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.25% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.20% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.15% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.10% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.08% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.05% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 1% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.5% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.4% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.3% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.25% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.20% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.15% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.10% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.08% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.05% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not detectable.

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate.

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate.

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate. One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 1% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.5% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.4% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.3% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.25% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.20% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.15% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.10% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.08% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.05% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 1% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.5% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.4% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.3% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.25% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.20% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.15% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.10% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.08% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.05% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are not detectable.

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine. Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine. One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 1% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.5% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.4% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.3% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.25% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.20% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.15% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.10% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.08% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.05% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 1% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.5% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.4% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.3% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.25% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.20% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.15% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.10% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.08% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.05% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not detectable.

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine. Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine. One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 1% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.5% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.4% (w/w). One embodiment provides a composition wherein the amount of crystalline hydrate Form B of 5-{[(2S,5R)-2,5-dimethyl-4-(tetrahydro- 2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.3% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.25% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.20% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.15% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.10% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.08% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.05% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 1% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.5% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.4% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.3% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.25% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.20% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.15% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.10% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.08% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.05% (w/w). One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not detectable. One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not detectable in its X-ray diffraction pattern.

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine. Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine. One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 1% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.5% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.4% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.3% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.25% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.20% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.15% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.10% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.08% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.05% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 1% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.5% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.4% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.3% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.25% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.20% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.15% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.10% (w/w). One embodiment provides a composition wherein the amount of crystalline hydrate Form D of 5- {[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.08% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.05% (w/w). One embodiment provides a composition wherein the amount of crystalline hydrate Form D of 5- {[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not detectable. One embodiment provides a composition wherein the amount of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not detectable in its X-ray diffraction pattern.

Provided herein is a composition of the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine wherein the X-ray diffraction pattern has no detectable reflections. One embodiment provides a composition whose X-ray diffraction pattern does not have a reflection at a 2 theta value of 16.3. One embodiment provides a composition whose X-ray diffraction pattern does not have a reflection at a 2 theta value of 17.3. One embodiment provides a composition whose X-ray diffraction pattern does not have a reflection at a 2 theta value of 17.9. One embodiment provides a composition whose X-ray diffraction pattern does not have a reflection at a 2 theta value of 18.1.

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of impurities. In some embodiments, the composition is free of structurally related impurities. Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of impurities. In some embodiments, the composition is essentially free of structurally related impurities.

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of impurities. In some embodiments, the composition is substantially free of structurally related impurities. One embodiment provides a composition wherein the amount of impurities is less than 1% (w/w). One embodiment provides a composition wherein the amount of impurities is less than 0.5% (w/w). One embodiment provides a composition wherein the amount of impurities is less than 0.4% (w/w). One embodiment provides a composition wherein the amount of impurities is less than 0.3% (w/w). One embodiment provides a composition wherein the amount of impurities is less than 0.25% (w/w). One embodiment provides a composition wherein the amount of impurities is less than 0.20% (w/w). One embodiment provides a composition wherein the amount of impurities is less than 0.15% (w/w). One embodiment provides a composition wherein the amount of impurities is less than 0.10% (w/w). One embodiment provides a composition wherein the amount of impurities is less than 0.08% (w/w). One embodiment provides a composition wherein the amount of impurities is less than 0.05% (w/w). One embodiment provides a composition wherein the amount of impurities is not more than 1% (w/w). One embodiment provides a composition wherein the amount of impurities is not more than 0.5% (w/w). One embodiment provides a composition wherein the amount of impurities is not more than 0.4% (w/w). One embodiment provides a composition wherein the amount of impurities is not more than 0.3% (w/w). One embodiment provides a composition wherein the amount of impurities is not more than 0.25% (w/w). One embodiment provides a composition wherein the amount of impurities is not more than 0.20% (w/w). One embodiment provides a composition wherein the amount of impurities is not more than 0.15% (w/w). One embodiment provides a composition wherein the amount of impurities is not more than 0.10% (w/w). One embodiment provides a composition wherein the amount of impurities is not more than 0.08% (w/w). One embodiment provides a composition wherein the amount of impurities is not more than 0.05% (w/w). One embodiment provides a composition wherein the amount of impurities is not detectable.

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of solvent. One embodiment provides a composition wherein the amount of solvent is less than 20% (w/w). One embodiment provides a composition wherein the amount of solvent is less than 15% (w/w). One embodiment provides a composition wherein the amount of solvent is less than 10% (w/w). One embodiment provides a composition wherein the amount of solvent is less than 5% (w/w). One embodiment provides a composition wherein the amount of solvent is not more than 20% (w/w). One embodiment provides a composition wherein the amount of solvent is not more than 15% (w/w). One embodiment provides a composition wherein the amount of solvent is not more than 10% (w/w). One embodiment provides a composition wherein the amount of solvent is not more than 5% (w/w). One embodiment provides a composition wherein the amount of solvent is less than 2.0 equivalents. One embodiment provides a composition wherein the amount of solvent is less than 1.5 equivalents. One embodiment provides a composition wherein the amount of solvent is less than 1.0 equivalent. One embodiment provides a composition wherein the amount of solvent is not more than 2.0 equivalents. One embodiment provides a composition wherein the amount of solvent is not more than 1.5 equivalents. One embodiment provides a composition wherein the amount of solvent is not more than 1.0 equivalent.

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of water. One embodiment provides a composition wherein the amount of water is less than 20% (w/w). One embodiment provides a composition wherein the amount of water is less than 15% (w/w). One embodiment provides a composition wherein the amount of water is less than 10% (w/w). One embodiment provides a composition wherein the amount of water is less than 7.5% (w/w). One embodiment provides a composition wherein the amount of water is less than 7.0% (w/w). One embodiment provides a composition wherein the amount of water is less than 6.5% (w/w). One embodiment provides a composition wherein the amount of water is less than 6.0% (w/w). One embodiment provides a composition wherein the amount of water is less than 5.5% (w/w). One embodiment provides a composition wherein the amount of water is less than 5.0% (w/w). One embodiment provides a composition wherein the amount of water is not more than 20% (w/w). One embodiment provides a composition wherein the amount of water is not more than 15% (w/w). One embodiment provides a composition wherein the amount of water is not more than 10% (w/w). One embodiment provides a composition wherein the amount of water is not more than 7.5% (w/w). One embodiment provides a composition wherein the amount of water is not more than 7.0% (w/w). One embodiment provides a composition wherein the amount of water is not more than 6.5% (w/w). One embodiment provides a composition wherein the amount of water is not more than 6.0% (w/w). One embodiment provides a composition wherein the amount of water is not more than 5.5% (w/w). One embodiment provides a composition wherein the amount of water is not more than 5.0% (w/w). One embodiment provides a composition wherein the amount of water is less than 2.0 equivalents. One embodiment provides a composition wherein the amount of water is less than 1.5 equivalents. One embodiment provides a composition wherein the amount of water is less than 1.0 equivalent. One embodiment provides a composition wherein the amount of water is not more than 2.0 equivalents. One embodiment provides a composition wherein the amount of water is not more than 1.5 equivalents. One embodiment provides a composition wherein the amount of water is not more than 1.0 equivalent.

Provided herein is a composition wherein the amorphous solid form of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine comprises a small amount of water. One embodiment provides a composition wherein the amount of water is from 1.5% (w/w) to 7.0% (w/w) of water.

One embodiment provides a composition wherein the amount of water is from 2.0% (w/w) to 6.0% (w/w One embodiment provides a composition wherein the amount of water is from 2.2% (w/w) to 5.9% (w/w). One embodiment provides a composition wherein the amount of water is from 2.4% (w/w) to 5.8% (w/w). One embodiment provides a composition wherein the amount of water is from 2.5% (w/w) to 5.7% (w/w). One embodiment provides a composition wherein the amount of water is from 2.7% (w/w) to 5.5% (w/w). One embodiment provides a composition wherein the amount of water is from 0.25 equivalents to 3.0 equivalents. One embodiment provides a composition wherein the amount of water is from 0.5 equivalents to 2.5 equivalents. One embodiment provides a composition wherein the amount of water is from 0.75 equivalents to 2.25 equivalents. One embodiment provides a composition wherein the amount of water is from 1.0 equivalent to 2.0 equivalents.

Crystalline Hydrate Form B

Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of bis(3-((5-fluoro-2-methylpyrimidin-4-yl)amino)-6,6-dimethyl-4,6-dihydropyrrolo[3,4-c]pyrazol-5(1H)-yl)methanone.

Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of bis(3-((5-fluoro-2-methylpyrimidin-4-yl)amino)-6,6-dimethyl-4,6-dihydropyrrolo[3,4-c]pyrazol-5(1H)-yl)methanone.

Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of bis(3-((5-fluoro-2-methylpyrimidin-4-yl)amino)-6,6-dimethyl-4,6-dihydropyrrolo[3,4-c]pyrazol-5(1H)-yl)methanone. One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 1% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.5% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.4% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.3% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.25% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.20% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.15% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.10% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.08% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.05% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 1% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.5% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.4% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.3% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.25% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.20% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.15% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.10% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.08% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.05% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not detectable.

Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate.

Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate.

Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate. One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 1% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.5% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.4% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.3% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.25% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.20% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.15% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.10% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.08% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.05% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 1% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.5% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.4% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.3% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.25% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.20% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.15% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.10% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.08% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.05% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are not detectable.

Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine. Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine. One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 1% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.5% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.4% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.3% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.25% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.20% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.15% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.10% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.08% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.05% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 1% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.5% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.4% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.3% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.25% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.20% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.15% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.10% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.08% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.05% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not detectable.

Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine. Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine. One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 1% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.5% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.4% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.3% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.25% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.20% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.15% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.10% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.08% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.05% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 1% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.5% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.4% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.3% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.25% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.20% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.15% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.10% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.08% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.05% (w/w). One embodiment provides a composition wherein the amount of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not detectable.

Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of impurities. In some embodiments, the composition is free of structurally related impurities. Provided herein is a composition wherein crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of impurities. In some embodiments, the composition is essentially free of structurally related impurities.

Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of impurities. In some embodiments, the composition is substantially free of structurally related impurities. One embodiment provides a composition wherein the amount of impurities is less than 1% (w/w). One embodiment provides a composition wherein the amount of impurities is less than 0.5% (w/w). One embodiment provides a composition wherein the amount of impurities is less than 0.4% (w/w). One embodiment provides a composition wherein the amount of impurities is less than 0.3% (w/w). One embodiment provides a composition wherein the amount of impurities is less than 0.25% (w/w). One embodiment provides a composition wherein the amount of impurities is less than 0.20% (w/w). One embodiment provides a composition wherein the amount of impurities is less than 0.15% (w/w). One embodiment provides a composition wherein the amount of impurities is less than 0.10% (w/w). One embodiment provides a composition wherein the amount of impurities is less than 0.08% (w/w). One embodiment provides a composition wherein the amount of impurities is less than 0.05% (w/w). One embodiment provides a composition wherein the amount of impurities is not more than 1% (w/w). One embodiment provides a composition wherein the amount of impurities is not more than 0.5% (w/w). One embodiment provides a composition wherein the amount of impurities is not more than 0.4% (w/w). One embodiment provides a composition wherein the amount of impurities is not more than 0.3% (w/w). One embodiment provides a composition wherein the amount of impurities is not more than 0.25% (w/w). One embodiment provides a composition wherein the amount of impurities is not more than 0.20% (w/w). One embodiment provides a composition wherein the amount of impurities is not more than 0.15% (w/w). One embodiment provides a composition wherein the amount of impurities is not more than 0.10% (w/w). One embodiment provides a composition wherein the amount of impurities is not more than 0.08% (w/w). One embodiment provides a composition wherein the amount of impurities is not more than 0.05% (w/w). One embodiment provides a composition wherein the amount of impurities is not detectable.

Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of solvent. One embodiment provides a composition wherein the amount of solvent is less than 20% (w/w). One embodiment provides a composition wherein the amount of solvent is less than 15% (w/w). One embodiment provides a composition wherein the amount of solvent is less than 10% (w/w). One embodiment provides a composition wherein the amount of solvent is less than 5% (w/w). One embodiment provides a composition wherein the amount of solvent is not more than 20% (w/w). One embodiment provides a composition wherein the amount of solvent is not more than 15% (w/w). One embodiment provides a composition wherein the amount of solvent is not more than 10% (w/w). One embodiment provides a composition wherein the amount of solvent is not more than 5% (w/w). One embodiment provides a composition wherein the amount of solvent is less than 2.0 equivalents. One embodiment provides a composition wherein the amount of solvent is less than 1.5 equivalents. One embodiment provides a composition wherein the amount of solvent is less than 1.0 equivalent. One embodiment provides a composition wherein the amount of solvent is not more than 2.0 equivalents. One embodiment provides a composition wherein the amount of solvent is not more than 1.5 equivalents. One embodiment provides a composition wherein the amount of solvent is not more than 1.0 equivalent.

Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of water. One embodiment provides a composition wherein the amount of water is less than 20% (w/w). One embodiment provides a composition wherein the amount of water is less than 15% (w/w). One embodiment provides a composition wherein the amount of water is less than 10% (w/w). One embodiment provides a composition wherein the amount of water is less than 7.5% (w/w). One embodiment provides a composition wherein the amount of water is less than 7.0% (w/w). One embodiment provides a composition wherein the amount of water is less than 6.5% (w/w). One embodiment provides a composition wherein the amount of water is less than 6.0% (w/w). One embodiment provides a composition wherein the amount of water is less than 5.5% (w/w). One embodiment provides a composition wherein the amount of water is less than 5.0% (w/w). One embodiment provides a composition wherein the amount of water is not more than 20% (w/w). One embodiment provides a composition wherein the amount of water is not more than 15% (w/w). One embodiment provides a composition wherein the amount of water is not more than 10% (w/w). One embodiment provides a composition wherein the amount of water is not more than 7.5% (w/w). One embodiment provides a composition wherein the amount of water is not more than 7.0% (w/w). One embodiment provides a composition wherein the amount of water is not more than 6.5% (w/w). One embodiment provides a composition wherein the amount of water is not more than 6.0% (w/w). One embodiment provides a composition wherein the amount of water is not more than 5.5% (w/w). One embodiment provides a composition wherein the amount of water is not more than 5.0% (w/w). One embodiment provides a composition wherein the amount of water is less than 2.0 equivalents. One embodiment provides a composition wherein the amount of water is less than 1.5 equivalents. One embodiment provides a composition wherein the amount of water is less than 1.0 equivalent. One embodiment provides a composition wherein the amount of water is not more than 2.0 equivalents. One embodiment provides a composition wherein the amount of water is not more than 1.5 equivalents. One embodiment provides a composition wherein the amount of water is not more than 1.0 equivalent.

Crystalline Hydrate Form D

Provided herein is a composition wherein the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of bis(3-((5-fluoro-2-methylpyrimidin-4-yl)amino)-6,6-dimethyl-4,6-dihydropyrrolo[3,4-c]pyrazol-5(1H)-yl)methanone.

Provided herein is a composition wherein the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of bis(3-((5-fluoro-2-methylpyrimidin-4-yl)amino)-6,6-dimethyl-4,6-dihydropyrrolo[3,4-c]pyrazol-5(1H)-yl)methanone.

Provided herein is a composition wherein the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of bis(3 #5-fluoro-2-methylpyrimidin-4-yl)amino)-6,6-dimethyl-4,6-dihydropyrrolo[3,4-c]pyrazol-5(1H)-yl)methanone. One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 1% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.5% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.4% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.3% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.25% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.20% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.15% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.10% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.08% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.05% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 1% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.5% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.4% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.3% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.25% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.20% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.15% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.10% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.08% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.05% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not detectable.

Provided herein is a composition wherein the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate.
Provided herein is a composition wherein the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate.
Provided herein is a composition wherein the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate. One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 1% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.5% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.4% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.3% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.25% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.20% (w/w). One embodiment provides a composition wherein the ethyl 5-((2S,5R)-2,5-dimethyl-4-((tetrahydro-2H-pyran-4-yl)

methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.15% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.10% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.08% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.05% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 1% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.5% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.4% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.3% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.25% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.20% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.15% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.10% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.08% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.05% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are not detectable.

Provided herein is a composition wherein the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine. Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is a composition wherein the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine. One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 1% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.5% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.4% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.3% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.25% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.20% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.15% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.10% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.08% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.05% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 1% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.5% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.4% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.3% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.25% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.20% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.15% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.10% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.08% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.05% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-

(5-fluoro-2-methylpyrimidin-4-yl)-6,6-dimethyl-1,4,5,6-tetrahydropyrrolo[3,4-c]pyrazol-3-amine is not detectable.

Provided herein is a composition wherein the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of impurities. In some embodiments, the composition is free of structurally related impurities. Provided herein is a composition wherein crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of impurities. In some embodiments, the composition is essentially free of structurally related impurities.

Provided herein is a composition wherein the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of impurities. In some embodiments, the composition is substantially free of structurally related impurities. One embodiment provides a composition wherein the amount of impurities is less than 1% (w/w). One embodiment provides a composition wherein the amount of impurities is less than 0.5% (w/w). One embodiment provides a composition wherein the amount of impurities is less than 0.4% (w/w). One embodiment provides a composition wherein the amount of impurities is less than 0.3% (w/w). One embodiment provides a composition wherein the amount of impurities is less than 0.25% (w/w). One embodiment provides a composition wherein the amount of impurities is less than 0.20% (w/w). One embodiment provides a composition wherein the amount of impurities is less than 0.15% (w/w). One embodiment provides a composition wherein the amount of impurities is less than 0.10% (w/w). One embodiment provides a composition wherein the amount of impurities is less than 0.08% (w/w). One embodiment provides a composition wherein the amount of impurities is less than 0.05% (w/w). One embodiment provides a composition wherein the amount of impurities is not more than 1% (w/w). One embodiment provides a composition wherein the amount of impurities is not more than 0.5% (w/w). One embodiment provides a composition wherein the amount of impurities is not more than 0.4% (w/w). One embodiment provides a composition wherein the amount of impurities is not more than 0.3% (w/w). One embodiment provides a composition wherein the amount of impurities is not more than 0.25% (w/w). One embodiment provides a composition wherein the amount of impurities is not more than 0.20% (w/w). One embodiment provides a composition wherein the amount of impurities is not more than 0.15% (w/w). One embodiment provides a composition wherein the amount of impurities is not more than 0.10% (w/w). One embodiment provides a composition wherein the amount of impurities is not more than 0.08% (w/w). One embodiment provides a composition wherein the amount of impurities is not more than 0.05% (w/w). One embodiment provides a composition wherein the amount of impurities is not detectable.

Provided herein is a composition wherein the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of solvent. One embodiment provides a composition wherein the amount of solvent is less than 20% (w/w). One embodiment provides a composition wherein the amount of solvent is less than 15% (w/w). One embodiment provides a composition wherein the amount of solvent is less than 10% (w/w). One embodiment provides a composition wherein the amount of solvent is less than 5% (w/w). One embodiment provides a composition wherein the amount of solvent is not more than 20% (w/w). One embodiment provides a composition wherein the amount of solvent is not more than 15% (w/w). One embodiment provides a composition wherein the amount of solvent is not more than 10% (w/w). One embodiment provides a composition wherein the amount of solvent is not more than 5% (w/w). One embodiment provides a composition wherein the amount of solvent is less than 2.0 equivalents. One embodiment provides a composition wherein the amount of solvent is less than 1.5 equivalents. One embodiment provides a composition wherein the amount of solvent is less than 1.0 equivalent. One embodiment provides a composition wherein the amount of solvent is not more than 2.0 equivalents. One embodiment provides a composition wherein the amount of solvent is not more than 1.5 equivalents. One embodiment provides a composition wherein the amount of solvent is not more than 1.0 equivalent.

Provided herein is a composition wherein the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of water. One embodiment provides a composition wherein the amount of water is less than 20% (w/w). One embodiment provides a composition wherein the amount of water is less than 15% (w/w). One embodiment provides a composition wherein the amount of water is less than 10% (w/w). One embodiment provides a composition wherein the amount of water is less than 7.5% (w/w). One embodiment provides a composition wherein the amount of water is less than 7.0% (w/w). One embodiment provides a composition wherein the amount of water is less than 6.5% (w/w). One embodiment provides a composition wherein the amount of water is less than 6.0% (w/w). One embodiment provides a composition wherein the amount of water is less than 5.5% (w/w). One embodiment provides a composition wherein the amount of water is less than 5.0% (w/w). One embodiment provides a composition wherein the amount of water is not more than 20% (w/w). One embodiment provides a composition wherein the amount of water is not more than 15% (w/w). One embodiment provides a composition wherein the amount of water is not more than 10% (w/w). One embodiment provides a composition wherein the amount of water is not more than 7.5% (w/w). One embodiment provides a composition wherein the amount of water is not more than 7.0% (w/w). One embodiment provides a composition wherein the amount of water is not more than 6.5% (w/w). One embodiment provides a composition wherein the amount of water is not more than 6.0% (w/w). One embodiment provides a composition wherein the amount of water is not more than 5.5% (w/w). One embodiment provides a composition wherein the amount of water is not more than 5.0% (w/w). One embodiment provides a composition wherein the amount of water is less than 2.0 equivalents. One embodiment provides a composition wherein the amount of water is less than 1.5 equivalents. One embodiment provides a composition wherein the amount of water is less than 1.0 equivalent. One embodiment provides a composition wherein the amount of water is not more than 2.0 equivalents. One embodiment provides a composition wherein the amount of water is not more than 1.5 equivalents. One embodiment provides a composition wherein the amount of water is not more than 1.0 equivalents.

Crystalline 2-Propanol Solvate Form A

Provided herein is a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of bis(34(5-fluoro-2-methylpyrimidin-4-yl)amino)-6,6-dimethyl-4,6-dihydropyrrolo[3,4-c]pyrazol-5(1H)-yl)methanone.

Provided herein is a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of bis(3-((5-fluoro-2-methylpyrimidin-4-yl)amino)-6,6-dimethyl-4,6-dihydropyrrolo[3,4-c]pyrazol-5(1H)-yl)methanone.

Provided herein is a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of bis(3-((5-fluoro-2-methylpyrimidin-4-yl)amino)-6,6-dimethyl-4,6-dihydropyrrolo[3,4-c]pyrazol-5(1H)-yl)methanone. One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 1% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.5% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.4% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.3% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.25% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.20% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.15% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.10% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.08% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is less than 0.05% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 1% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.5% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.4% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.3% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.25% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.20% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.15% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.10% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.08% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not more than 0.05% (w/w). One embodiment provides a composition wherein the bis(3-((5-fluoro-2-methylpyrimidin-4-yl)amino)-6,6-dimethyl-4,6-dihydropyrrolo[3,4-c]pyrazol-5(1H)-yl)methanone is not detectable.

Provided herein is a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate. Provided herein is a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate.

Provided herein is a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)

piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate. One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 1% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.5% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.4% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.3% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.25% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.20% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.15% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.10% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.08% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each less than 0.05% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 1% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.5% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.4% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.3% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6, 6-dimethyl-5,6-dihydropyrrolo[3,4-c]pyrazole-1(4H)-carboxylate are each not more than 0.25% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.20% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.15% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.10% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.08% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are each not more than 0.05% (w/w). One embodiment provides a composition wherein the ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate are not detectable.

Provided herein is a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine. Provided herein is a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Provided herein is a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine. One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 1% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.5% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.4% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.3% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.25% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.20% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.15% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.10% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.08% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is less than 0.05% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 1% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.5% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.4% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.3% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.25% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.20% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.15% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.10% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.08% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not more than 0.05% (w/w). One embodiment provides a composition wherein the amount of other solid forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is not detectable.

Provided herein is a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of impurities. In some embodiments, the composition is free of structurally related impurities. Provided herein is a composition wherein crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of impurities. In some embodiments, the composition is essentially free of structurally related impurities.

Provided herein is a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of impurities. In some embodiments, the composition is substantially free of structurally related impurities. One embodiment provides a composition wherein the amount of impurities is less than 1% (w/w). One embodiment provides a composition wherein the amount of impurities is less than 0.5% (w/w). One embodiment provides a composition wherein the amount of impurities is less than 0.4% (w/w). One embodiment provides a composition wherein the amount of impurities is less than 0.3% (w/w). One embodiment provides a composition wherein the amount of impurities is less than 0.25% (w/w). One embodiment provides a composition wherein the amount of impurities is less than 0.20% (w/w). One embodiment provides a composition wherein the amount of impurities is less than 0.15% (w/w). One embodiment provides a composition wherein the amount of impurities is less than 0.10% (w/w). One embodiment provides a composition wherein the amount of impurities is less than 0.08% (w/w). One embodiment provides a composition wherein the amount of impurities is less than 0.05% (w/w). One embodiment provides a composition wherein the amount of impurities is not more than 1% (w/w). One embodiment provides a composition wherein the amount of impurities is not more than 0.5% (w/w). One embodiment provides a composition wherein the amount of impurities is not more than 0.4% (w/w). One embodiment provides a composition wherein the amount of impurities is not more than 0.3% (w/w). One embodiment provides a composition wherein the amount of impurities is not more than 0.25% (w/w). One embodiment provides a composition wherein the amount of impurities is not more than 0.20% (w/w). One embodiment provides a composition wherein the amount of impurities is not more than 0.15% (w/w). One embodiment provides a composition wherein the amount of impurities is not more than 0.10% (w/w). One embodiment provides a composition wherein the amount of impurities is not more than 0.08% (w/w). One embodiment provides a composition wherein the amount of impurities is not more than 0.05% (w/w). One embodiment provides a composition wherein the amount of impurities is not detectable.

Provided herein is a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of solvent. One embodiment provides a composition wherein the amount of solvent is less than 20% (w/w). One embodiment provides a composition wherein the amount of solvent is less than 15% (w/w). One embodiment provides a composition wherein the amount of solvent is less than 10% (w/w). One embodiment provides a composition wherein the amount of solvent is less than 5% (w/w). One embodiment provides a composition wherein the amount of solvent is not more than 20% (w/w). One embodiment provides a composition wherein the amount of solvent is not more than 15% (w/w). One embodiment provides a composition wherein the amount of solvent is not more than 10%

(w/w). One embodiment provides a composition wherein the amount of solvent is not more than 5% (w/w). One embodiment provides a composition wherein the amount of solvent is less than 2.0 equivalents. One embodiment provides a composition wherein the amount of solvent is less than 1.5 equivalents. One embodiment provides a composition wherein the amount of solvent is less than 1.0 equivalent. One embodiment provides a composition wherein the amount of solvent is not more than 2.0 equivalents. One embodiment provides a composition wherein the amount of solvent is not more than 1.5 equivalents. One embodiment provides a composition wherein the amount of solvent is not more than 1.0 equivalent.

Provided herein is a composition wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of 2-propanol. One embodiment provides a composition wherein the amount of 2-propanol is less than 20% (w/w). One embodiment provides a composition wherein the amount of 2-propanol is less than 15% (w/w). One embodiment provides a composition wherein the amount of 2-propanol is less than 10% (w/w). One embodiment provides a composition wherein the amount of 2-propanol is less than 5% (w/w). One embodiment provides a composition wherein the amount of 2-propanol is not more than 20% (w/w). One embodiment provides a composition wherein the amount of 2-propanol is not more than 15% (w/w). One embodiment provides a composition wherein the amount of 2-propanol is not more than 10% (w/w). One embodiment provides a composition wherein the amount of 2-propanol is not more than 5% (w/w). One embodiment provides a composition wherein the amount of 2-propanol is less than 2.0 equivalents. One embodiment provides a composition wherein the amount of 2-propanol is less than 1.5 equivalents. One embodiment provides a composition wherein the amount of 2-propanol is less than 1.0 equivalent. One embodiment provides a composition wherein the amount of 2-propanol is not more than 2.0 equivalents. One embodiment provides a composition wherein the amount of 2-propanol is not more than 1.5 equivalents. One embodiment provides a composition wherein the amount of 2-propanol is not more than 1.0 equivalent.

Pharmaceutical Compositions

Provided herein is a pharmaceutical composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, and one or more pharmaceutically acceptable excipients or carriers. Also provided herein is a pharmaceutical composition comprising 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and one or more pharmaceutically acceptable excipients or carriers. In various embodiments, the pharmaceutical composition further comprises a pharmaceutically acceptable vehicle, carrier, diluent, or excipient, or a mixture thereof.

Provided herein is a pharmaceutical composition comprising an amorphous solid of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and one or more pharmaceutically acceptable excipients or carriers. Also provided herein is a pharmaceutical composition comprising an amorphous solid of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and one or more pharmaceutically acceptable excipients or carriers. In various embodiments, the pharmaceutical composition further comprises a pharmaceutically acceptable vehicle, carrier, diluent, or excipient, or a mixture thereof.

Provided herein is a pharmaceutical composition comprising the maleate salt of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and one or more pharmaceutically acceptable excipients or carriers. In various embodiments, the pharmaceutical composition comprises a pharmaceutically acceptable vehicle, carrier, diluent, or excipient, or a mixture thereof.

Provided herein is a pharmaceutical composition comprising the fumarate salt of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and one or more pharmaceutically acceptable excipients or carriers. In various embodiments, the pharmaceutical composition comprises a pharmaceutically acceptable vehicle, carrier, diluent, or excipient, or a mixture thereof.

Provided herein is a pharmaceutical composition comprising crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and one or more pharmaceutically acceptable excipients or carriers. Also provided herein is a pharmaceutical composition comprising crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and one or more pharmaceutically acceptable excipients or carriers. In various embodiments, the pharmaceutical composition comprises a pharmaceutically acceptable vehicle, carrier, diluent, or excipient, or a mixture thereof.

Provided herein is a pharmaceutical composition comprising crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and one or more pharmaceutically acceptable excipients or carriers. Also provided herein is a pharmaceutical composition comprising crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and one or more pharmaceutically acceptable excipients or carriers. In various embodiments, the pharmaceutical composition comprises a pharmaceutically acceptable vehicle, carrier, diluent, or excipient, or a mixture thereof.

Provided herein is a pharmaceutical composition comprising crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and one or more pharmaceutically acceptable excipients or carriers. Also provided herein is a pharmaceutical composition comprising crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and one or more pharmaceutically acceptable excipients or carriers. In various embodiments, the pharmaceutical composition comprises a pharmaceutically acceptable vehicle, carrier, diluent, or excipient, or a mixture thereof.

Provided herein is a pharmaceutical composition comprising crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and one or more pharmaceutically acceptable excipients or carriers. Also provided herein is a pharmaceutical composition comprising crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and one or more pharmaceutically acceptable excipients or carriers. In various embodiments, the pharmaceutical composition comprises a pharmaceutically acceptable vehicle, carrier, diluent, or excipient, or a mixture thereof.

Provided herein is a pharmaceutical composition comprising crystalline solid Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and one or more pharmaceutically acceptable excipients or carriers. Also provided herein is a pharmaceutical composition comprising crystalline solid Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and one or more pharmaceutically acceptable excipients or carriers. In various embodiments, the pharmaceutical composition comprises a pharmaceutically acceptable vehicle, carrier, diluent, or excipient, or a mixture thereof.

Provided herein is a pharmaceutical composition comprising crystalline solid Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and one or more pharmaceutically acceptable excipients or carriers. Also provided herein is a pharmaceutical composition comprising crystalline solid Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and one or more pharmaceutically acceptable excipients or carriers. In various embodiments, the pharmaceutical composition comprises a pharmaceutically acceptable vehicle, carrier, diluent, or excipient, or a mixture thereof.

Provided herein is a pharmaceutical composition comprising crystalline solid Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and one or more pharmaceutically acceptable excipients or carriers. Also provided herein is a pharmaceutical composition comprising crystalline solid Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and one or more pharmaceutically acceptable excipients or carriers. In various embodiments, the pharmaceutical composition comprises a pharmaceutically acceptable vehicle, carrier, diluent, or excipient, or a mixture thereof.

One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of impurities. In some embodiments, the composition is free of structurally related impurities. One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of impurities. In some embodiments, the composition is essentially free of structurally related impurities. One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of impurities. In some embodiments, the composition is substantially free of structurally related impurities.

One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of bis(3-((5-fluoro-2-methylpyrimidin-4-yl)amino)-6,6-dimethyl-4,6-dihydropyrrolo[3,4-c]pyrazol-5(1H)-yl)methanone. One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of bis(3-((5-fluoro-2-methylpyrimidin-4-yl)amino)-6,6-dimethyl-4,6-dihydropyrrolo[3,4-c]pyrazol-5(1H)-yl)methanone. One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of bis(3-((5-fluoro-2-methylpyrimidin-4-yl)amino)-6,6-dimethyl-4,6-dihydropyrrolo[3,4-c]pyrazol-5(1H)-yl)methanone.

One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate. One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is essentially free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4- c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate. One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine is substantially free of ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate, and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate.

One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine contains less than 20% of solvent (w/w). One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine contains less than 15% of solvent (w/w). One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine contains less than 10% of solvent (w/w). One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine contains less than 5% of solvent (w/w).

One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine contains less than 20% of water (w/w). One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine contains less than 15% of water (w/w). One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine contains less than 10% of water (w/w). One embodiment provides a pharmaceutical composition, wherein the 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine contains less than 5% of water (w/w).

Provided herein is a pharmaceutical compositions comprising any pharmaceutically acceptable salt of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and one or more pharmaceutically acceptable excipients or carriers. In various embodiments, the pharmaceutical composition comprises a pharmaceutically acceptable vehicle, carrier, diluent, or excipient, or a mixture thereof.

Provided herein are pharmaceutical compositions in film-coated dosage forms, which comprise a combination of an active ingredient, and one or more tableting excipients to form a tablet core using conventional tableting processes and subsequently coating the core. The tablet cores can be produced using conventional granulation methods, for example wet or dry granulation, with optional comminution of the granules and with subsequent compression and coating.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In the case wherein the patient's condition does not improve, upon the doctor's discretion the administration of the combinations may be administered chronically, that is, for an extended period of time, including throughout the duration of the patient's life in order to ameliorate or otherwise control or limit the symptoms of the patient's disease or condition. In the case wherein the patient's status does improve, upon the doctor's discretion the administration of the combinations may be given continuously or temporarily suspended for a certain length of time (i.e., a "drug holiday"). In some embodiments, once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

Treatment dosages generally may be titrated to optimize safety and efficacy. Typically, dosage-effect relationships from in vitro studies initially can provide useful guidance on the proper doses for patient administration. Studies in animal models also generally may be used for guidance regarding effective dosages for treatment in accordance with the present disclosure. In terms of treatment protocols, it should be appreciated that the dosage to be administered will depend on several factors, including the particular agent that is administered, the route administered, the condition of the particular patient, etc. Determination of these parameters is well within the skill of the art. These considerations, as well as effective formulations and administration procedures are well known in the art and are described in standard textbooks.

The pharmaceutical compositions provided herein are formulated in various dosage forms for oral administration. These dosage forms can be prepared according to conventional methods and techniques known to those skilled in the art (see, *Remington: The Science and Practice of Pharmacy*, Loyd V., Jr, Allen, Ed., Pharmaceutical Press: New York, N.Y., 2002; Vol. 22).

As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, and effervescent or non-effervescent powders or granules. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents. In some embodiments, the oral dosage form is a tablet, capsule, or pill.

In further embodiments, the pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule, consists of two sections, one slipping over the other, thus completely enclosing the active ingredient. The soft elastic capsule is a soft, globular shell, such as a gelatin shell, which is plasticized by the addition of glycerin, sorbitol, or a similar polyol. The liquid, semisolid, and solid dosage forms provided herein may be encapsulated in a capsule. Suitable liquid and semisolid dosage forms include solutions and suspensions in propylene carbonate, vegetable oils, or triglycerides.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The examples and preparations provided below further illustrate and exemplify the polymorphs of the present disclosure and methods of preparing such polymorphs. It is to be understood that the scope of the present disclosure is not limited in any way by the scope of the following examples and preparations.

The present disclosure relates to various solid state forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and methods of making the same. Such forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine are useful in the treatment of cancer, immune disorders and inflammation. In one embodiment the various solid state forms of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine disclosed herein are useful for the treatment of inflammatory disorders such as uveitis.

EXAMPLES

The present disclosure is further illustrated by the following examples, which should not be construed as limiting in any way. The experimental procedures to generate the data shown are discussed in more detail below. The disclosure has been described in an illustrative manner, and it is to be understood that the terminology used is intended to be in the nature of description rather than of limitation.

General Experimental Details—Instrument and Methodology Details

X-Ray Powder Diffraction (XRPD)

X-Ray Powder Diffraction patterns were collected on a PANalytical diffractometer using Cu Kα radiation (45 kV, 40 mA), θ-θ goniometer, focusing mirror, divergence slit (½"), soller slits at both incident and divergent beam (4 mm) and a PIXcel detector. The software used for data collection was X'Pert Data Collector, version 2.2f and the data was presented using X'Pert Data Viewer, version 1.2d.

XRPD patterns were acquired under ambient conditions via a transmission foil sample stage (polyimide—Kapton, 12.7 μm thickness film) under ambient conditions using a PANalytical X'Pert PRO. The data collection range was 2.994-35°2θ with a continuous scan speed of $0.202004°s^{-1}$.

Nuclear Magnetic Resonance (NMR)

$^1$H-NMR spectra were collected using a JEOL EX 270 MHz spectrometer equipped with an auto-sampler. The samples were dissolved in a suitable deuterated solvent for analysis. The data was acquired using Delta NMR Processing and Control Software version 4.3.

Differential Scanning calorimetry (DSC)

DSC data was collected on a PerkinElmer Pyris 4000 DSC equipped with a 45 position sample holder. The instrument was verified for energy and temperature calibration using certified indium. A predefined amount of the sample, 0.5-3.0 mg, was placed in a pin holed aluminum pan and heated at 20° C.·min$^{-1}$ from 30 to 350° C., or varied as experimentation dictated. A purge of dry nitrogen at 60 mL·min$^{-1}$ was maintained over the sample. The instrument control, data acquisition and analysis was performed with Pyris Software v9.0.1.0203.

Thermo-Gravimetric Analysis (TGA)

TGA data were collected on a PerkinElmer Pyris 1 TGA equipped with a 20 position auto-sampler. The instrument was calibrated using a certified weight and certified Alumel and Perkalloy for temperature. A predefined amount of sample, 1-5 mg, was loaded onto a pre-tared aluminium crucible and was heated at 20° C.·min$^{-1}$ from ambient temperature to 400° C. A nitrogen purge at 20 mL·min$^{-1}$ was maintained over the sample. The instrument control, data acquisition and analysis was performed with Pyris Software v9.0.1.0203.

Infrared Spectroscopy

Data was collected on a Perkin Elmer Spectrum Two instrument with μATR Two accessory. The software used for data collection and presentation was Spectrum, version 10.03.08. A few grains <1 mg of sample was compressed under a diamond tip for data collection.

Raman Spectroscopy

Raman spectra were collected on a PerkinElmer Raman Station 400. The software used for data collection and presentation was Spectrum, version 10.03.06. Raman spectra were acquired under ambient conditions with the sample presented on a glass microscope slide with Raman autofocus. The laser power was optimized as governed by the nature of the sample. The data collection range was 3400 to 200 cm-1 with an exposure time of 5-10 seconds at a data interval of 1 cm-1 over 10-30 accumulations as required for each sample.

Optical Microscopy

Optical microscopy examination was undertaken using a Leica DME polarized light microscope and an Infinity 1 digital video camera for image capture. A small amount of each sample was placed onto a glass slide and dispersed as best as possible. The samples were viewed with appropriate magnification and various images recorded. The image scale bar was calibrated against an external graticule, 0.1 mm/0.002 mm DIV.

Gravimetric Vapor Sorption (GVS)

Sorption isotherms were obtained using a Hiden Isochema moisture sorption analyzer (model IGAsorp), controlled by IGAsorp Systems Software V6.50.48. The sample was maintained at a constant temperature (25° C.) by the instrument controls. The humidity was controlled by mixing streams of dry and wet nitrogen, with a total flow of 250 mL·min$^{-1}$. The instrument was verified for relative humidity content by measuring three calibrated Rotronic salt solutions (10-50-88%). The weight change of the sample was monitored as a function of humidity by a microbalance (accuracy +/−0.005 mg). A defined amount of sample was placed in a tared mesh stainless steel basket under ambient conditions. A full experimental cycle typically consisted of three scans (sorption, desorption and sorption) at a constant temperature (25° C.) and 10% RH intervals over a 0-90% range (60 minutes for each humidity level). This type of experiment should demonstrate the ability of samples studied to absorb moisture (or not) over a set of well-determined humidity ranges.

Chemical Purity Determination by HPLC

Purity analysis was performed on an Agilent 1100 series liquid chromatograph.

TABLE 2

HPLC Method Parameters for Chemical Purity Determinations

| Sample Preparation: | 0.5 mg · ml$^{-1}$ in Acetonitrile:Water (1:1) |
|---|---|
| Column: | Sunfire C18 4.6 × 250 mm; 5 μm |
| Column Temperature: | 40° C. |
| Injection: | 5 μl & Needle wash vial with diluent |
| Detection: | 254 nm |
| Wavelength, Bandwidth: | |
| Flow Rate: | 1.0 mL · min$^{-1}$ |
| Phase A: | 10 mM Ammonium acetate pH 4.0 (100) |
| Phase B: | Acetonitrile (100) |

| Timetable: | Time (min) | % Phase A | % Phase |
|---|---|---|---|
| | 0 | 95 | 5 |
| | 5 | 95 | 5 |
| | 20 | 65 | 35 |
| | 30 | 5 | 95 |
| | 32.1 | 95 | 5 |
| | 40 | 95 | 5 |

Example 1: Processes for the Synthesis of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-d]pyrazol-3-amine (Compound 1)

A synthesis of Compound 1 was previously reported in WO 2008/096260. Optimized synthetic routes to Compound 1 are presented below.

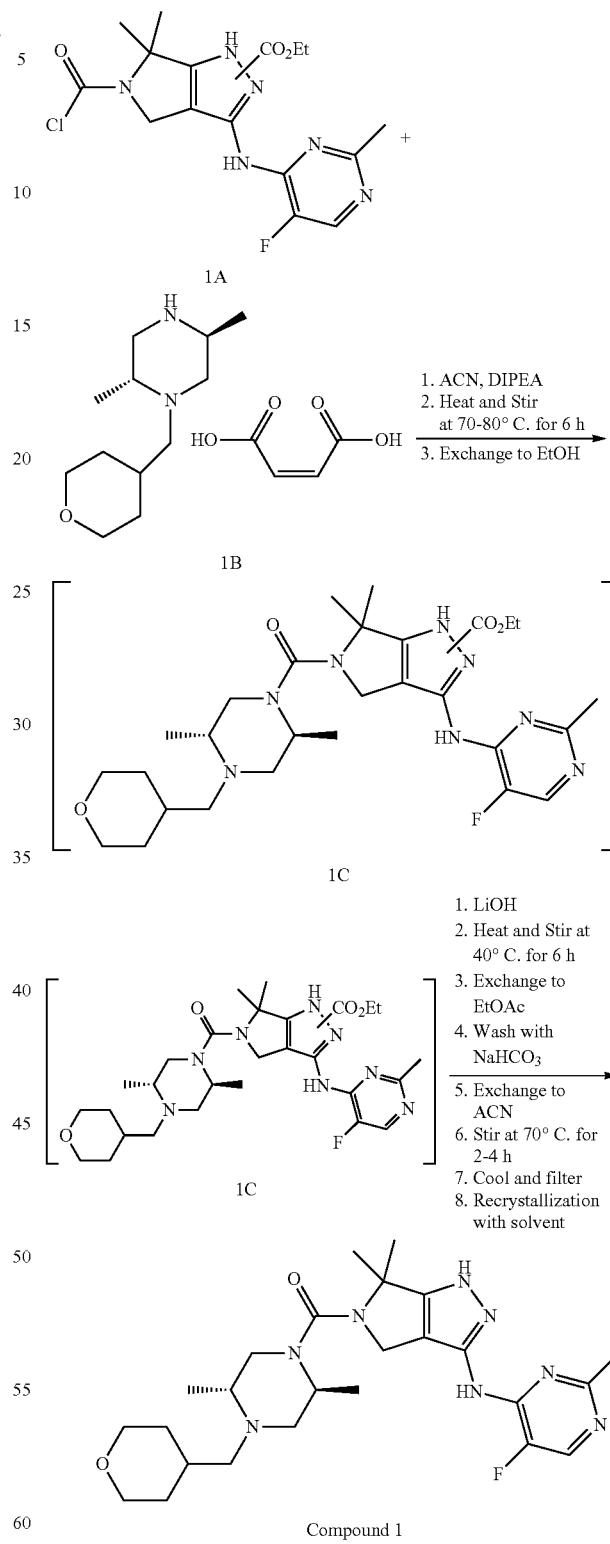

Scheme 1 - Synthesis of Compound 1

A reaction vessel was charged with compound 1A, compound 1B, N,N-diisopropylethylamine and acetonitrile. The reaction was heated to 70-80° C. for approximately 6 hours. Following the cooling of the reaction mixture to room temperature, the acetonitrile solvent was removed and replaced with ethanol to afford a solution of 1C. The solution of 1C was subsequently charged with lithium hydroxide and heated to 40° C. for approximately 6 hours. The reaction solvent was then exchanged for ethyl acetate and washed with a solution of sodium bicarbonate. Ethyl acetate was removed as the solvent, and exchanged for acetonitrile. The solution was subsequently stirred at 70° C. for 2-4 hours. The solution was then allowed to cool, and was filtered to afford solid Compound 1. Recrystallization of Compound 1 using acetonitrile or 2-propanol followed by water slurry and drying served to purify Compound 1 and eliminate the presence of impurity bis(3-((5-fluoro-2-methylpyrimidin-4-yl)amino)-6,6-dimethyl-4,6-dihydropyrrolo[3,4-c]pyrazol-5(1H)-yl)methanone (structure shown below), unreacted 1C (two carbamate isomers: ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-2(4H)-carboxylate and ethyl 5-((2S,5R)-2,5-dimethyl-4-((tetrahydro-2H-pyran-4-yl)methyl)piperazine-1-carbonyl)-3-((5-fluoro-2-methylpyrimidin-4-yl)amino)-6,6-dimethyl-5,6-dihydropyrrolo[3,4-c]pyrazole-1(4H)-carboxylate), and other unidentified impurities. Following this purification process, Compound 1 exhibited a purity of greater than 99.8% as determined by the analytical HPLC method described in Table 2.

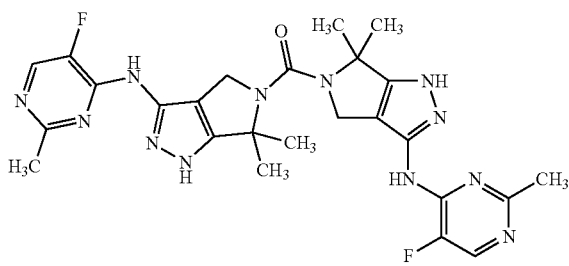

bis(3-((5-fluoro-2-methylpyrimidin-4-yl)amino)-
6,6-dimethyl-4,6-dihydropyrrolo[3,4-c]pyrazol-
5(1H)-yl)methanone Example 2: Process for the Synthesis of amorphous solid 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine The crystalline hydrate of Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine was dried in a vacuum oven at 50-70° C. for 6-12 hours. The resulting solid exhibited the powder X-ray diffraction pattern displayed in FIG. 1, and the DSC and TGA displayed in FIGS. 2a-2b.

Figure 4:
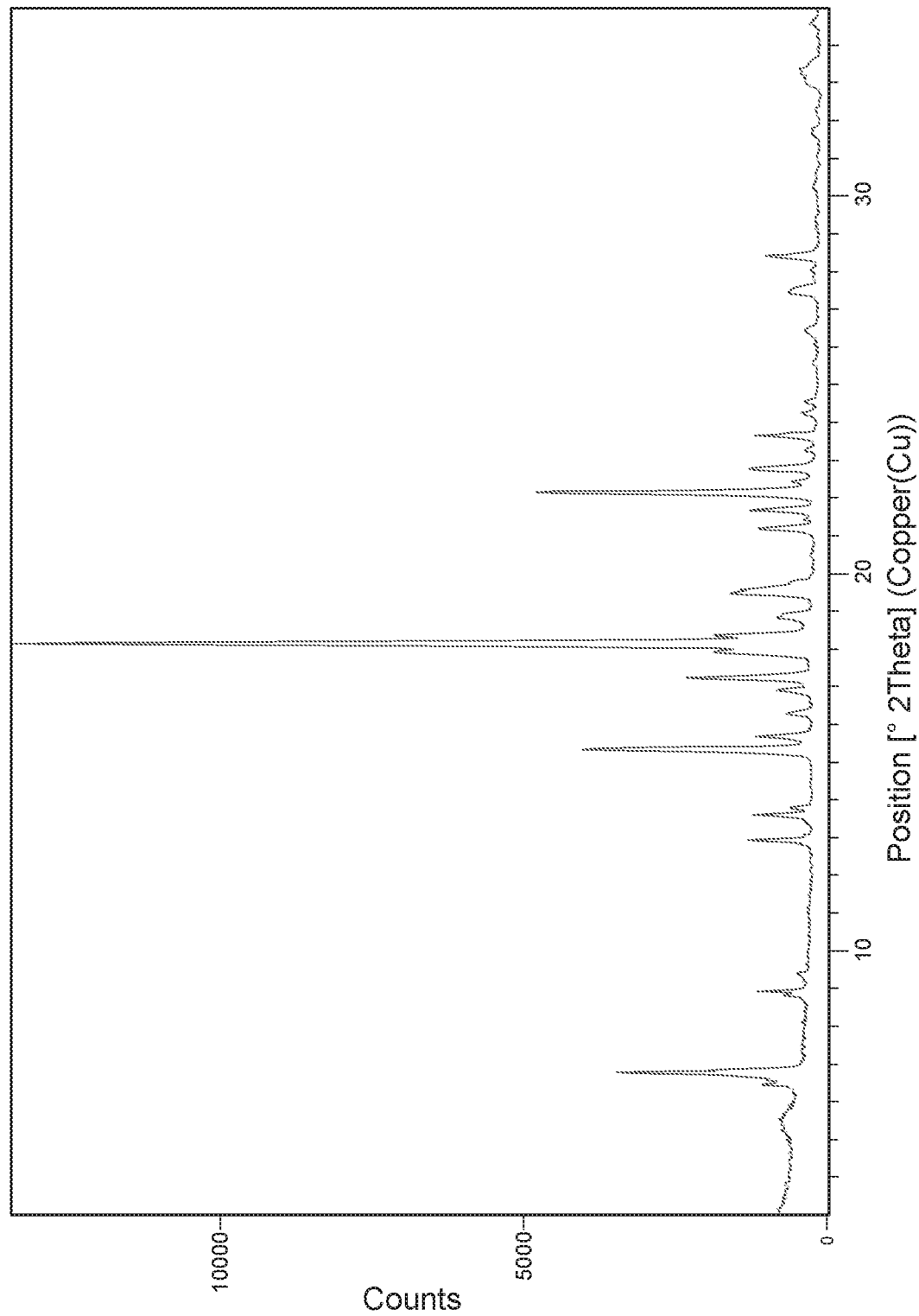
FIG. 4 shows the X-ray powder diffractogram of crystalline 2-propanol solvate Form A of 5-{[(2S,5R)-2,5-dimethyl-4-(tetrahydro-2H-pyran-4-ylmethyl)piperazin-1-yl] carbonyl}-N-(5-fluoro-2-methylpyrimidin-4-yl)-6,6-dimethyl-1,4,5,6-tetrahydropyrrolo[3,4-c]pyrazol-3-amine without annotation.

Example 3: Process for the Synthesis of a crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine Following the final step of the procedure outlined in Scheme 1, recrystallization of Compound 1 from 2-propanol provided crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine. Recrystallization was accomplished by dissolving 30 g of Compound 1 in 200 mL 2-propanol at 70-85° C. Cooling the solution to 0-10° C. afforded crystalline material collected via filtration. Drying at 45° C. temperature for 5-10 hours yielded crystalline Form A in 64% yield. The resulting solid exhibited the powder X-ray diffraction pattern displayed in FIGS. 3-4, and Table 3, the DSC and TGA displayed in FIGS. 5-6, and the infrared spectrum displayed in FIGS. 7-9.

TABLE 3

Peak listing for the X-ray powder diffractogram of crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine

| Pos. [°2Th.] | Height [cts] | FWHM [°2Th.] | d-spacing [Å] | Rel. Int. [%] |
|---|---|---|---|---|
| 5.4553 | 218.33 | 0.5117 | 16.20011 | 1.64 |
| 6.4698 | 570.19 | 0.0768 | 13.66181 | 4.27 |
| 6.7690 | 3089.14 | 0.1279 | 13.05877 | 23.14 |
| 8.9299 | 843.34 | 0.0512 | 9.90296 | 6.32 |
| 9.3883 | 158.50 | 0.0768 | 9.42042 | 1.19 |
| 12.9330 | 1058.45 | 0.0768 | 6.84533 | 7.93 |
| 13.6041 | 1007.70 | 0.0768 | 6.50910 | 7.55 |
| 15.3404 | 3812.12 | 0.1279 | 5.77607 | 28.55 |
| 15.6855 | 962.24 | 0.1023 | 5.64977 | 7.21 |
| 16.2965 | 433.60 | 0.1023 | 5.43930 | 3.25 |
| 16.9017 | 612.88 | 0.1023 | 5.24585 | 4.59 |
| 17.2342 | 2115.39 | 0.1279 | 5.14539 | 15.84 |
| 17.8950 | 1592.15 | 0.0768 | 4.95686 | 11.93 |
| 18.1461 | 13350.91 | 0.1023 | 4.88884 | 100.00 |
| 18.3845 | 1526.00 | 0.0768 | 4.82596 | 11.43 |
| 18.8431 | 637.53 | 0.0936 | 4.70563 | 4.78 |
| 18.9361 | 523.54 | 0.0768 | 4.68662 | 3.92 |
| 19.4872 | 1355.32 | 0.1279 | 4.55531 | 10.15 |
| 19.6110 | 1030.01 | 0.0768 | 4.52683 | 7.71 |
| 21.1904 | 915.90 | 0.1279 | 4.19286 | 6.86 |
| 21.6838 | 1108.16 | 0.1279 | 4.09856 | 8.30 |
| 22.1456 | 4612.68 | 0.1279 | 4.01412 | 34.55 |
| 22.4303 | 387.74 | 0.0768 | 3.96381 | 2.90 |
| 22.7827 | 1112.80 | 0.1279 | 3.90329 | 8.33 |
| 23.2781 | 167.09 | 0.1023 | 3.82133 | 1.25 |
| 23.6557 | 995.86 | 0.1023 | 3.76118 | 7.46 |
| 24.2423 | 260.14 | 0.1023 | 3.67148 | 1.95 |
| 24.5501 | 212.39 | 0.1023 | 3.62615 | 1.59 |
| 25.5948 | 77.56 | 0.1535 | 3.48046 | 0.58 |
| 26.4362 | 213.47 | 0.1535 | 3.37156 | 1.60 |
| 27.4602 | 472.93 | 0.1279 | 3.24812 | 3.54 |
| 28.4022 | 852.95 | 0.1535 | 3.14250 | 6.39 |
| 29.3038 | 35.14 | 0.3070 | 3.04784 | 0.26 |
| 30.2677 | 88.49 | 0.2047 | 2.95293 | 0.66 |
| 31.6879 | 110.80 | 0.2047 | 2.82375 | 0.83 |
| 32.2548 | 43.58 | 0.2558 | 2.77541 | 0.33 |
| 32.9883 | 208.05 | 0.1535 | 2.71535 | 1.56 |
| 33.3155 | 313.83 | 0.2047 | 2.68943 | 2.35 |
| 34.5977 | 122.72 | 0.1535 | 2.59264 | 0.92 |

Figure 11:
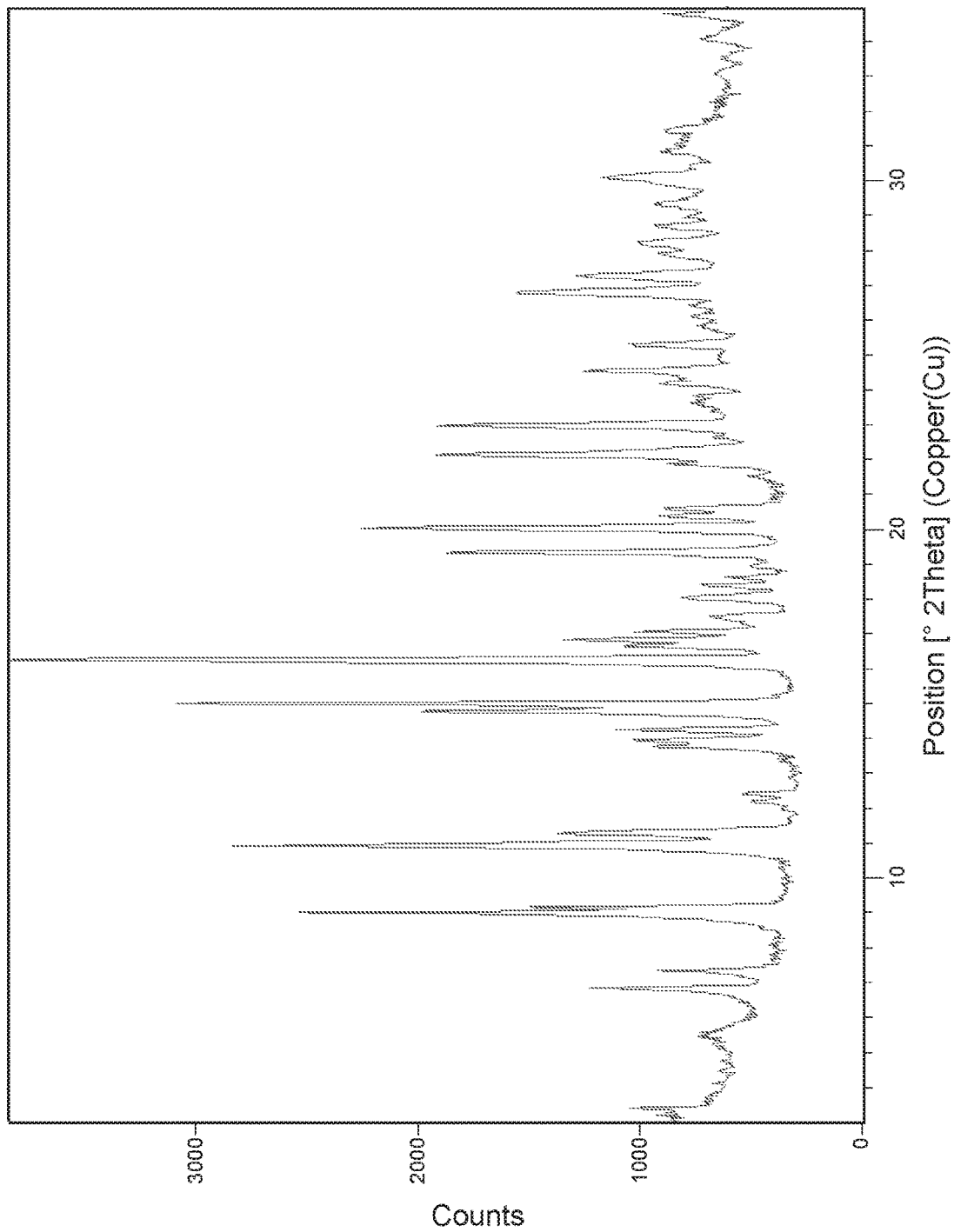
FIG. 11 shows the X-ray powder diffractogram of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine without annotation.
Figure 15:
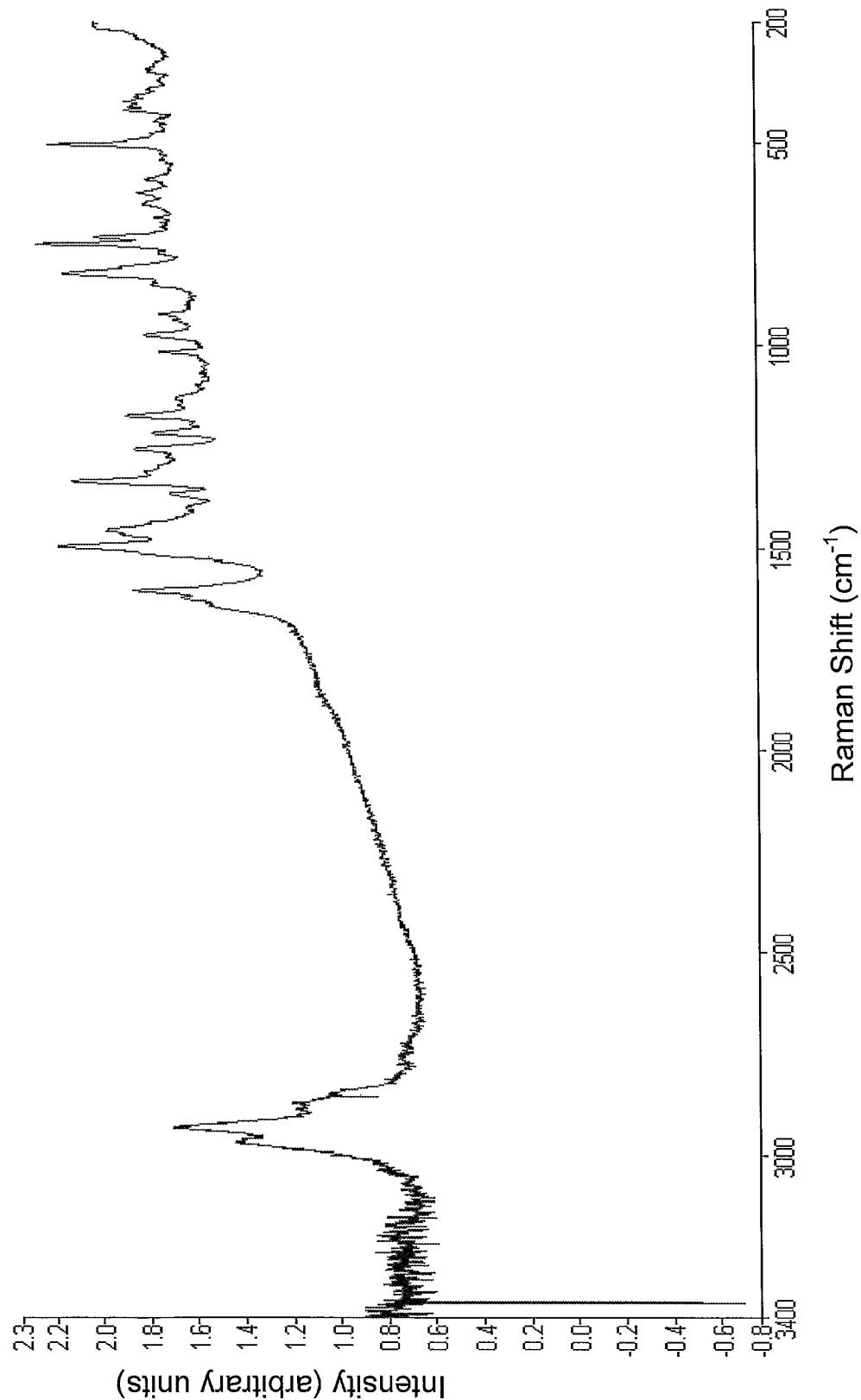
FIG. 15 shows the Raman spectrum of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine without annotation.
Figure 16:
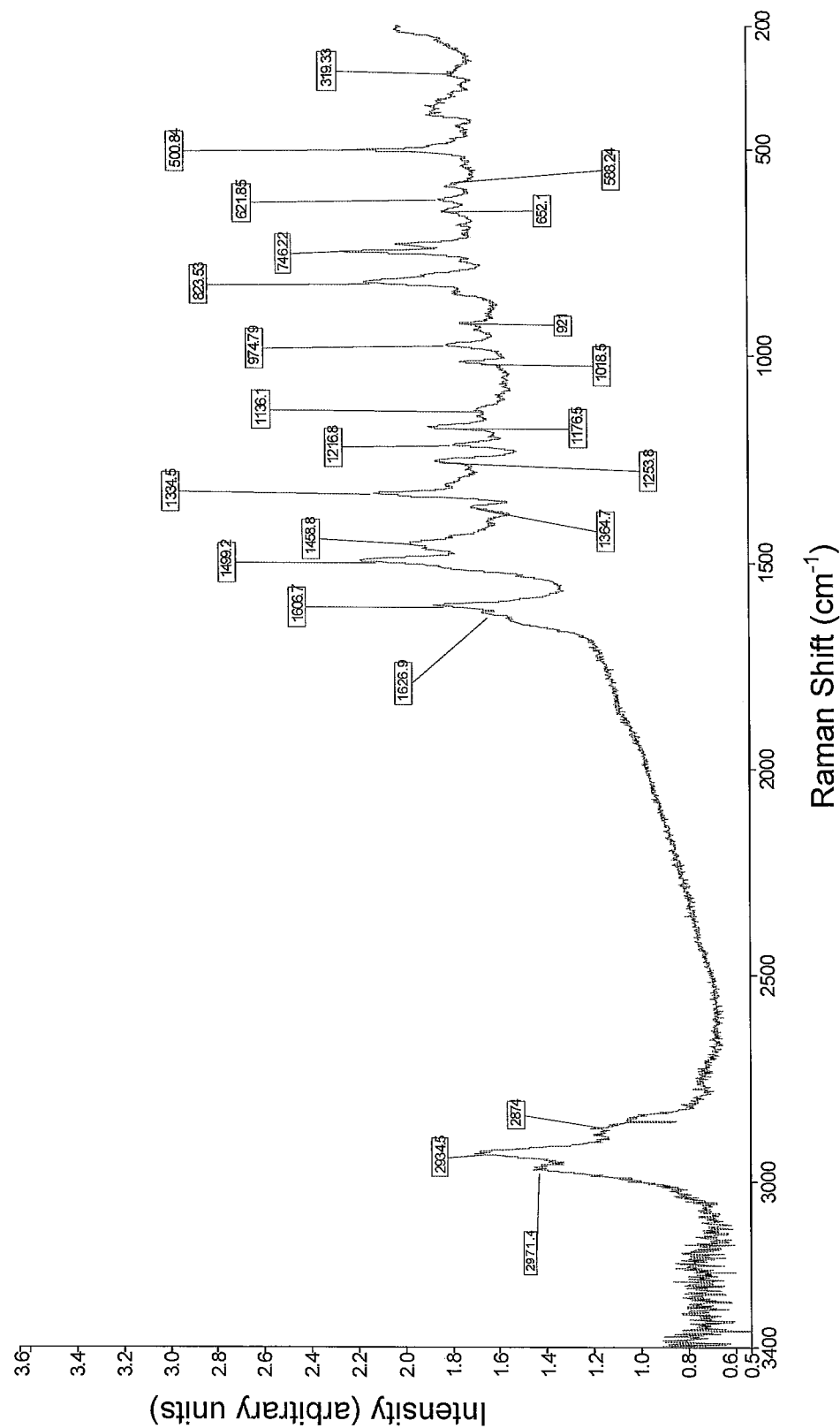
FIG. 16 shows the Raman spectrum of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine with peaks numerically identified.

Example 4: Process for the Synthesis of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine Crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine (10 g) was suspended in 120 mL of water and stirred for 24 hours. The solid was isolated via filtration and dried under ambient conditions on the filter for 2 hours to afford the crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine which exhibited the powder X-ray diffraction pattern displayed in FIGS. 10-11, and Table 4, the DSC and TGA displayed in FIGS. 12-13, the infrared spectrum displayed in FIG. 14 and the Raman spectra displayed in FIGS. 15-16.

TABLE 4

Peak listing for the X-ray powder diffractogram of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine

| Pos. [°2Th.] | Height [cts] | FWHM [°2Th.] | d-spacing [Å] | Rel. Int. [%] |
|---|---|---|---|---|
| 3.3999 | 421.69 | 0.0768 | 25.98791 | 11.93 |
| 5.5146 | 174.51 | 0.1535 | 16.02591 | 4.94 |
| 6.8414 | 784.32 | 0.0768 | 12.92058 | 22.19 |
| 7.3467 | 514.29 | 0.0768 | 12.03315 | 14.55 |
| 8.9999 | 2193.96 | 0.0768 | 9.82611 | 62.06 |
| 9.1700 | 1135.28 | 0.0512 | 9.64424 | 32.12 |
| 10.9295 | 2491.74 | 0.1279 | 8.09524 | 70.49 |
| 11.3063 | 994.88 | 0.1535 | 7.82631 | 28.14 |
| 12.1911 | 189.73 | 0.1023 | 7.26021 | 5.37 |
| 12.4074 | 234.16 | 0.1023 | 7.13411 | 6.62 |
| 13.7582 | 623.68 | 0.0768 | 6.43655 | 17.64 |
| 13.9555 | 723.13 | 0.1023 | 6.34602 | 20.46 |
| 14.2607 | 791.06 | 0.1023 | 6.21088 | 22.38 |
| 14.7640 | 1684.45 | 0.1023 | 6.00024 | 47.65 |
| 15.0050 | 2755.94 | 0.1023 | 5.90442 | 77.96 |
| 16.2619 | 3534.98 | 0.1279 | 5.45080 | 100.00 |
| 16.6330 | 730.39 | 0.0768 | 5.32999 | 20.66 |
| 16.8369 | 1014.46 | 0.1023 | 5.26590 | 28.70 |
| 17.0783 | 683.10 | 0.0768 | 5.19202 | 19.32 |
| 17.5325 | 316.45 | 0.1279 | 5.05853 | 8.95 |
| 18.0365 | 435.62 | 0.1791 | 4.91830 | 12.32 |
| 18.4002 | 348.00 | 0.1279 | 4.82189 | 9.84 |
| 18.6360 | 253.81 | 0.1023 | 4.76139 | 7.18 |
| 18.9462 | 130.97 | 0.1023 | 4.68414 | 3.71 |
| 19.3520 | 1499.85 | 0.1279 | 4.58683 | 42.43 |
| 20.0424 | 1882.77 | 0.1535 | 4.43036 | 53.26 |
| 20.3853 | 545.35 | 0.1023 | 4.35660 | 15.43 |
| 20.6123 | 513.60 | 0.1023 | 4.30913 | 14.53 |
| 21.5128 | 129.59 | 0.0768 | 4.13074 | 3.67 |
| 21.8602 | 417.75 | 0.1023 | 4.06588 | 11.82 |
| 22.1424 | 1512.60 | 0.1279 | 4.01469 | 42.79 |
| 22.6232 | 243.57 | 0.0768 | 3.93044 | 6.89 |
| 22.9842 | 1482.27 | 0.1279 | 3.86952 | 41.93 |
| 23.8435 | 306.35 | 0.0768 | 3.73198 | 8.67 |
| 24.1876 | 434.97 | 0.1023 | 3.67967 | 12.30 |
| 24.5795 | 759.68 | 0.1279 | 3.62188 | 21.49 |
| 25.2870 | 543.04 | 0.1535 | 3.52213 | 15.36 |
| 25.7950 | 230.10 | 0.1535 | 3.45390 | 6.51 |
| 26.1041 | 272.44 | 0.0768 | 3.41371 | 7.71 |
| 26.7841 | 1050.92 | 0.1791 | 3.32856 | 29.73 |
| 27.3055 | 733.34 | 0.2047 | 3.26618 | 20.75 |
| 27.9204 | 368.68 | 0.2047 | 3.19563 | 10.43 |
| 28.2701 | 424.91 | 0.2047 | 3.15689 | 12.02 |
| 28.6771 | 355.41 | 0.1791 | 3.11300 | 10.05 |
| 29.3211 | 337.18 | 0.1535 | 3.04607 | 9.54 |
| 30.0823 | 590.94 | 0.1023 | 2.97071 | 16.72 |
| 30.8254 | 302.08 | 0.1279 | 2.90077 | 8.55 |
| 31.4243 | 255.93 | 0.1023 | 2.84684 | 7.24 |
| 33.1065 | 64.16 | 0.2047 | 2.70593 | 1.81 |
| 33.5449 | 42.56 | 0.1535 | 2.67156 | 1.20 |
| 34.0559 | 152.09 | 0.1279 | 2.63264 | 4.30 |
| 34.7678 | 307.22 | 0.1023 | 2.58035 | 8.69 |

Figure 18:
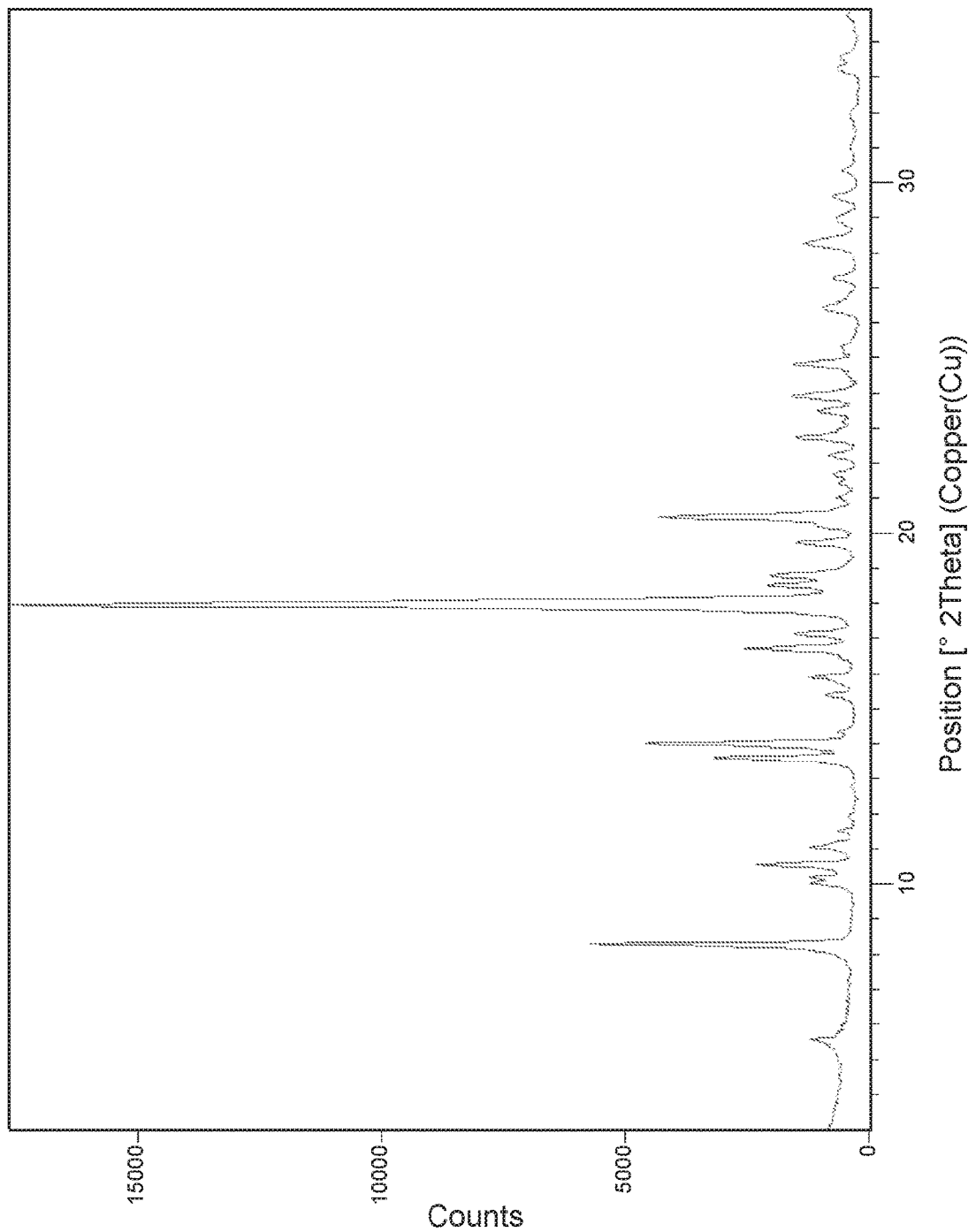
FIG. 18 shows the X-ray powder diffractogram of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine without annotation.
Figure 22:
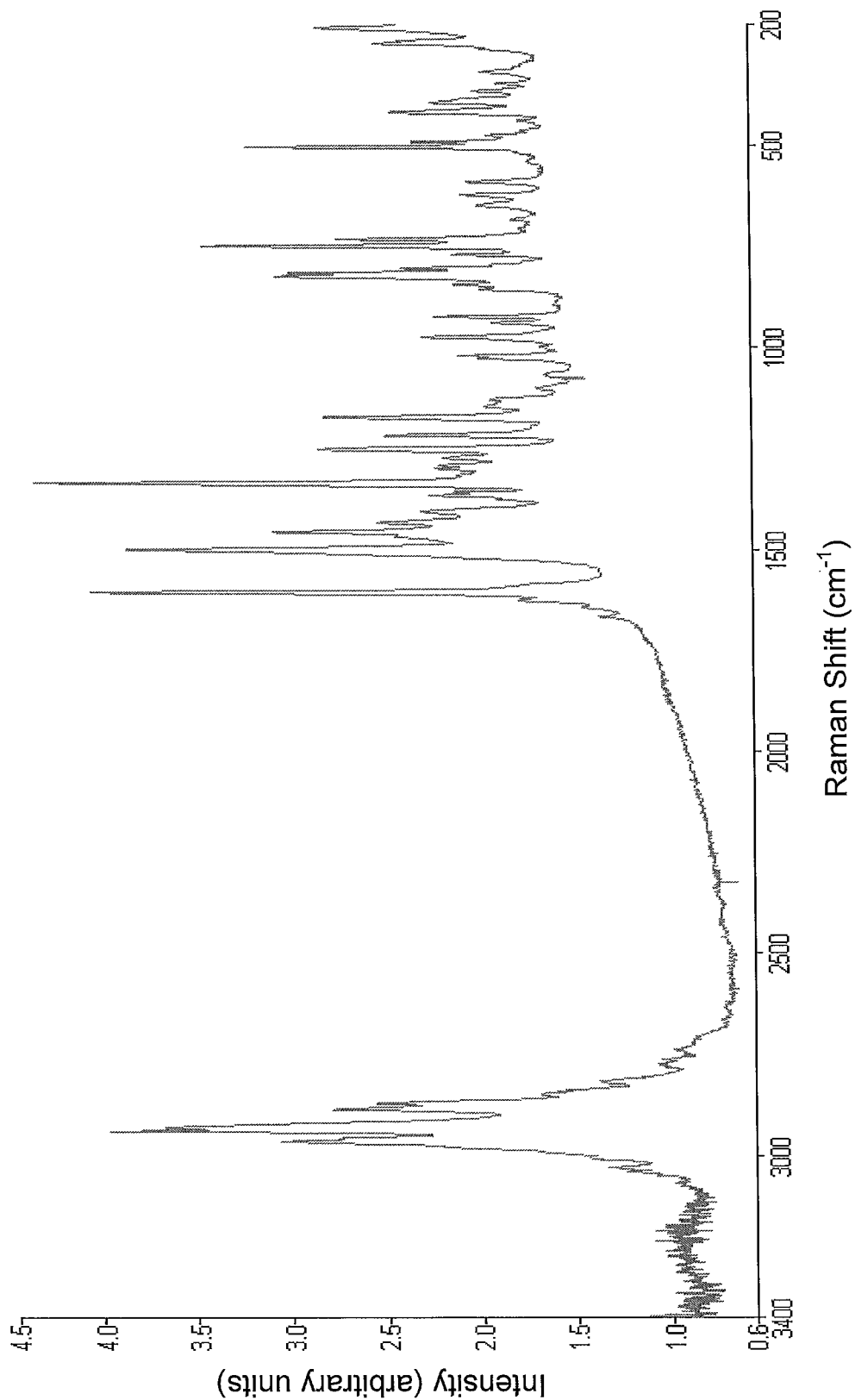
FIG. 22 shows the Raman spectrum of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine without annotation.
Figure 23:
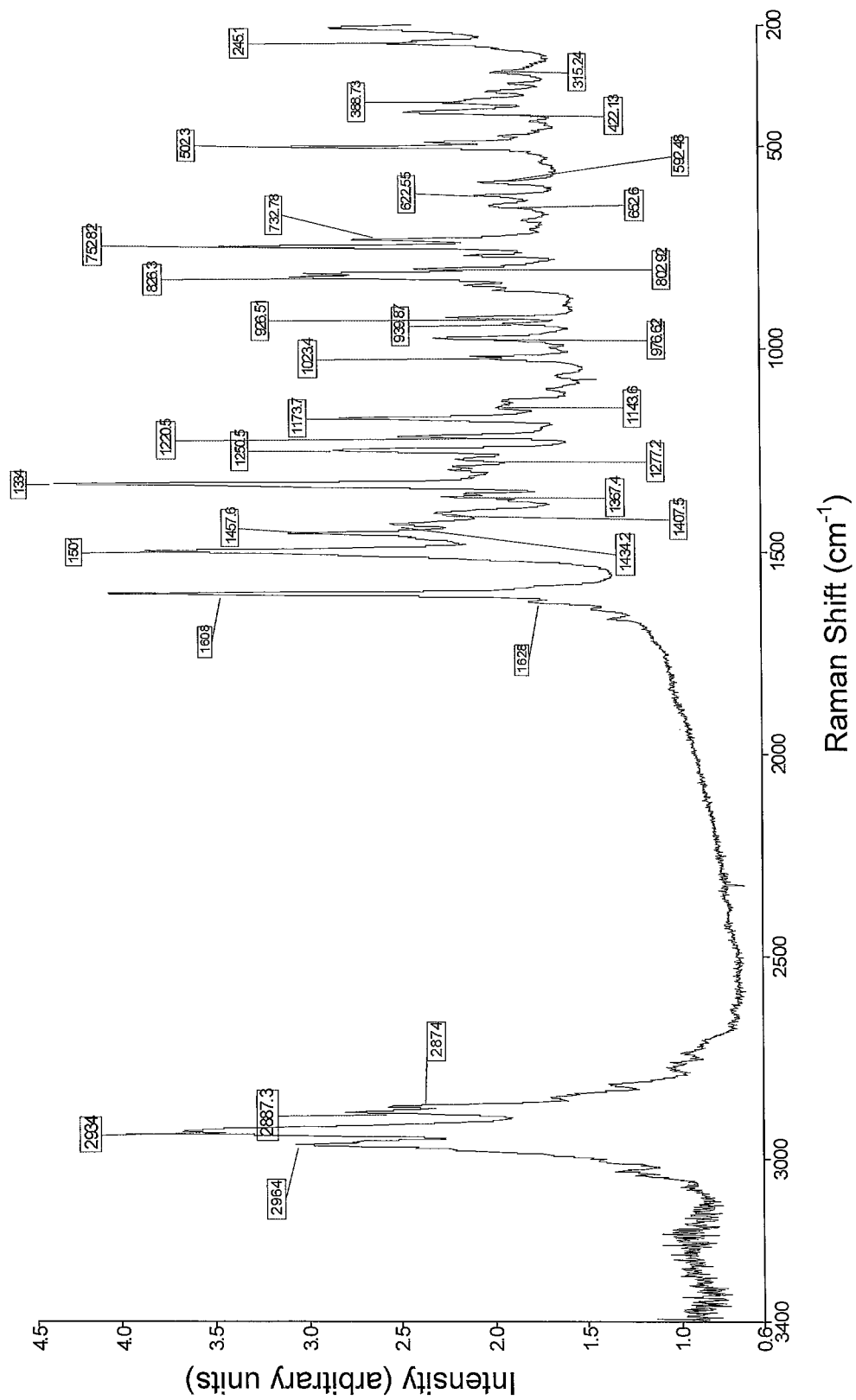
FIG. 23 shows the Raman spectrum of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine with peaks numerically identified.

Example 5: Process for the Synthesis of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine A reaction vessel was charged with 10 g of the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and 200 mL water. The slurry was stirred for 2-4 hours. The solid was isolated via filtration and dried on the filter for 1-2 hours to afford the crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine. The resulting solid exhibited the powder X-ray diffraction pattern displayed in FIGS. 17-18, and Table 5, the DSC and TGA displayed in FIGS. 19-20, the infrared spectrum displayed in FIG. 21 and the Raman spectra displayed in FIGS. 22-23.

TABLE 5

Peak listing for the X-ray powder diffractogram of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine

| Pos. [°2Th.] | Height [cts] | FWHM [°2Th.] | d-spacing [Å] | Rel. Int. [%] |
|---|---|---|---|---|
| 5.5630 | 690.13 | 0.0768 | 15.88671 | 4.00 |
| 8.3060 | 5435.10 | 0.0768 | 10.64530 | 31.51 |
| 10.0280 | 879.24 | 0.0768 | 8.82087 | 5.10 |
| 10.2012 | 893.49 | 0.0768 | 8.67151 | 5.18 |
| 10.5593 | 1995.84 | 0.1023 | 8.37818 | 11.57 |
| 11.0555 | 883.63 | 0.0768 | 8.00324 | 5.12 |
| 11.5183 | 320.77 | 0.1023 | 7.68270 | 1.86 |
| 11.8781 | 129.95 | 0.1279 | 7.45081 | 0.75 |
| 12.8085 | 69.41 | 0.1023 | 6.91160 | 0.40 |
| 13.6019 | 2957.43 | 0.1279 | 6.51016 | 17.14 |
| 14.0165 | 4349.92 | 0.1279 | 6.31852 | 25.22 |
| 14.3661 | 369.35 | 0.0768 | 6.16556 | 2.14 |
| 15.4007 | 633.14 | 0.1279 | 5.75361 | 3.67 |
| 15.9161 | 966.01 | 0.1023 | 5.56843 | 5.60 |
| 16.7238 | 2308.41 | 0.1279 | 5.30125 | 13.38 |
| 17.1424 | 1291.23 | 0.1279 | 5.17275 | 7.49 |
| 17.9407 | 17250.59 | 0.1791 | 4.94434 | 100.00 |
| 18.1017 | 7667.64 | 0.0512 | 4.90072 | 44.45 |
| 18.5141 | 1832.80 | 0.1279 | 4.79249 | 10.62 |
| 18.8004 | 1799.56 | 0.1279 | 4.72013 | 10.43 |
| 19.7326 | 1228.73 | 0.1535 | 4.49920 | 7.12 |
| 20.1720 | 765.07 | 0.1023 | 4.40217 | 4.44 |
| 20.4586 | 4099.20 | 0.1535 | 4.34116 | 23.76 |
| 21.0178 | 391.95 | 0.1023 | 4.22690 | 2.27 |
| 21.4381 | 355.28 | 0.1023 | 4.14498 | 2.06 |
| 21.6873 | 505.08 | 0.1535 | 4.09791 | 2.93 |
| 22.2036 | 553.03 | 0.1791 | 4.00377 | 3.21 |
| 22.7313 | 1258.93 | 0.1535 | 3.91200 | 7.30 |
| 23.1886 | 293.46 | 0.0768 | 3.83589 | 1.70 |
| 23.5022 | 802.91 | 0.1535 | 3.78540 | 4.65 |
| 23.9072 | 1323.54 | 0.1791 | 3.72219 | 7.67 |
| 24.8266 | 1308.18 | 0.1535 | 3.58638 | 7.58 |
| 25.3477 | 294.63 | 0.1279 | 3.51382 | 1.71 |
| 26.4001 | 712.70 | 0.1791 | 3.37610 | 4.13 |
| 27.2824 | 473.91 | 0.1791 | 3.26889 | 2.75 |
| 28.2575 | 1083.07 | 0.2047 | 3.15826 | 6.28 |
| 28.4360 | 661.36 | 0.1023 | 3.13884 | 3.83 |
| 29.0530 | 408.09 | 0.2303 | 3.07357 | 2.37 |
| 29.6230 | 525.69 | 0.2303 | 3.01572 | 3.05 |
| 30.3425 | 340.97 | 0.1535 | 2.94582 | 1.98 |
| 31.0351 | 150.13 | 0.1791 | 2.88164 | 0.87 |
| 32.0059 | 168.87 | 0.2047 | 2.79642 | 0.98 |
| 32.5007 | 33.40 | 0.2047 | 2.75497 | 0.19 |

TABLE 5-continued

Peak listing for the X-ray powder diffractogram of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine

| Pos. [°2Th.] | Height [cts] | FWHM [°2Th.] | d-spacing [Å] | Rel. Int. [%] |
|---|---|---|---|---|
| 33.2227 | 429.46 | 0.2047 | 2.69673 | 2.49 |
| 33.5621 | 380.49 | 0.1791 | 2.67024 | 2.21 |
| 34.7368 | 234.98 | 0.1535 | 2.58258 | 1.36 |

Figure 25:
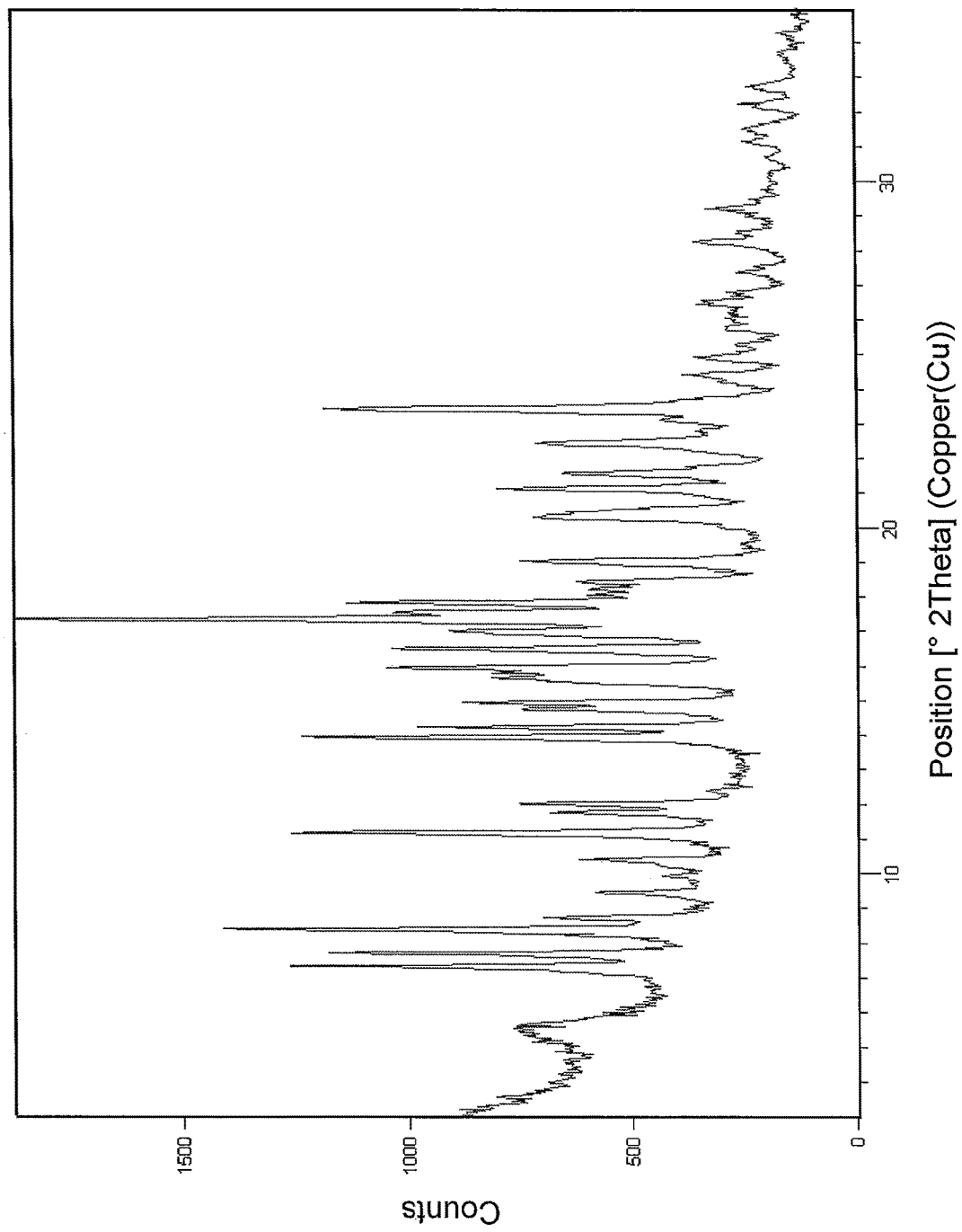
FIG. 25 shows the X-ray powder diffractogram of crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine without annotation.
Figure 29:
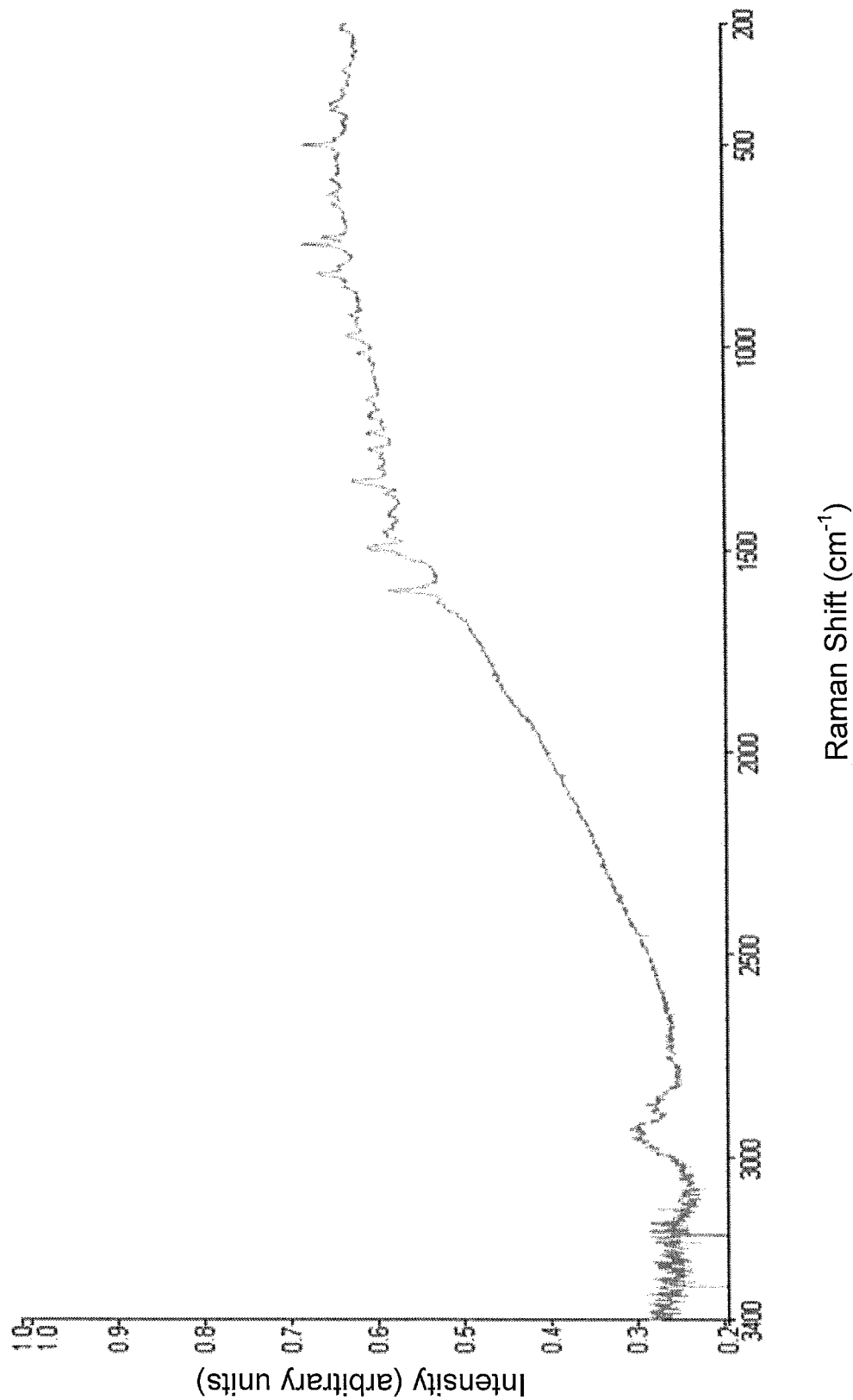
FIG. 29 shows the Raman spectrum of crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine without annotation.
Figure 30:
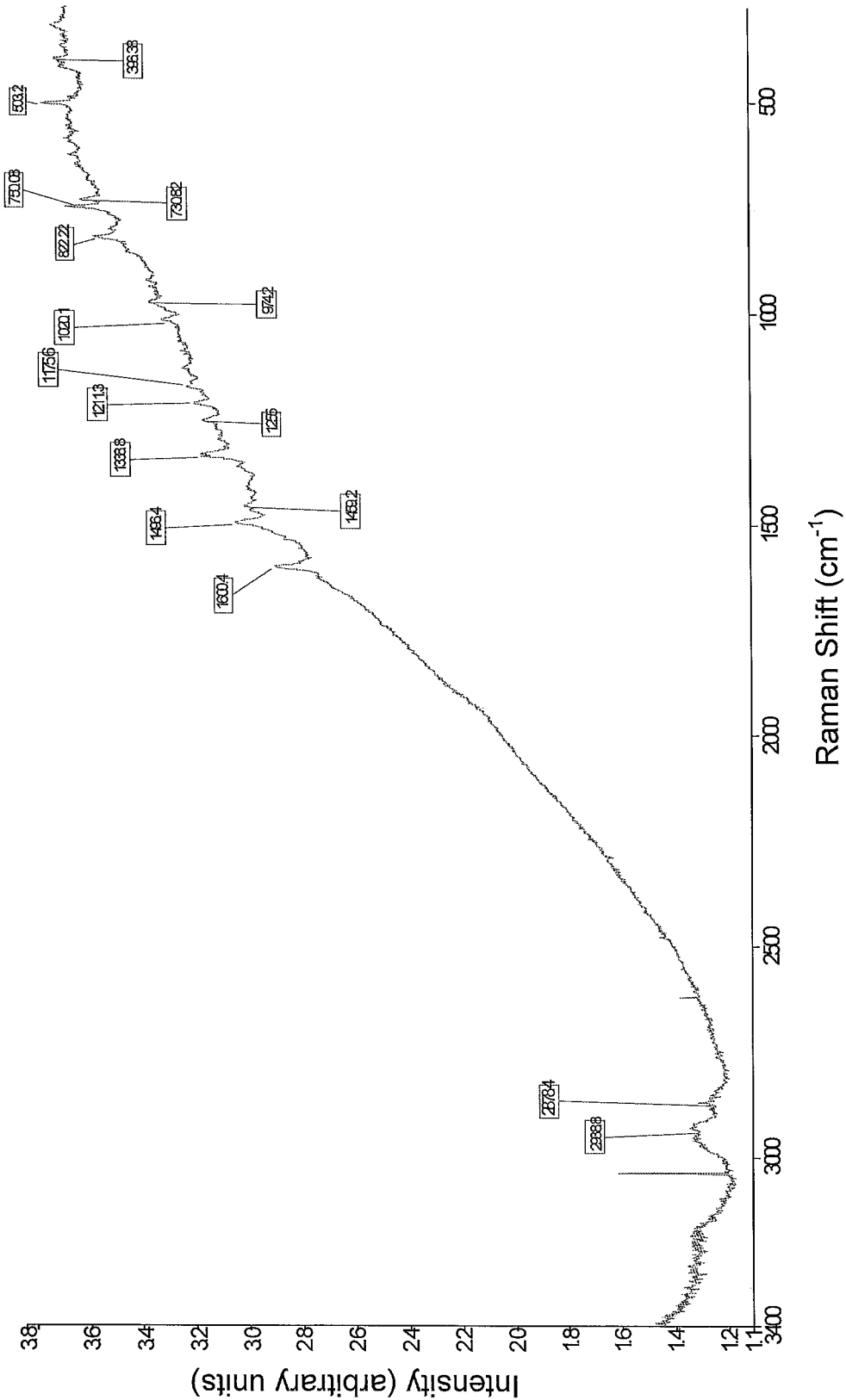
FIG. 30 shows the Raman spectrum of crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine with peaks numerically identified.

Example 6: Process for the Synthesis of crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine A reaction vessel was charged with 2 g of amorphous solid 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and 100 mL of water. The slurry was stirred and heated to 60° C. for 2 hours. The solid was isolated via hot filtration, yielding 1.12 g of material. The resulting solid exhibited the powder X-ray diffraction pattern displayed in FIGS. 24-25, and Table 6, the DSC and TGA displayed in FIGS. 26-27, the infrared spectrum displayed in FIG. 28 and the Raman spectra displayed in FIG. 29-30.

TABLE 6

Peak listing for the X-ray powder diffractogram of crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine

| Pos. [°2Th.] | Height [cts] | FWHM [°2Th.] | d-spacing [Å] | Rel. Int. [%] |
|---|---|---|---|---|
| 3.0992 | 198.60 | 0.2558 | 28.50850 | 11.88 |
| 5.6875 | 189.52 | 0.2047 | 15.53922 | 11.34 |
| 7.3367 | 875.84 | 0.0768 | 12.04940 | 52.39 |
| 7.7184 | 778.87 | 0.1023 | 11.45434 | 46.59 |
| 8.4128 | 1045.52 | 0.1023 | 10.51042 | 62.54 |
| 8.7352 | 312.43 | 0.1023 | 10.12329 | 18.69 |
| 9.4626 | 248.39 | 0.1023 | 9.34658 | 14.86 |
| 9.9438 | 107.95 | 0.0768 | 8.89539 | 6.46 |
| 10.4116 | 304.46 | 0.0768 | 8.49675 | 18.21 |
| 11.1849 | 956.96 | 0.1279 | 7.91093 | 57.24 |
| 11.7679 | 400.75 | 0.1023 | 7.52034 | 23.97 |
| 12.0141 | 476.70 | 0.0768 | 7.36678 | 28.51 |
| 12.3836 | 67.54 | 0.1023 | 7.14778 | 4.04 |
| 13.9488 | 988.27 | 0.1023 | 6.34902 | 59.11 |
| 14.2513 | 725.29 | 0.1023 | 6.21496 | 43.38 |
| 14.7487 | 496.69 | 0.0768 | 6.00643 | 29.71 |
| 14.9540 | 629.52 | 0.0768 | 5.92443 | 37.65 |
| 15.5148 | 364.82 | 0.0768 | 5.71154 | 21.82 |
| 15.6636 | 573.78 | 0.0768 | 5.65761 | 34.32 |
| 15.9816 | 749.15 | 0.1023 | 5.54573 | 44.81 |
| 16.5007 | 800.16 | 0.1023 | 5.37242 | 47.86 |
| 16.8936 | 504.28 | 0.0768 | 5.24835 | 30.16 |
| 17.0260 | 665.98 | 0.1023 | 5.20784 | 39.83 |
| 17.3416 | 1671.90 | 0.1023 | 5.11377 | 100.00 |
| 17.5649 | 802.14 | 0.1023 | 5.04927 | 47.98 |
| 17.8362 | 906.95 | 0.1279 | 4.97307 | 54.25 |
| 18.2227 | 372.06 | 0.0768 | 4.86846 | 22.25 |
| 18.4737 | 375.78 | 0.1279 | 4.80288 | 22.48 |
| 19.0459 | 485.98 | 0.1535 | 4.65984 | 29.07 |
| 20.2820 | 493.50 | 0.1535 | 4.37855 | 29.52 |
| 21.1457 | 568.45 | 0.1279 | 4.20162 | 34.00 |

TABLE 6-continued

Peak listing for the X-ray powder diffractogram of crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine

| Pos. [°2Th.] | Height [cts] | FWHM [°2Th.] | d-spacing [Å] | Rel. Int. [%] |
|---|---|---|---|---|
| 21.5774 | 457.90 | 0.1279 | 4.11853 | 27.39 |
| 22.4297 | 499.99 | 0.1535 | 3.96393 | 29.91 |
| 23.1183 | 241.96 | 0.1279 | 3.84739 | 14.47 |
| 23.4118 | 989.13 | 0.1535 | 3.79982 | 59.16 |
| 24.4459 | 153.39 | 0.1279 | 3.64138 | 9.17 |
| 24.9424 | 166.56 | 0.1791 | 3.57000 | 9.96 |
| 25.2820 | 92.01 | 0.1279 | 3.52281 | 5.50 |
| 25.7449 | 114.48 | 0.1023 | 3.46051 | 6.85 |
| 26.4916 | 169.99 | 0.1535 | 3.36464 | 10.17 |
| 26.7999 | 120.42 | 0.1535 | 3.32663 | 7.20 |
| 27.3858 | 101.08 | 0.0768 | 3.25677 | 6.05 |
| 28.2746 | 203.68 | 0.1279 | 3.15639 | 12.18 |
| 28.5404 | 104.74 | 0.1023 | 3.12760 | 6.27 |
| 29.2441 | 136.15 | 0.1023 | 3.05392 | 8.14 |
| 30.2344 | 48.05 | 0.2047 | 2.95611 | 2.87 |
| 30.6752 | 54.83 | 0.1791 | 2.91463 | 3.28 |
| 31.1253 | 108.48 | 0.1279 | 2.87350 | 6.49 |
| 31.5101 | 114.77 | 0.2047 | 2.83928 | 6.86 |
| 32.1968 | 98.33 | 0.2558 | 2.78027 | 5.88 |
| 32.7310 | 99.94 | 0.1023 | 2.73611 | 5.98 |
| 33.6855 | 47.23 | 0.1023 | 2.66074 | 2.83 |
| 34.2749 | 57.08 | 0.0768 | 2.61632 | 3.41 |

Figure 32:
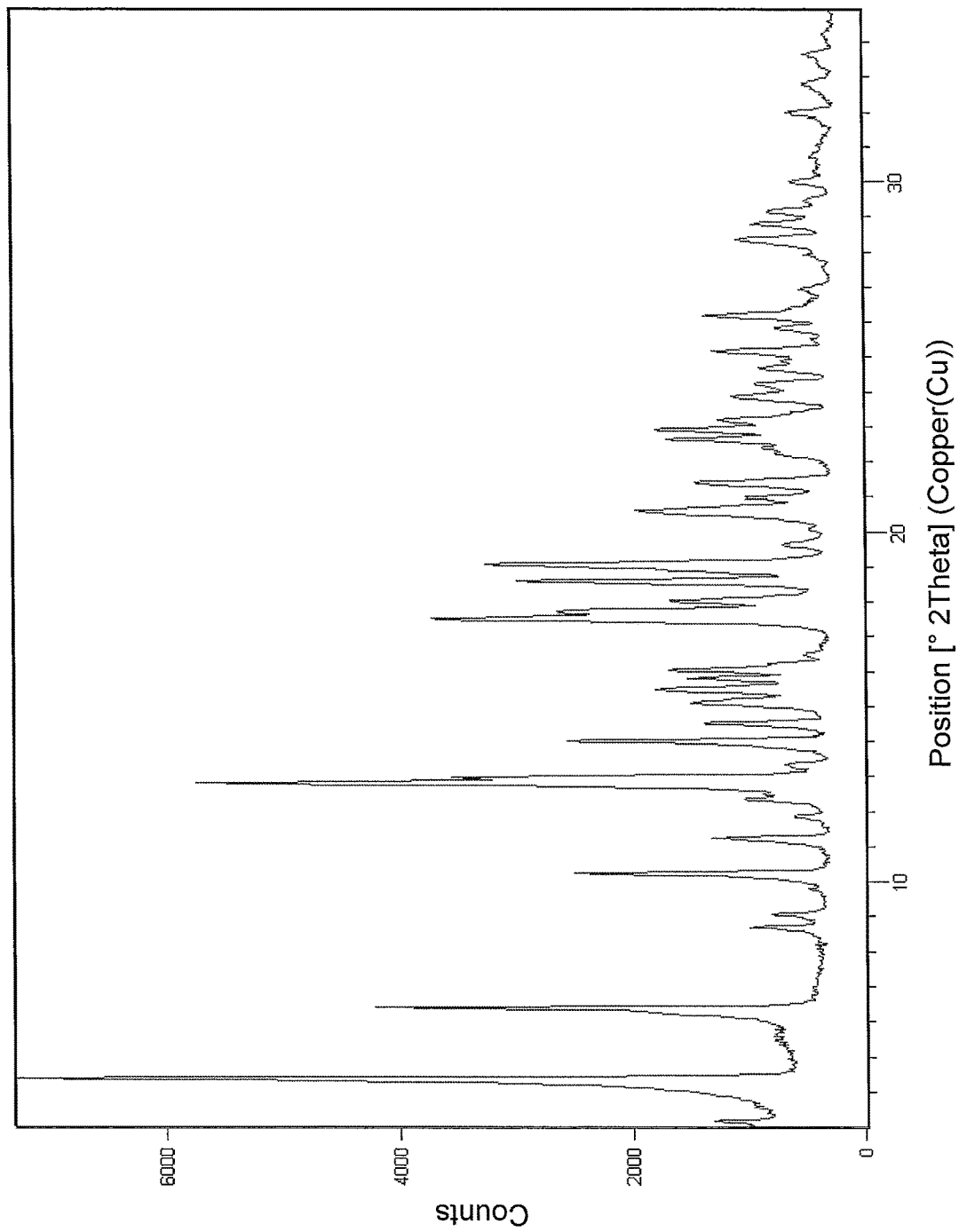
FIG. 32 shows the X-ray powder diffractogram of crystalline Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine without annotation.

Example 7: Process for the Synthesis of crystalline Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine A reaction vessel was charged with 1 g of amorphous solid 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and 20 mL of EtOH. The solution was stirred and heated to 60° C. for about 1 hour. The solution was held at 60° C. while nitrogen gas was passed over the solution, evaporating the solvent and concentrating the reaction mixture until crystallization began. The solution was then allowed to slowly cool overnight to afford crystalline material. The crystalline solid was isolated by filtration and dried at 55° C. The resulting solid exhibited the powder X-ray diffraction pattern displayed in FIGS. 31-32, and Table 7, and the DSC and TGA displayed in FIGS. 33-34.

TABLE 7

Peak listing for the X-ray powder diffractogram of crystalline Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine

| Pos. [°2Th.] | Height [cts] | FWHM [°2Th.] | d-spacing [Å] | Rel. Int. [%] |
|---|---|---|---|---|
| 3.1672 | 891.23 | 0.0768 | 27.89703 | 12.86 |
| 4.3834 | 6931.96 | 0.1023 | 20.15889 | 100.00 |
| 5.4897 | 330.94 | 0.2047 | 16.09860 | 4.77 |
| 6.2044 | 1288.01 | 0.0512 | 14.24578 | 18.58 |
| 6.3899 | 3790.66 | 0.1023 | 13.83258 | 54.68 |
| 8.6938 | 607.37 | 0.1023 | 10.17139 | 8.76 |
| 9.0652 | 444.30 | 0.1023 | 9.75546 | 6.41 |
| 9.7777 | 119.45 | 0.0768 | 9.04615 | 1.72 |
| 10.2389 | 2157.07 | 0.1023 | 8.63965 | 31.12 |

TABLE 7-continued

Peak listing for the X-ray powder diffractogram of crystalline Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine

| Pos. [°2Th.] | Height [cts] | FWHM [°2Th.] | d-spacing [Å] | Rel. Int. [%] |
|---|---|---|---|---|
| 11.2467 | 983.77 | 0.1279 | 7.86760 | 14.19 |
| 11.8707 | 278.59 | 0.1279 | 7.45540 | 4.02 |
| 12.3338 | 692.41 | 0.1023 | 7.17652 | 9.99 |
| 12.8049 | 5399.63 | 0.1023 | 6.91351 | 77.89 |
| 12.9862 | 3094.86 | 0.0768 | 6.81741 | 44.65 |
| 13.3662 | 354.08 | 0.1535 | 6.62445 | 5.11 |
| 14.0133 | 2211.62 | 0.1023 | 6.31995 | 31.90 |
| 14.5229 | 1052.58 | 0.1279 | 6.09933 | 15.18 |
| 15.0822 | 1158.80 | 0.1791 | 5.87436 | 16.72 |
| 15.4766 | 1477.85 | 0.1535 | 5.72554 | 21.32 |
| 15.7997 | 1205.59 | 0.1023 | 5.60917 | 17.39 |
| 16.0464 | 1349.02 | 0.1023 | 5.52348 | 19.46 |
| 16.4905 | 188.08 | 0.1279 | 5.37572 | 2.71 |
| 17.4901 | 3355.74 | 0.1535 | 5.07068 | 48.41 |
| 17.7745 | 2248.51 | 0.1023 | 4.99018 | 32.44 |
| 18.0179 | 1355.40 | 0.1279 | 4.92333 | 19.55 |
| 18.6063 | 2679.28 | 0.1279 | 4.76894 | 38.65 |
| 18.8665 | 1133.73 | 0.0512 | 4.70376 | 16.36 |
| 19.0860 | 2899.34 | 0.1535 | 4.65015 | 41.83 |
| 19.6262 | 404.17 | 0.1279 | 4.52335 | 5.83 |
| 20.0698 | 166.76 | 0.1023 | 4.42436 | 2.41 |
| 20.5929 | 1626.38 | 0.2047 | 4.31314 | 23.46 |
| 20.9838 | 697.62 | 0.1279 | 4.23367 | 10.06 |
| 21.4061 | 1154.31 | 0.1791 | 4.15110 | 16.65 |
| 22.2105 | 447.69 | 0.1023 | 4.00254 | 6.46 |
| 22.3974 | 577.13 | 0.0512 | 3.96956 | 8.33 |
| 22.6356 | 1403.27 | 0.1023 | 3.92833 | 20.24 |
| 22.9179 | 1502.49 | 0.1279 | 3.88057 | 21.67 |
| 23.2023 | 963.24 | 0.1279 | 3.83365 | 13.90 |
| 23.8591 | 843.13 | 0.2047 | 3.72959 | 12.16 |
| 24.2484 | 611.50 | 0.1279 | 3.67058 | 8.82 |
| 24.6862 | 603.74 | 0.1535 | 3.60647 | 8.71 |
| 25.1765 | 973.86 | 0.1791 | 3.53733 | 14.05 |
| 25.5023 | 143.35 | 0.0768 | 3.49288 | 2.07 |
| 25.8431 | 470.21 | 0.1791 | 3.44758 | 6.78 |
| 26.1733 | 1089.43 | 0.1535 | 3.40483 | 15.72 |
| 26.9377 | 271.79 | 0.1023 | 3.30992 | 3.92 |
| 27.5800 | 57.80 | 0.1535 | 3.23428 | 0.83 |
| 27.9121 | 231.35 | 0.0768 | 3.19656 | 3.34 |
| 28.3654 | 786.82 | 0.1535 | 3.14649 | 11.35 |
| 28.8139 | 643.08 | 0.1535 | 3.09853 | 9.28 |
| 29.1637 | 527.47 | 0.1535 | 3.06216 | 7.61 |
| 29.4832 | 211.62 | 0.1023 | 3.02969 | 3.05 |
| 29.9991 | 354.99 | 0.1535 | 2.97876 | 5.12 |
| 30.7636 | 157.51 | 0.1535 | 2.90645 | 2.27 |
| 31.9908 | 376.81 | 0.1279 | 2.79771 | 5.44 |
| 32.8014 | 249.45 | 0.1279 | 2.73040 | 3.60 |
| 33.6788 | 195.64 | 0.1279 | 2.66125 | 2.82 |
| 34.2423 | 74.36 | 0.1535 | 2.61873 | 1.07 |

TABLE 8

Peak listing for the X-ray powder diffractogram of crystalline Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine

| Pos. [°2Th.] | Height [cts] | FWHM [°2Th.] | d-spacing [Å] | Rel. Int. [%] |
|---|---|---|---|---|
| 3.0930 | 922.45 | 0.0768 | 28.56528 | 16.01 |
| 3.4623 | 858.41 | 0.0768 | 25.51979 | 14.90 |
| 3.7214 | 1002.49 | 0.0768 | 23.74331 | 17.40 |
| 4.3050 | 5761.00 | 0.0768 | 20.52571 | 100.00 |
| 4.8848 | 1042.74 | 0.1279 | 18.09080 | 18.10 |
| 5.2922 | 1027.76 | 0.0768 | 16.69897 | 17.84 |
| 5.7296 | 574.24 | 0.1023 | 15.42521 | 9.97 |
| 6.2279 | 612.97 | 0.1279 | 14.19205 | 10.64 |
| 6.9617 | 246.22 | 0.0512 | 12.69760 | 4.27 |
| 7.5776 | 83.70 | 0.3070 | 11.66691 | 1.45 |
| 10.0012 | 598.63 | 0.0768 | 8.84447 | 10.39 |
| 10.4954 | 192.91 | 0.1279 | 8.42909 | 3.35 |
| 10.6820 | 215.23 | 0.0768 | 8.28224 | 3.74 |
| 11.1198 | 766.71 | 0.0768 | 7.95716 | 13.31 |
| 11.6640 | 336.86 | 0.1023 | 7.58707 | 5.85 |
| 12.2039 | 196.89 | 0.0768 | 7.25259 | 3.42 |
| 12.5522 | 951.49 | 0.1023 | 7.05214 | 16.52 |
| 12.8646 | 1197.30 | 0.1279 | 6.88159 | 20.78 |
| 13.1130 | 2313.45 | 0.0768 | 6.75176 | 40.16 |
| 13.2878 | 1134.51 | 0.0768 | 6.66336 | 19.69 |
| 14.1311 | 1182.73 | 0.1023 | 6.26753 | 20.53 |
| 14.4939 | 257.96 | 0.0768 | 6.11148 | 4.48 |
| 14.7071 | 278.75 | 0.1023 | 6.02336 | 4.84 |
| 15.3319 | 587.84 | 0.1023 | 5.77925 | 10.20 |
| 15.9237 | 506.90 | 0.1535 | 5.56579 | 8.80 |
| 16.7038 | 853.13 | 0.2303 | 5.30756 | 14.81 |
| 17.5492 | 645.84 | 0.0768 | 5.05375 | 11.21 |
| 17.7443 | 1462.08 | 0.1279 | 4.99862 | 25.38 |
| 18.0546 | 1168.83 | 0.2047 | 4.91340 | 20.29 |
| 18.8622 | 2263.23 | 0.1279 | 4.70480 | 39.29 |
| 19.6876 | 180.88 | 0.1279 | 4.50938 | 3.14 |
| 20.1549 | 279.92 | 0.1279 | 4.40589 | 4.86 |
| 20.5942 | 234.25 | 0.1023 | 4.31288 | 4.07 |
| 21.5782 | 216.48 | 0.3070 | 4.11838 | 3.76 |
| 22.3720 | 529.04 | 0.1279 | 3.97401 | 9.18 |
| 22.6009 | 318.28 | 0.0768 | 3.93428 | 5.52 |
| 22.9708 | 146.62 | 0.1279 | 3.87175 | 2.55 |
| 23.2981 | 128.68 | 0.1023 | 3.81809 | 2.23 |
| 23.7100 | 347.34 | 0.1791 | 3.75269 | 6.03 |
| 23.9304 | 351.85 | 0.0768 | 3.71862 | 6.11 |
| 24.6578 | 70.05 | 0.1535 | 3.61055 | 1.22 |
| 25.2428 | 359.68 | 0.1023 | 3.52819 | 6.24 |
| 26.8677 | 185.62 | 0.1023 | 3.31839 | 3.22 |
| 28.1046 | 131.15 | 0.2047 | 3.17510 | 2.28 |
| 28.4386 | 112.67 | 0.1279 | 3.13857 | 1.96 |
| 29.9739 | 88.40 | 0.1535 | 2.98121 | 1.53 |
| 30.4594 | 49.98 | 0.1279 | 2.93478 | 0.87 |
| 31.8405 | 22.73 | 0.1791 | 2.81057 | 0.39 |
| 32.6315 | 56.01 | 0.3070 | 2.74423 | 0.97 |

Figure 36:
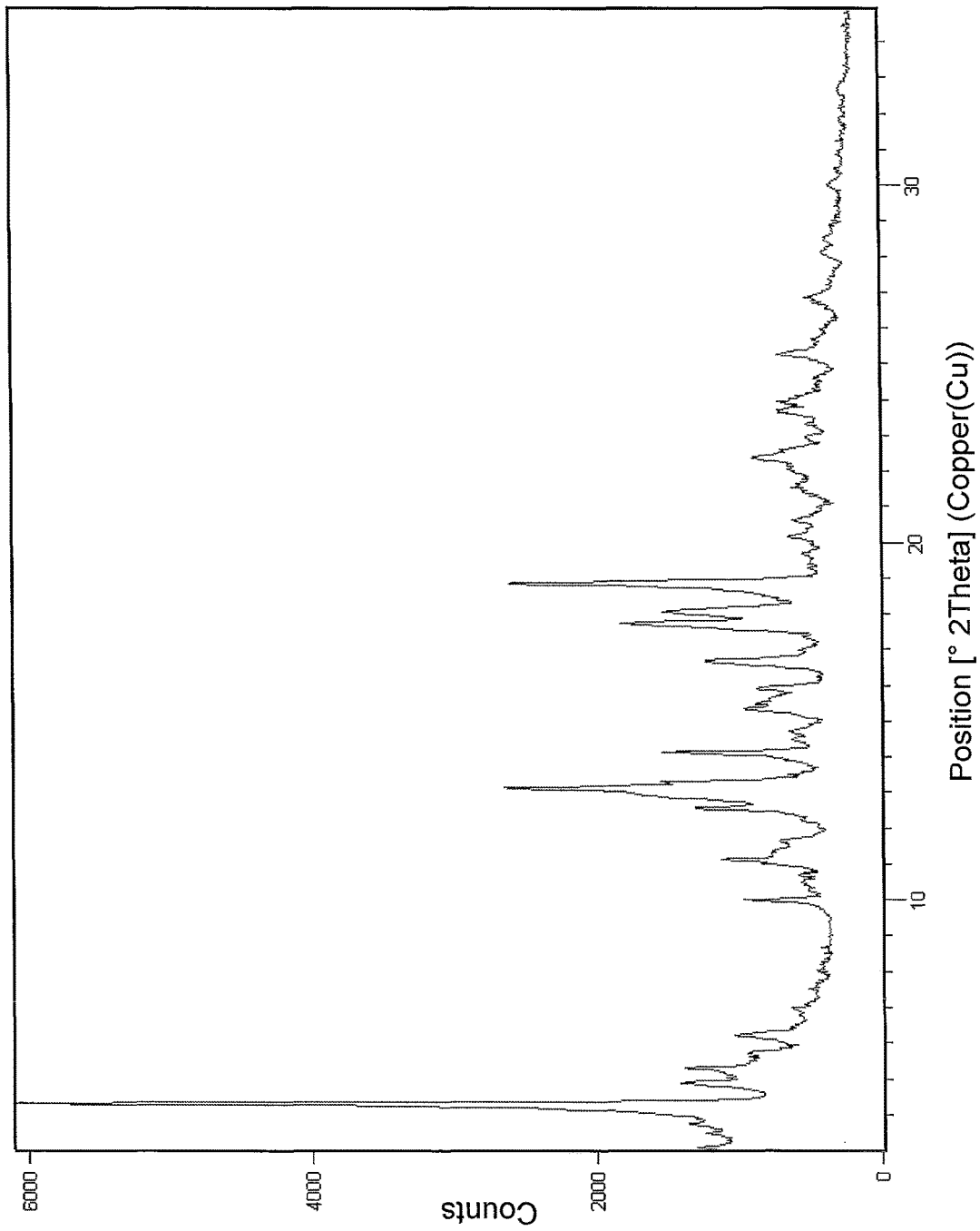
FIG. 36 shows the X-ray powder diffractogram of crystalline Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine without annotation.

Example 8: Process for the Synthesis of crystalline Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine A reaction vessel was charged with 1 g of amorphous solid 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and 14 mL of $CH_3CN$. The suspension was stirred and heated to 80° C. for 5 hours. The solid was isolated via hot filtration and dried at 55° C. The resulting solid exhibited the powder X-ray diffraction pattern displayed in FIGS. 35-36, and Table 8, and the DSC and TGA displayed in FIGS. 37-38.

Example 9: Process for the Synthesis of crystalline Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine A reaction vessel was charged with 1 g of amorphous solid 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine and 50 mL of $Et_2O$. The suspension was stirred and heated to 30° C. for 5 hours. The solid was isolated via hot filtration and dried at 55° C.

Figure 40:
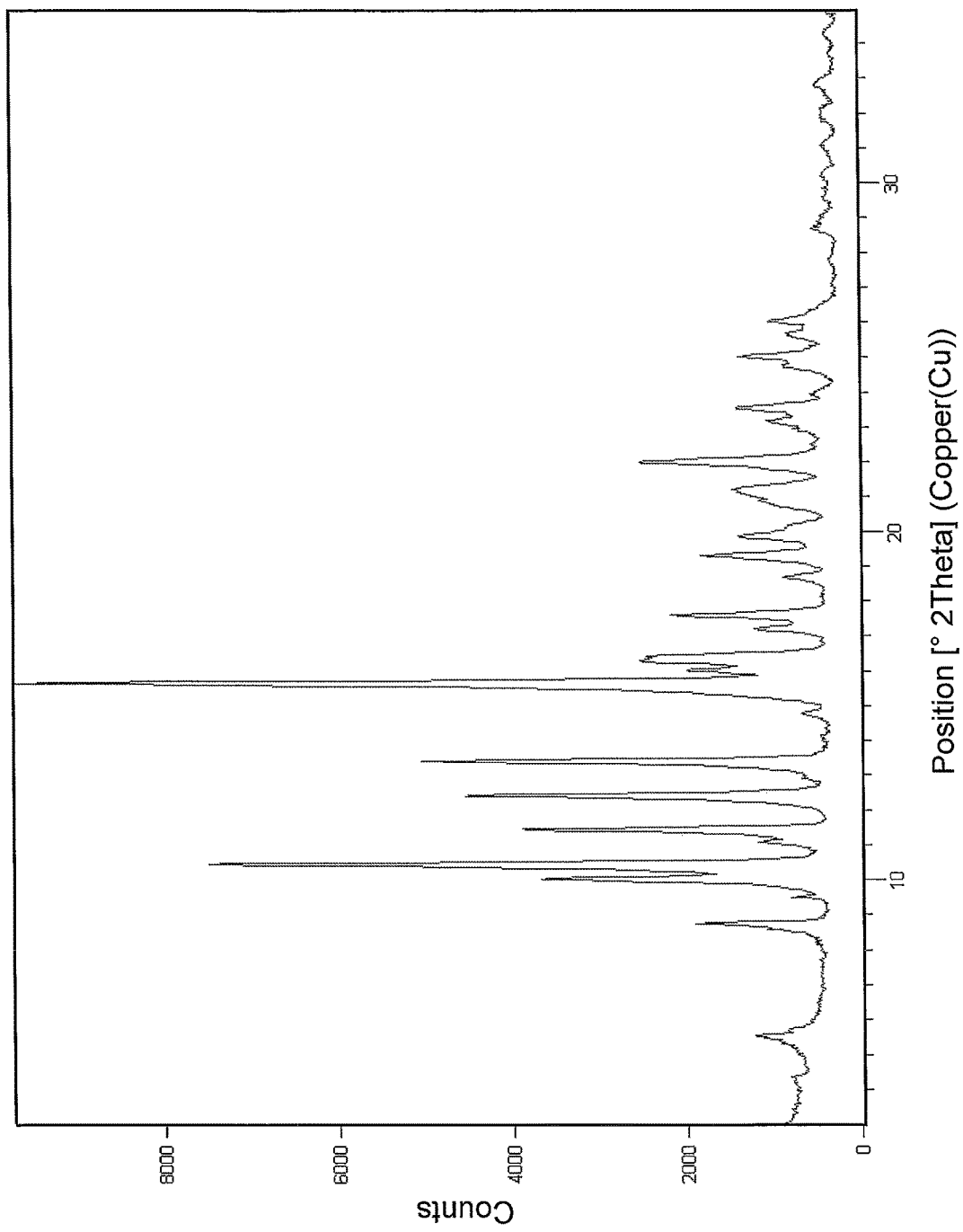
FIG. 40 shows the X-ray powder diffractogram of crystalline Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine without annotation.

An alternative preparation of the crystalline solid of Form I was achieved by charging a reaction vessel with 1 g of amorphous solid 5-{[(2S,5R)-2,5-dimethyl-4-(tetrahydro-2H-pyran-4-ylmethyl)piperazin-1-yl]carbonyl}-N-(5- fluoro-2-methylpyrimidin-4-yl)-6,6-dimethyl-1,4,5,6-tetrahydropyrrolo[3,4-c]pyrazol-3-amine and 50 mL of methyl ethyl ketone. The solution was stirred and heated to 60° C. for about 1 hour. The solution was held at 60° C. while nitrogen gas was passed over the solution, evaporating the solvent and concentrating the reaction mixture until crystallization began. The solution was then allowed to slowly cool overnight to afford crystalline material. The solid was isolated by filtration and dried at 55° C. The resulting solids from both preparations exhibited the powder X-ray diffraction pattern displayed in FIGS. 39-40, and Table 9, and the DSC and TGA displayed in FIGS. 41-42.

TABLE 9

Peak listing for the X-ray powder diffractogram of crystalline Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine

| Pos. [°2Th.] | Height [cts] | FWHM [°2Th.] | d-spacing [Å] | Rel. Int. [%] |
|---|---|---|---|---|
| 4.0731 | 43.01 | 0.4093 | 21.69391 | 0.46 |
| 4.3427 | 115.06 | 0.0768 | 20.34782 | 1.23 |
| 5.5083 | 656.95 | 0.0768 | 16.04437 | 7.04 |
| 5.7151 | 275.84 | 0.0768 | 15.46416 | 2.96 |
| 6.7017 | 12.46 | 0.3070 | 13.18967 | 0.13 |
| 8.7564 | 1484.80 | 0.1023 | 10.09883 | 15.92 |
| 9.5087 | 388.35 | 0.0512 | 9.30142 | 4.16 |
| 10.0391 | 3286.18 | 0.1279 | 8.81113 | 35.23 |
| 10.4596 | 7112.00 | 0.1279 | 8.45783 | 76.24 |
| 11.0863 | 795.84 | 0.0768 | 7.98112 | 8.53 |
| 11.4510 | 3567.88 | 0.1279 | 7.72771 | 38.25 |
| 12.4105 | 4192.64 | 0.1279 | 7.13235 | 44.94 |
| 12.8969 | 249.53 | 0.0768 | 6.86441 | 2.67 |
| 13.4212 | 4726.90 | 0.1279 | 6.59742 | 50.67 |
| 14.0940 | 63.40 | 0.1535 | 6.28394 | 0.68 |
| 14.7950 | 312.95 | 0.1279 | 5.98775 | 3.35 |
| 15.6550 | 9328.88 | 0.1279 | 5.66069 | 100.00 |
| 16.0269 | 1638.18 | 0.0768 | 5.53019 | 17.56 |
| 16.2734 | 2146.72 | 0.0768 | 5.44696 | 23.01 |
| 16.4440 | 1924.64 | 0.1279 | 5.39085 | 20.63 |
| 17.2048 | 861.47 | 0.1279 | 5.15412 | 9.23 |
| 17.5888 | 1822.40 | 0.1279 | 5.04246 | 19.54 |
| 18.7002 | 514.07 | 0.1535 | 4.74519 | 5.51 |
| 19.3264 | 1490.04 | 0.2047 | 4.59284 | 15.97 |
| 19.8539 | 1061.34 | 0.1279 | 4.47199 | 11.38 |
| 20.1935 | 464.22 | 0.1535 | 4.39754 | 4.98 |
| 20.7352 | 609.58 | 0.1535 | 4.28388 | 6.53 |
| 21.2813 | 1028.46 | 0.2303 | 4.17516 | 11.02 |
| 21.9984 | 2223.41 | 0.1791 | 4.04065 | 23.83 |
| 23.1627 | 715.41 | 0.1535 | 3.84011 | 7.67 |
| 23.5262 | 1103.15 | 0.2047 | 3.78160 | 11.83 |
| 23.9307 | 211.75 | 0.0768 | 3.71858 | 2.27 |
| 24.7383 | 571.53 | 0.1279 | 3.59899 | 6.13 |
| 25.0316 | 1089.44 | 0.1279 | 3.55749 | 11.68 |
| 25.6969 | 540.10 | 0.1791 | 3.46687 | 5.79 |
| 26.0210 | 751.12 | 0.1279 | 3.42441 | 8.05 |
| 27.1503 | 20.59 | 0.1535 | 3.28449 | 0.22 |
| 27.7785 | 64.82 | 0.1535 | 3.21162 | 0.69 |
| 28.6746 | 214.56 | 0.1535 | 3.11327 | 2.30 |

Pharmaceutical Dosage Forms

Example 10: A tablet is prepared by mixing 48% by weight of amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

Example 11: A tablet is prepared by mixing 48% by weight of crystalline hydrate Form B of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, 40% by weight of microcrystalline cellulose, 5% by weight of low-substituted hydroxypropyl cellulose, 5% by weight of croscarmellose sodium, and 2% by weight of magnesium stearate. Tablets are prepared by direct compression. The total weight of the compressed tablets is maintained at 250-500 mg.

Example 12: A tablet is prepared by mixing 48% by weight of crystalline hydrate Form D of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

Example 13: A tablet is prepared by mixing 48% by weight of crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, 40% by weight of microcrystalline cellulose, 5% by weight of low-substituted hydroxypropyl cellulose, 5% by weight of croscarmellose sodium, and 2% by weight of magnesium stearate. Tablets are prepared by direct compression. The total weight of the compressed tablets is maintained at 250-500 mg.

Example 14: A tablet is prepared by mixing 48% by weight of crystalline Form G of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, 40% by weight of microcrystalline cellulose, 5% by weight of low-substituted hydroxypropyl cellulose, 5% by weight of croscarmellose sodium, and 2% by weight of magnesium stearate. Tablets are prepared by direct compression. The total weight of the compressed tablets is maintained at 250-500 mg.

Example 15: A tablet is prepared by mixing 48% by weight of crystalline Form H of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, 40% by weight of microcrystalline cellulose, 5% by weight of low-substituted hydroxypropyl cellulose, 5% by weight of croscarmellose sodium, and 2% by weight of magnesium stearate. Tablets are prepared by direct compression. The total weight of the compressed tablets is maintained at 250-500 mg.

Example 16: A tablet is prepared by mixing 48% by weight of crystalline Form I of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, 40% by weight of microcrystalline cellulose, 5% by weight of low-substituted hydroxypropyl cellulose, 5% by weight of croscarmellose sodium, and 2% by weight of magnesium stearate. Tablets are prepared by direct compression. The total weight of the compressed tablets is maintained at 250-500 mg.

Treatment of Uveitis

Example 17: Evaluate the efficacy and safety of amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine in subjects with Uveitis Study design: Allocation: randomized
Endpoint Classification: Safety/Efficacy Study
Intervention Model: Parallel Assignment
Masking: Double Blind (Subject, Caregiver, Investigator, Outcomes Assessor)
Primary Purpose: Treatment
Primary Outcome Measures:
Control of intraocular inflammation [Time Frame: at 6-month visit] [Designated as safety issue: No]
Absence of intraocular inflammation (e.g. less than trace AC cells; no vitreous haze; inactive chorioretinal lesions).
Evaluation of Adverse Events [Time Frame: Baseline to Final Visit (Final Visit could occur at any point up to 52 weeks)][Designated as safety issue: Yes]
Significant laboratory value changes [Time Frame: Baseline to Final Visit (Final Visit could occur at any point up to 52 weeks)] [Designated as safety issue: Yes]
Significant vital sign changes [Time Frame: Baseline to Final Visit (Final Visit could occur at any point up to 52 weeks)] [Designated as safety issue: Yes]
Secondary Outcome Measures:
Control of intraocular inflammation [Time Frame: 12-month clinical visit] [Designated as safety issue: No]
Proportion of subjects at each study time point with no new active, inflammatory chorioretinal or inflammatory retinal vascular lesion in both eyes relative to Baseline for subjects who had inactive uveitis when they entered the study. [Time Frame: Final Visit (Final Visit could occur at any point up to 52 weeks)] [Designated as safety issue: No]
Proportion of subjects at each study time point with no new active, inflammatory chorioretinal or inflammatory retinal vascular lesion in both eyes relative to Week 8 for subjects who had active uveitis when they entered the study. [Time Frame: Final Visit (Final Visit could occur at any point up to 52 weeks)] [Designated as safety issue: No]
Proportion of subjects at each study time point with a Grade<=0.5+in AC cells in both eyes on Slit Lamp Exam according to SUN criteria. [Time Frame: Final Visit (Final Visit could occur at any point up to 52 weeks)] [Designated as safety issue: No]
Proportion of subjects at each study time point with a Grade<=0.5+in vitreous haze in both eyes on indirect ophthalmoscopy according to NEVSUN criteria. [Time Frame: Final Visit (Final Visit could occur at any point up to 52 weeks)][Designated as safety issue: No]
Proportion of subjects at each study time point without a worsening of BCVA by >=15 letters on the ETDRS in both eyes relative to Baseline for subjects who had inactive uveitis when they entered the study. [Time Frame: Final Visit (Final Visit could occur at any point up to 52 weeks)] [Designated as safety issue: No]
Proportion of subjects at each study time point without a worsening of BCVA by >=15 letters on the ETDRS in both eyes relative to Week 8 for subjects who had active uveitis when they entered the study. [Time Frame: Final Visit (Final Visit could occur at any point up to 52 weeks)] [Designated as safety issue: No]
Percent change in central retinal thickness (1 mm subfield) in each eye at each study time point relative to Baseline for subjects who had inactive uveitis when they entered the study. [Time Frame: Baseline to Final Visit (Final Visit could occur at any point up to 52 weeks)] [Designated as safety issue: No]
Percent change in central retinal thickness (1 mm subfield) in each eye at each study time point relative to Week 8 for subjects who had active uveitis when they entered the study. [Time Frame: Week 8 to Final Visit (Final Visit could occur at any point up to 52 weeks)] [Designated as safety issue: No]
Change in NEI Visual Functioning Questionnaire (VFQ-25) score at each study time point relative to Baseline for subjects who had inactive uveitis when they entered the study. [Time Frame: Baseline to Final Visit (Final Visit could occur at any point up to 52 weeks)] [Designated as safety issue: No]
Change in NEI Visual Functioning Questionnaire (VFQ-25) score at each study time point relative to week 8 for subjects who had active uveitis when they entered the study. [Time Frame: Week 8 to Final Visit (Final Visit could occur at any point up to 52 weeks)] [Designated as safety issue: No]
Proportion of subjects at each study time point achieving a >=50% reduction in immunosuppression load relative to Baseline for subjects who had inactive uveitis when they entered the study. [Time Frame: Final Visit (Final Visit could occur at any point up to 52 weeks)] [Designated as safety issue: No]
Proportion of subjects at each study time point achieving a >=50% reduction in immunosuppression load relative to Week 8 for subjects who had active uveitis when they entered the study. [Time Frame: Final Visit (Final Visit could occur at any point up to 52 weeks)] [Designated as safety issue: No]
Other Outcome Measures:
Elevation of TOP [Time Frame: At 3-month, 6-month, and 12-month visit] [Designated as safety issue: Yes]
Ocular hypertension and IOP>30 and 10 mm Hg increase or greater in TOP will be assessed.
Progression of cataract or need for cataract surgery [Time Frame: At 3-month, 6-month, and 12-month visit] [Designated as safety issue: Yes]

| Arms | Assigned Interventions |
|---|---|
| Experimental: amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine Low-dose Group. Amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine will be given at the predetermined dosing intervals as specified in the protocol | Low dose of amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo [3,4-c]pyrazol-3-amine administered at the predetermined intervals |

| Arms | Assigned Interventions |
|---|---|
| Experimental: amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine High-dose Group. Amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine will be given at the predetermined dosing intervals as specified in the protocol | High dose of amorphous 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine administered at predetermined intervals |
| Placebo Comparator: Matching Placebo Group Placebo matching experimental dose will be given at the predetermined dosing intervals as specified in the protocol | Other: Placebo Matching placebo to experimental dose administered at predetermined intervals |

DETAILED DESCRIPTION

Background: Intermediate and posterior uveitis are known to induce severe intraocular inflammation that may lead to permanent visual loss. It is estimated that these forms of uveitis comprise the fifth or sixth leading cause of blindness and tend to affect working class age patients, thus causing loss of work hours and diminished productivity and quality of life. Because disease in the posterior segment of the eye is not adequately treated by corticosteroid drops often systemic drug therapy is used including oral corticosteroids or prednisone. Prednisone can have a myriad of side effects. In approximately one-quarter to one-third of cases treated in tertiary care centers, additional medications such as immunosuppressive drugs are required to control the disease and/or to allow for appropriate tapering of oral prednisone to subsequent levels that have a low side effect profile when delivered over a long period of time. Typically, chronic prednisone therapy in doses of 7.5 mg daily or less are thought to have a low enough side effect profile to be amenable to long-term therapy. However frequently additional immunosuppressive drugs are required to get the dosing to this level. There are occasions when patients are intolerant of any dose of oral corticosteroids or are intolerant of the higher doses of oral corticosteroids (30-60 mg daily) and therefore this treatment modality is avoided due to prednisone's attendant side effects. Although periocular and intravitreal corticosteroids injections may be performed, with these modalities the standard of care is to wait until the disease reactivates before instituting such therapy and therefore a chronic suppressive dose is not obtained. The fluocinolone acetonide implant (Retisert®, Bausch and Lomb, Tampa, Fla.) is FDA-approved for the treatment of intermediate and posterior uveitis and it is equally effective in controlling uveitis as high-dose oral corticosteroids but avoids the systemic side effects associated with the use of high doses of oral corticosteroids. However, this form of local therapy has high rates of ocular side effects, including ocular hypertension causing glaucoma and/or requiring glaucoma surgery and cataracts. Furthermore, every two and half to three years the implant is exhausted of corticosteroid and therefore repeat surgical insertion of another implant may be required.

Eligibility
Ages Eligible for Study: 18 Years and older
Gender Eligible for Study: Both
Accepts Healthy Volunteers: No
Inclusion Criteria:
Active sight-threatening intermediate or posterior uveitis.
Patients must be age 18 years or older and sign an informed consent.
The ocular media must be clear enough to obtain OCT and fundus photographs.
No elective intraocular surgery should be planned for the first 3 months after enrollment.
Exclusion Criteria:
Infectious uveitis
History of scleritis
Active or suspected viral infection of the cornea or conjunctiva
History of mycobacterial or fungal disease
HIV positivity
Age <18 years old
Uncontrolled IOP
Advanced glaucoma
Aphakia with rupture of the posterior lens capsule
ACIOL with rupture of the posterior lens capsule
Media opacity that would preclude evaluation of the posterior pole via fundus photography or OCT assessment
Planned elective ocular surgery within 3 months of enrollment
Additional Experiments Example 18: HPLC Isolation of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine Aims and Objectives
To assess the propensity of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine to form amorphous or crystalline phases following isolation from a $CH_3CN$/water eluent system, post transit/purification via a C18 reverse phase column.

Summary
Isolation of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine using acetonitrile ($CH_3CN$) and water systems provided varied results.

Three trials were completed:

| | |
|---|---|
| 18A | $CH_3CN$ |
| 18B | $CH_3CN$/water (9:1) |
| 18C | $CH_3CN$/water (1:9) |

The trial using CH₃CN provided an amorphous solid. The two wet systems provided either partially crystalline or highly crystalline solids in the form of Pattern L. The crystalline phases did not dry back to amorphous solids.

Characterization of Input Solid

Figure 43:
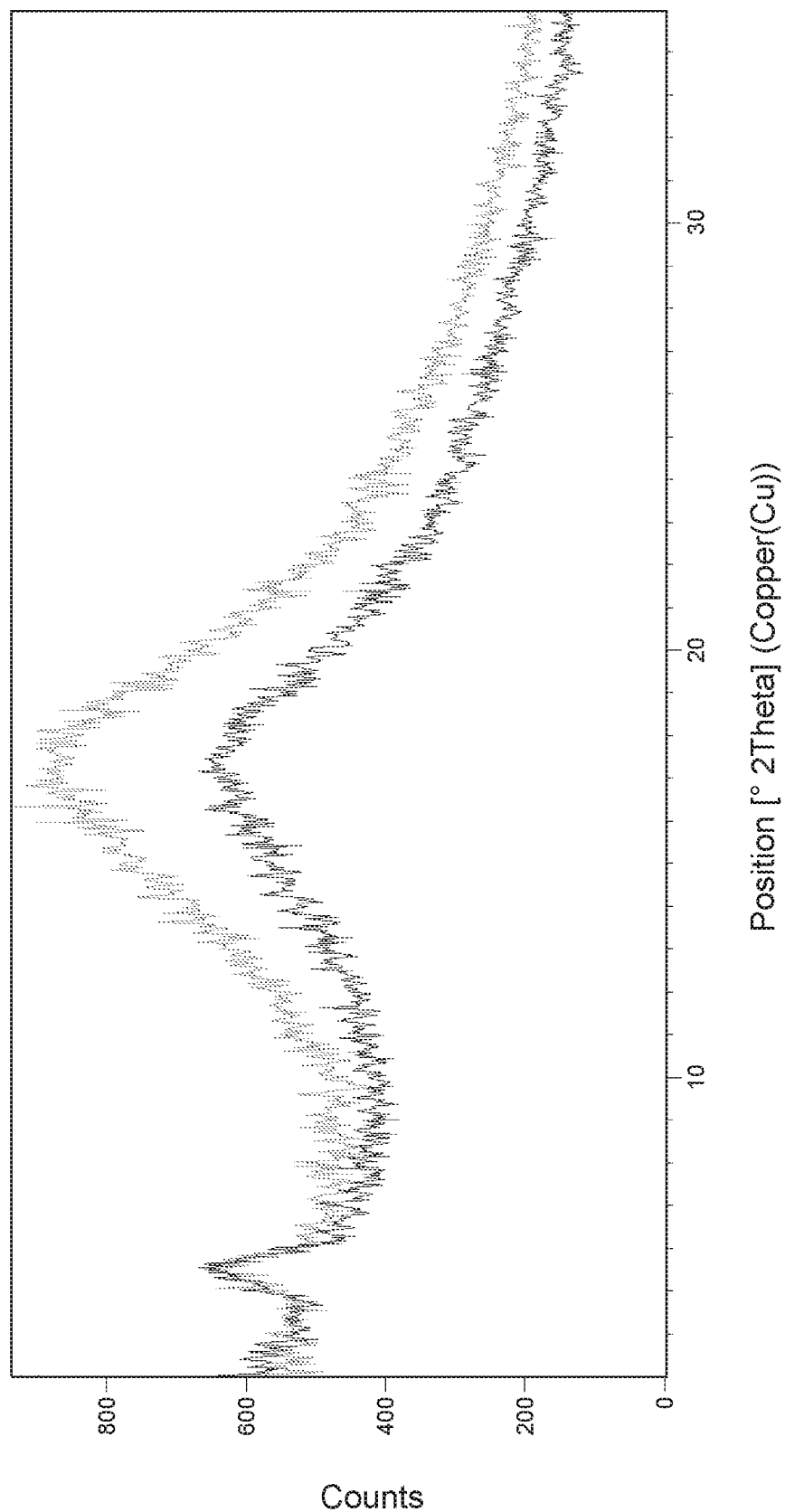
FIG. 43 shows the X-ray powder diffractogram of the "input solid" for the isolation experiments in Example 18, which is the amorphous solid of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine was analyzed as received with the appearance of a beige to off-white glassy solid. Chemical purity by HPLC (generic low-pH method) was 92.98%. 1H NMR spectroscopy revealed a spectrum that conformed to structure (D₆DMSO). XRPD examination (FIG. 43) revealed that the solid was completely amorphous for both samples tested.

General Procedure for Isolation Following Elution via a C18 Reverse Phase Column 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine (150 mg) was dissolved in eluent at 45-50 mL and eluted via a C18 reverse phase column at 2 mL/minute. This was followed by flushing the column and testing for product content using 50-100 mL of eluent. The eluent was reduced in vacuo using a rotary evaporator at 35° C. to produce solids for analysis. The resulting samples were then dried overnight at 18-35° C. in vacuo ahead of analysis. In some instances, analysis of the damp solids was collected.

Column details: C18 Phenomenex 5 micron, Luna; 100 Å; 150×4.6 mm

Example 18A: 100% CH₃CN

The column was loaded with 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine in 50 mL of CH₃CN. Note that precipitation of a voluminous solid takes place over 10 minutes in 10 mL CH3CN used to initially mobilize solids. At 50 mL volume with warming at <40° C., dissolution takes place. Clarification via a 0.45 micron frit was employed prior to chromatography.

Elution was completed using 40 mL CH₃CN.

Evaporation at 35° C. was complete within 2 hours and dried at 18° C. overnight (18 h) in vacuo.

The resulting solid was a yellow glass in appearance.

Figure 44:
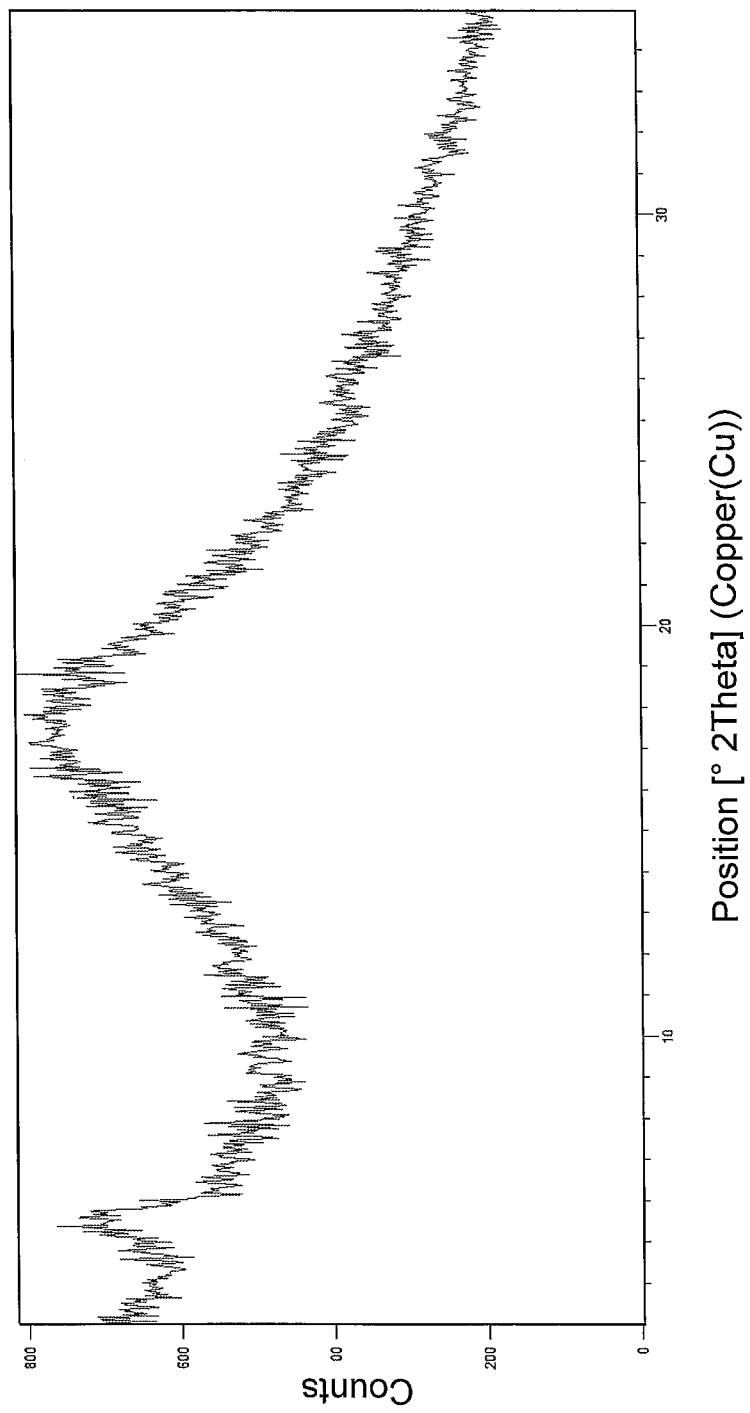
FIG. 44 shows the X-ray powder diffractogram of the solid isolated from CH$_3$CN post chromatography in Example 18A.

Result: XRPD of the solid post reduction in vacuo was amorphous (FIG. 44).

Example 18B: 9:1 CH₃CN:water

The column loaded with 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine in 50 mL CH₃CN/water (9:1). Solids dissolved at 50 mL volume with warming at <40° C., dissolution readily takes place. Clarification via a 0.45 micron frit was employed prior to chromatography.

Elution was complete using 50 mL CH₃CN/water (9:1).

Evaporation at 35° C. was complete within 2.9 hours and dried at 18° C. overnight (18 h) in vacuo. Solids remain damp.

The resulting mass was a yellow glass in appearance with white granular solids present.

Figure 45:
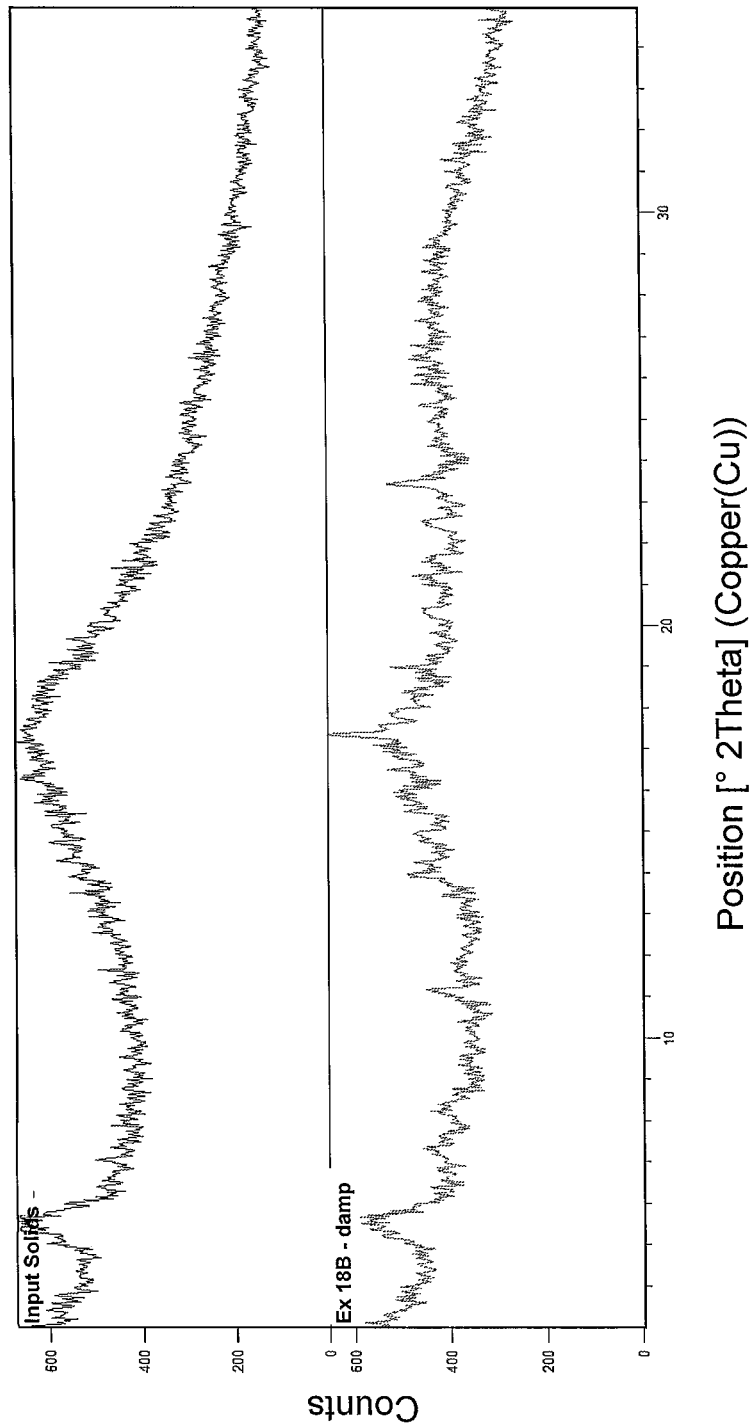
FIG. 45 shows the X-ray powder diffractogram comparison of the input solid (top) and of the damp solid (bottom) of the solid isolated from 9:1 CH$_3$CN/water post chromatography and evaporation at 18° C. overnight in Example 18B, demonstrating a partially crystalline pattern of the isolated solid.

Result: XRPD of the solid post drying in vacuo was predominantly amorphous, or equally relevant, partially crystalline, XRPD pattern (FIG. 45).

Figure 46:
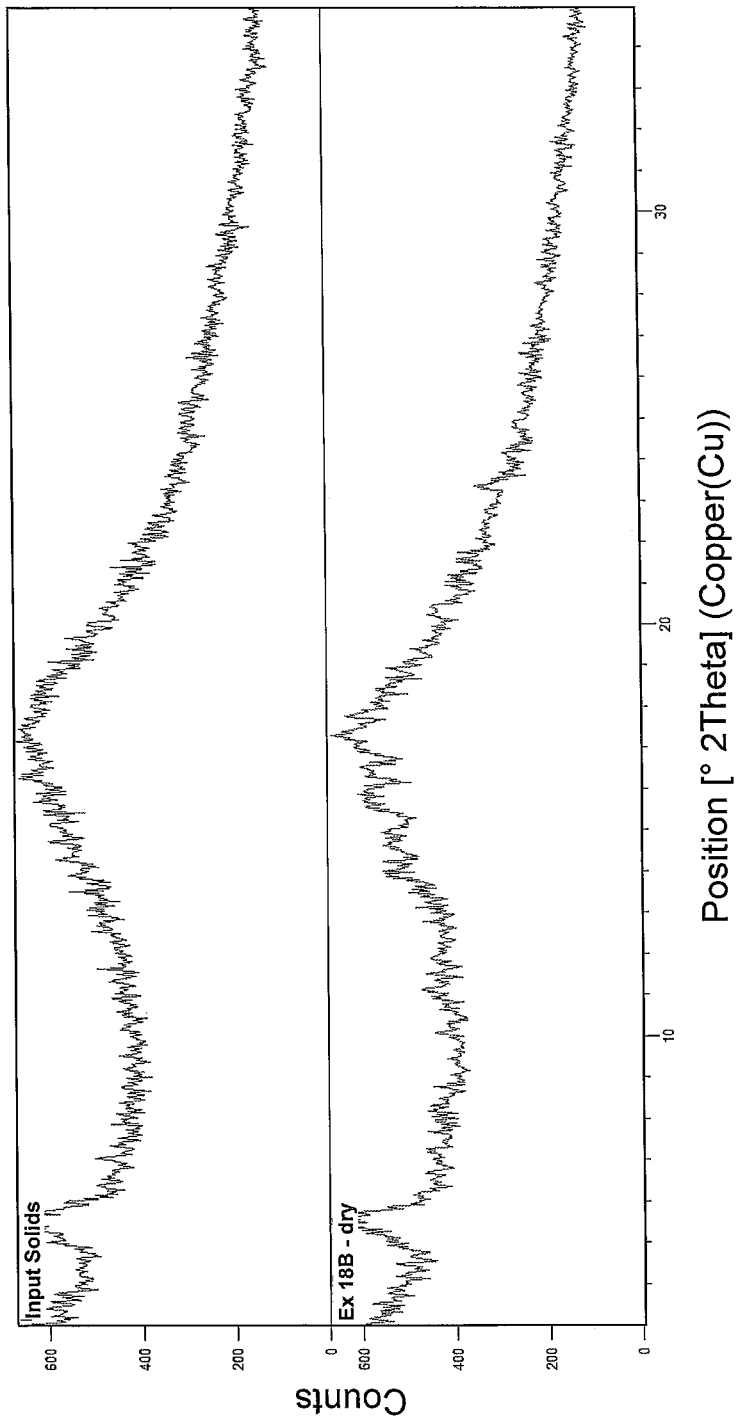
FIG. 46 shows the X-ray powder diffractogram comparison of the input solid (top) and of the dry solid (bottom) of the solid isolated from 9:1 CH$_3$CN/water post chromatography and evaporation at 18° C. overnight, and then further evaporation at 35° C. in Example 18B, demonstrating a partially crystalline pattern of the isolated solid.

The solids post drying in vacuo at 35° C. to remove further water demonstrated a predominantly amorphous, or equally relevant, partially crystalline, XRPD pattern (FIG. 46).

Example 18C: 1:9 CH₃CN:water

The column was loaded with 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine in 45 mL CH₃CN/water (1:9) and 5 mL CH3CN used to mobilize the solid (50 mL total). Solids dissolved at 50 mL volume with warming at <40° C., dissolution takes place following mild agitation. Clarification via a 0.45 micron frit was employed prior to chromatography.

Elution was complete using 50 mL CH₃CN/water (1:9).

Evaporation of half of the batch at 35° C. was complete within 3 hours to leave an aqueous emulsion/solid state that was held overnight due to time constraints. The remainder was reduced in vacuo the next day and 6 h were required to remove water without product loss due to bumping at <35° C.

The resulting mass was a white powder in appearance in the damp state.

Figure 47:
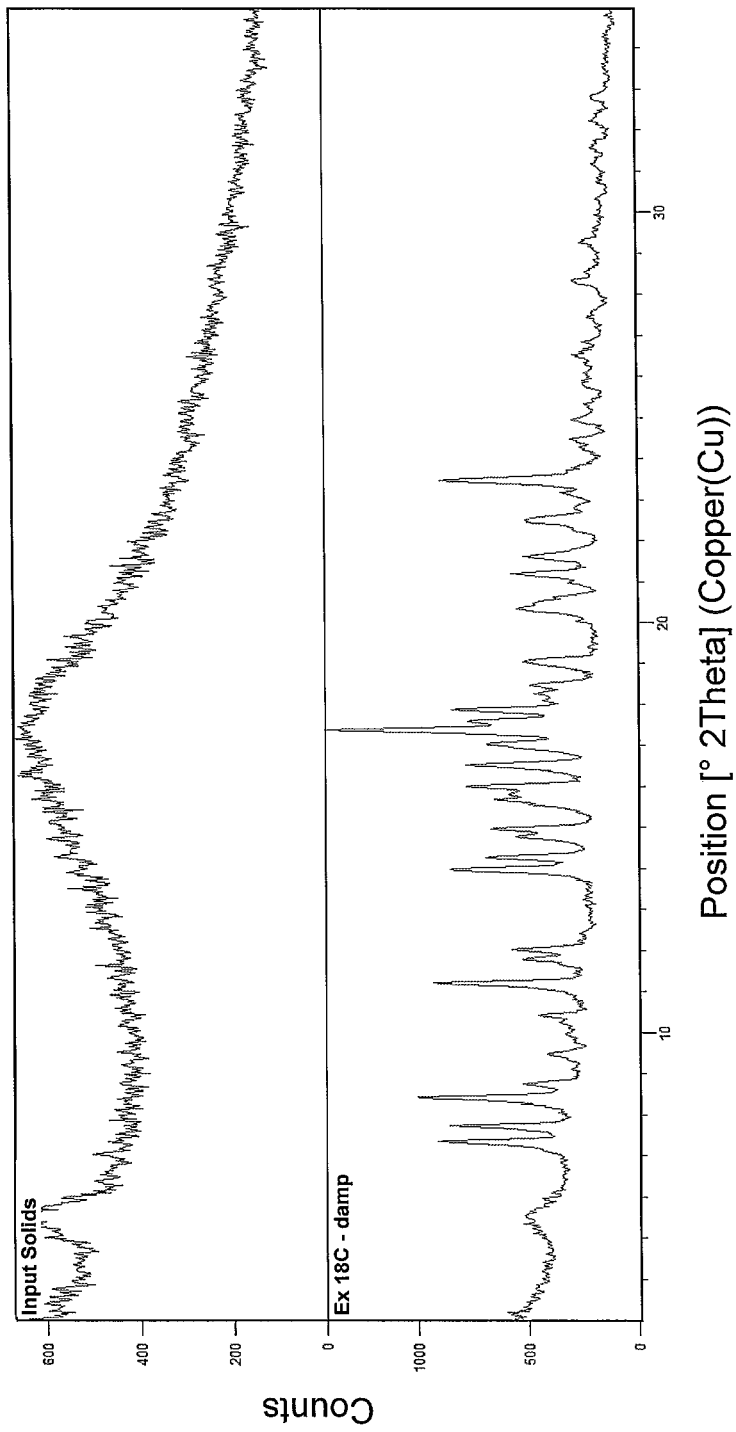
FIG. 47 shows the X-ray powder diffractogram comparison of the input solid (top) and of the damp solid (bottom) of the solid isolated from 1:9 CH$_3$CN/water post chromatography and evaporation at 18° C. overnight in Example 18C, demonstrating a highly crystalline pattern of the isolated solid.

Result: XRPD of the solid post reduction in vacuo was highly crystalline (FIG. 47).

Figure 48:
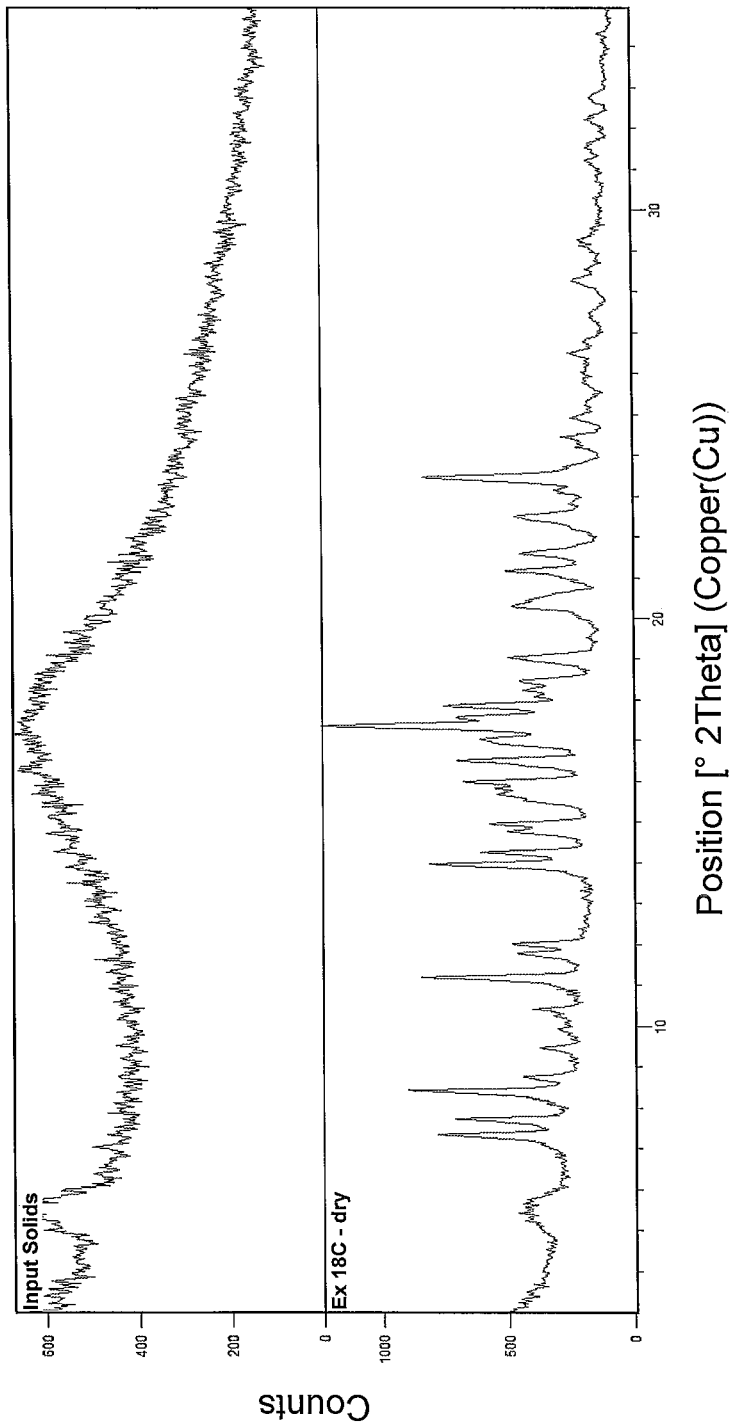
FIG. 48 shows the X-ray powder diffractogram comparison of the input solid (top) and of the dry solid (bottom) of the solid isolated from 1:9 CH$_3$CN/water post chromatography and evaporation at 18° C. overnight, and then further evaporation at 35° C. in Example 18C, demonstrating a highly crystalline pattern of the isolated solid.
Figure 49:
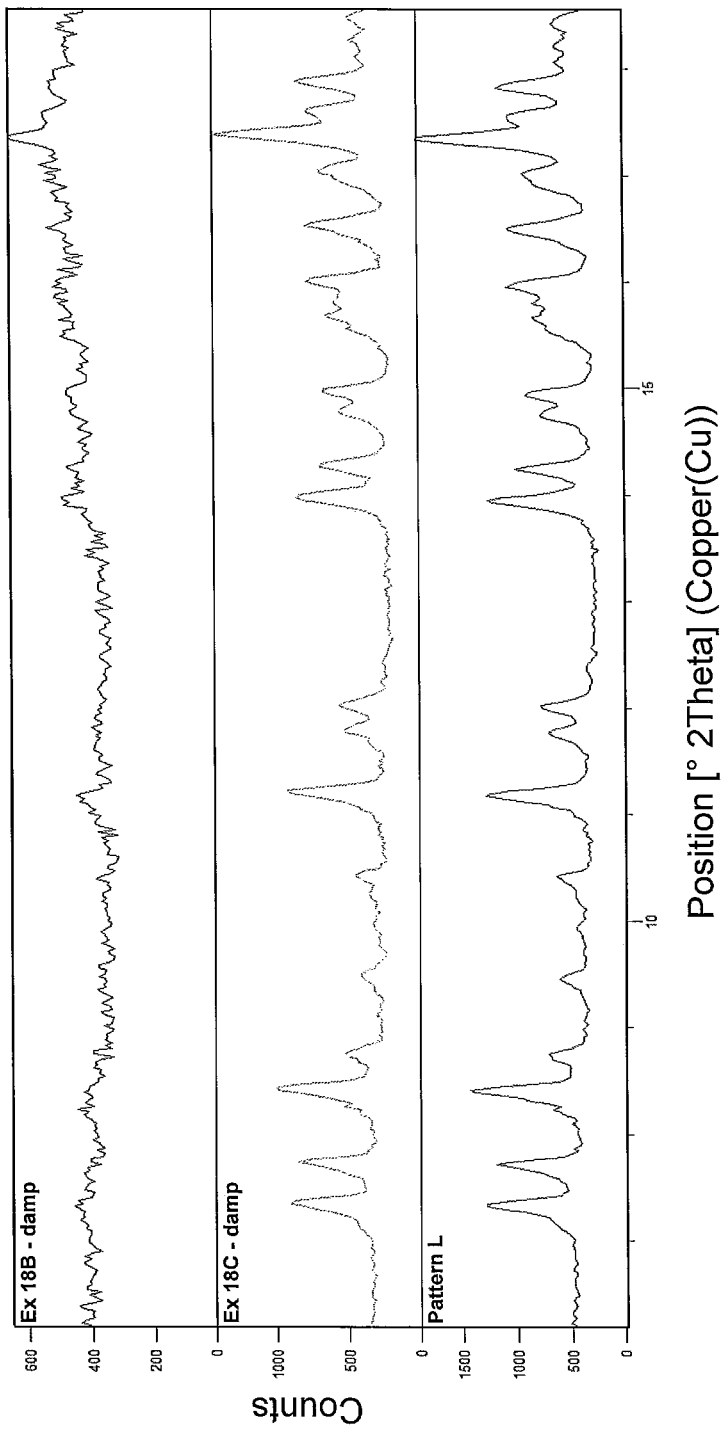
FIG. 49 shows an expansion of the X-ray powder diffractogram comparison of the damp solid isolated from Example 18B (top), of the damp solid isolated from Example 18C (middle), and of crystalline hydrate Form L of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine (bottom), demonstrating that the solid forms isolated in Examples 18B and 18C correspond to crystalline hydrate Form L.

The solids post drying in vacuo at 35° C. to remove further water demonstrated a highly crystalline and equivalent profile (FIG. 48).

CONCLUSIONS

The crystalline phase represented within Example 18B and 18C was identified as

Pattern L. This phase requires drying at temperatures in excess of 70° C. to remove water and provide an amorphous phase.

Isolation of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine from acetonitrile/water provides crystalline or partially crystalline solids with results varying dependent upon the starting eluent composition being removed and the conditions employed within the laboratory. Standard drying conditions of <40° C. in vacuo do not return an amorphous solid.

Use of acetonitrile alone provides amorphous solids, but this does require speed or a solid phase that is likely to be a solvate will form.

What is claimed is:

1. A composition comprising crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

2. The composition of claim 1 wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the X-ray powder diffraction pattern as shown in FIG. 3.

3. A composition comprising crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6- tetrahydropyrrolo[3,4-c]pyrazol-3-amine characterized by an X-ray diffraction pattern reflections at a 2 theta value of 18.1, 6.8, 15.3 and 22.1.

4. The composition of claim 3 wherein the crystalline Form A is further characterized by X-ray diffraction pattern reflections at 2 theta values of 12.9, 13.6, 15.7, 17.2, 21.2, 21.7, 22.8 and 28.4.

5. The composition of claim 3 wherein the crystalline Form A is further characterized by at least one X-ray diffraction pattern reflection selected from a 2 theta value of 6.8, 12.9, 13.6, 15.3, 15.7, 17.2, 18.1, 21.2, 21.7, 22.1, 22.8 and 28.4.

6. The composition of claim 3 wherein the crystalline Form A is further characterized by at least two X-ray diffraction pattern reflections selected from a 2 theta value of 6.8, 12.9, 13.6, 15.3, 15.7, 17.2, 18.1, 21.2, 21.7, 22.1, 22.8 and 28.4.

7. The composition of claim 3 wherein the crystalline Form A is further characterized by at least three X-ray diffraction pattern reflections selected from a 2 theta value of 6.8, 12.9, 13.6, 15.3, 15.7, 17.2, 18.1, 21.2, 21.7, 22.1, 22.8 and 28.4.

8. The composition of claim 3 wherein the crystalline Form A is further characterized by at least four X-ray diffraction pattern reflections selected from a 2 theta value of 6.8, 12.9, 13.6, 15.3, 15.7, 17.2, 18.1, 21.2, 21.7, 22.1, 22.8 and 28.4.

9. The composition of claim 3 wherein the crystalline Form A is further characterized by at least five X-ray diffraction pattern reflections selected from a 2 theta value of 6.8, 12.9, 13.6, 15.3, 15.7, 17.2, 18.1, 21.2, 21.7, 22.1, 22.8 and 28.4.

10. The composition of claim 3 wherein the crystalline Form A is further characterized by at least six X-ray diffraction pattern reflections selected from a 2 theta value of 6.8, 12.9, 13.6, 15.3, 15.7, 17.2, 18.1, 21.2, 21.7, 22.1, 22.8 and 28.4.

11. The composition of claim 1 wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the differential scanning calorimetry pattern as shown in FIG. 5.

12. The composition of claim 1 wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the thermogravimetric analysis pattern as shown in FIG. 6.

13. The composition of claim 1 wherein the crystalline 2-propanol solvate Form A of 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine exhibits the infrared spectrum as shown in FIG. 7.

* * * * *